United States Patent [19]
Wiggins et al.

[11] Patent Number: 5,705,623
[45] Date of Patent: Jan. 6, 1998

[54] MAMMALIAN GLOMERULAR EPITHELIAL PROTEIN 1

[75] Inventors: Roger C. Wiggins; Peedikayil E. Thomas, both of Ann Arbor, Mich.

[73] Assignee: The University of Michigan, Ann Arbor, Mich.

[21] Appl. No.: 201,697

[22] Filed: Feb. 25, 1994

[51] Int. Cl.$^6$ .............................. C07H 21/04; C12N 9/16
[52] U.S. Cl. ............................................ 536/23.2; 435/196
[58] Field of Search ........................... 435/240.1, 252.3, 435/252.33, 320.1; 536/23.5, 23.2

[56] References Cited

PUBLICATIONS

Thomas et al., "Molecular cloning of a glomerular epithelial cell specific membrane protein cDNA." *FASEB J* 5:A907 (1991).

Thomas et al., "Cloning and characterization of a glomerular epithelial cell specific protein (GLEPP1)." *J. of Am. Society of Nephrology* 2:566 (1991).

Schrier and Gottschalk, "Biochemical, structural, and functional correlations in the kidney." *Diseases of the Kidney*, 1:14–15 (1993).

Wiggins et al., "GLEPP1 is a multimeric podocyte membrane protein with a developmental pattern similar to that of podocalyxin." *J. of Am. Society of Nephrology* 3:622 (1992).

Thomas et al., "GLEPP1 is a podocyte specific transmembrane protein with a cytosolic protein tyrosine phosphatase domain." *FASEB J* 7:A214 (1993).

Wiggins et al., "GLEPP1 is a glomerular epithelial cell-specific transmembrane protein with a cytosolic protein tyrosine phosphatase domain." *Kidney International* (Jan., 1994).

Wiggins et al., "GLEPP1, a podocyte specific membrane protein tyrosine phosphatase from rabbit and man." *Clinical Research Meeting* (Apr., 1994).

Thomas et al. (1994) J. Biol. Chem. 269(31): 1953–19962.

*Primary Examiner*—Robert A. Wax
*Assistant Examiner*—Lisa J. Hobbs
*Attorney, Agent, or Firm*—Campbell & Flores LLP

[57] ABSTRACT

This invention provides mammalian GLEPP1 proteins, which are expressed primarily on glomerular podocytes. The invention also provides DNA sequences encoding mammalian GLEPP1 proteins and PTPase domains of mammalian GLEPP1 proteins. The invention further provides methods of detecting and treating a glomerular pathology characterized by abnormally low GLEPP1 expression or abnormal distribution of GLEPP1 protein on a cell.

8 Claims, 14 Drawing Sheets

```
            1
Gleppl      P V Q L D D F I K D M A K D S Y K F S L Q F E L K L I G L D I P H F A
HPTPβ       P I I N Q F M K L Y R D N Y L K E Y E L K D V G N S C D I
DPTP 10D    P I K N F L R K A A D S D R F E E L K N V G R D Q P C T F
CONSENSUS   P         F   K   A D S D   F S E E L K   G     P A D L L P L N R C K N Y       R Y N N I L P Y D F       S R V R L L S M N E
HPTPβ       A D L L P L N R G K N F       R Y N N I L P Y D A       T R K L L N V D D
DPTP 10D    A D L L P L N R R P K N       R F N N I L P Y D A       R R F L L S Q P D
CONSENSUS   A D L L P   N R   K N         R   N N I L P Y D         S R   R L L     D 71
            E E G A D Y I N A N Y I P G   Y N S L P P Q E   Y T G P L P E
HPTPβ       E D P C S Y I N A N Y I P G   Y N H P V P G P R   Y I G P L P H S
DPTP 10D    D E G S D Y I N A N Y I P G   Y N N H P G P R   Y F G P L P H S
CONSENSUS   E       D Y I N A N Y I   P G   Y N   P   P     Y     G P     E 140
            Q Q K S Q M I V M L T C Q V E K R R V Y H P P Y F T E E D V
HPTPβ       Q N V H A I V V M L T R V C K K G R V Y M P P A D T
DPTP 10D    E S N R A I V V M L T R C F E K K R V Y W P P   A D T
CONSENSUS   Q     A I V V M L T C     K R R V Y   P P Y   T E   D
```

MAMMALIAN GLOMERULAR EPITHELIAL PROTEIN 1

BACKGROUND OF THE INVENTION

This work was supported by grant numbers DK 46073 and DK 39255 awarded by the National Institutes of Health. The government has rights in the invention.

1. Field of the Invention

This invention relates to the fields of molecular genetics and cell biology and, in particular, to a mammalian protein present on glomerular cells.

2. Background Information

The kidney is the organ in vertebrates chiefly responsible for eliminating wastes from the blood and regulating the blood's chemical balance. The anatomy of the kidney and the architecture of the cells that compose it are related to its function.

The glomerulus is the structure in the kidney that filters blood. The major filtration surface of the glomerulus consists of a basement membrane covered by fenestrated endothelial cells and specialized epithelial cells, called podocytes. Podocytes have delicate interdigitating foot processes that cover the exterior basement membrane surface of the glomerular capillary. Podocytes are responsible in part for the charge and size filtration characteristics of the glomerulus.

When a dysfunction of glomerular filtration occurs, proteins from the blood can leak into the urine and illness and death can result. The major anatomic abnormality associated with this dysfunction is effacement, or fusion, of the podocyte foot processes. The molecular mechanisms underlying these dysfunctions are not well understood.

Thus, there exists a need for identifying the molecular defects associated with the gross pathological changes that occur in kidney disease and for developing methods for identifying and treating the molecular defects. The present invention satisfies these needs and provides related advantages as well.

SUMMARY OF THE INVENTION

The invention provides isolated mammalian GLEPP1 proteins such as human GLEPP1 protein and rabbit GLEPP1 protein. The invention also provides isolated polypeptides comprising a protein tyrosine phosphatase (PTPase) domain of a mammalian GLEPP1 protein. In addition, the invention provides antibodies specific for a mammalian GLEPP1 protein.

The invention further provides isolated nucleic acid sequences encoding a mammalian GLEPP1 protein or a PTPase domain of a mammalian GLEPP1 protein. The invention also provides vectors that can express a nucleic acid sequence encoding a mammalian GLEPP1 protein. In addition, the invention provides host cells that contain the vectors and express the polypeptide. The invention also provides nucleic acid probes having a nucleotide sequence corresponding to a portion of a mammalian GLEPP1 gene such as the human GLEPP1 gene and the rabbit GLEPP1 gene.

The invention further provides methods of detecting the presence of a glomerular pathology in a subject comprising detecting an abnormally low level of GLEPP1 mRNA or GLEPP1 protein expression in a podocyte. The invention also provides methods of detecting a glomerular pathology comprising detecting the presence of a defective GLEPP1 gene in a subject. In addition, the invention provides methods of treating a glomerular pathology characterized by an abnormally low level of expression of GLEPP1 protein comprising introducing a nucleic acid molecule encoding a normal mammalian GLEPP1 protein or a PTPase domain of a mammalian GLEPP1 protein into a subject and expressing the normal protein or domain.

Figure 1:
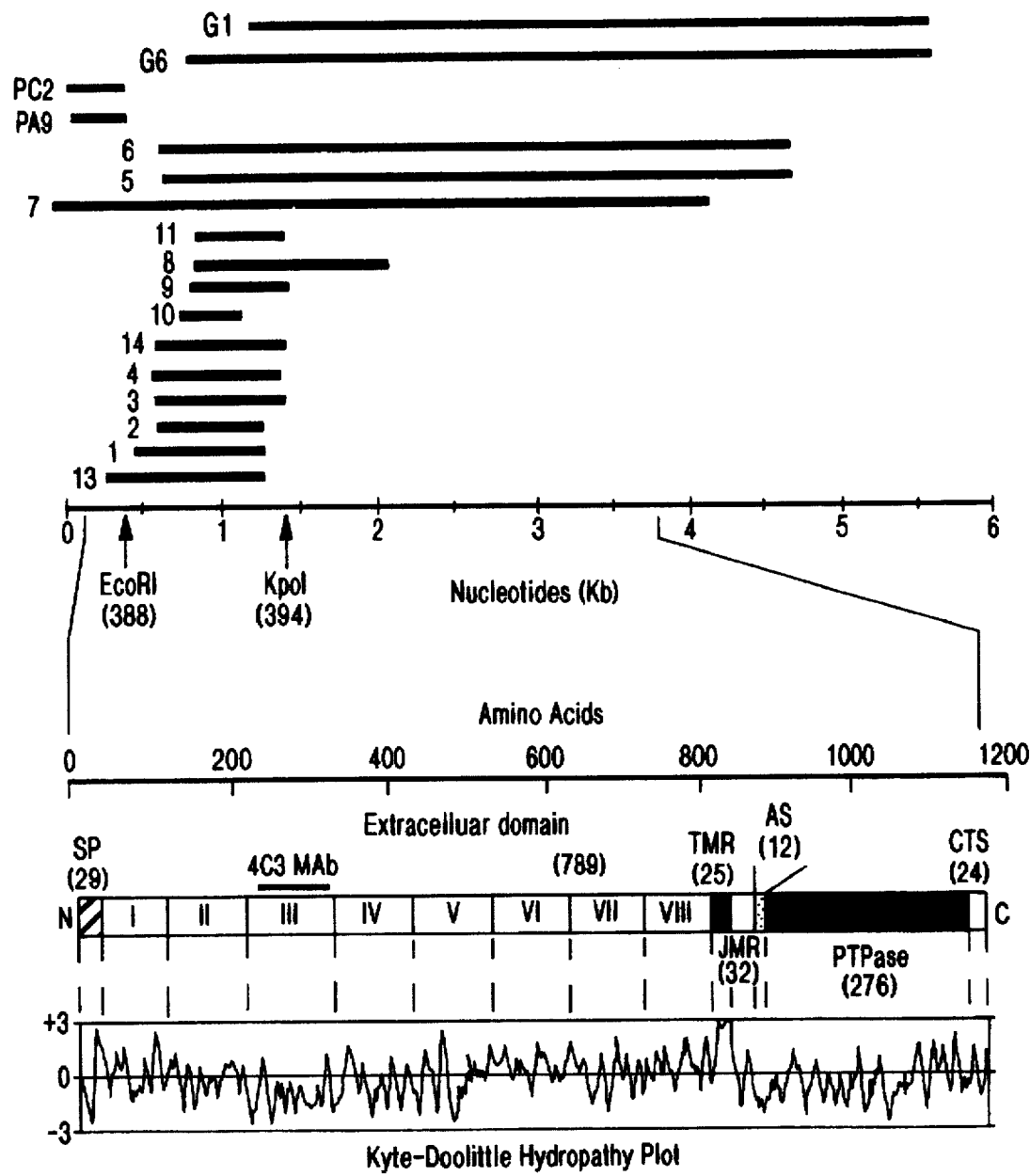
FIG. 1 presents a diagrammatic representation of the cDNAs used to derive the rabbit GLEPP1 nucleotide sequence showing (a) cDNAs cloned using the 4C3 MAb (clones 1 to 11, 13, 14), (b) cDNAs cloned using cDNA #7 for screening (G1 and G6), and (c) cDNAs cloned using polymerase chain reaction (PCR) strategies (PC2 and PA9).

All cDNAs were sequenced in both directions, except that only part of clone G1 was sequenced. Clones 7, G1 and G6 each contained a 36 nucleotide putative alternative splice region, whereas clones 5 and 6 did not contain this region. The cDNA clones obtained by screening with the MAb 4C3 overlap. The lower part of the figure illustrates the structure of a GLEPP1 protein as derived from the nucleotide sequence and aligned using the Kyte-Doolittle amino acid hydropathy plot. The number of amino acids comprising each part of the molecule is shown in parentheses (total=1, 187).

A single putative transmembrane region (TMR) consisting of a 25 amino acid hydrophobic region is shown (filled in black box). The extracellular domain consists of eight fibronectin type III-like repeats (labelled I to VIII). The N-terminal region consists of a 29 amino acid putative signal peptide (SP). The intracellular part of the molecule (C-terminal to the TMR) contains a 32 amino acid juxtamembrane region (JMR), followed by a putative alternatively spliced (AS) region immediately N-terminal to the PTPase domain (active site region of the PTPase shown as a dark band). The Sequence contains a 24 amino acid C-terminal segment (CTS). The region of binding of the 4C3 MAb is shown as a black bar above the extracellular domain.

Figure 2A:
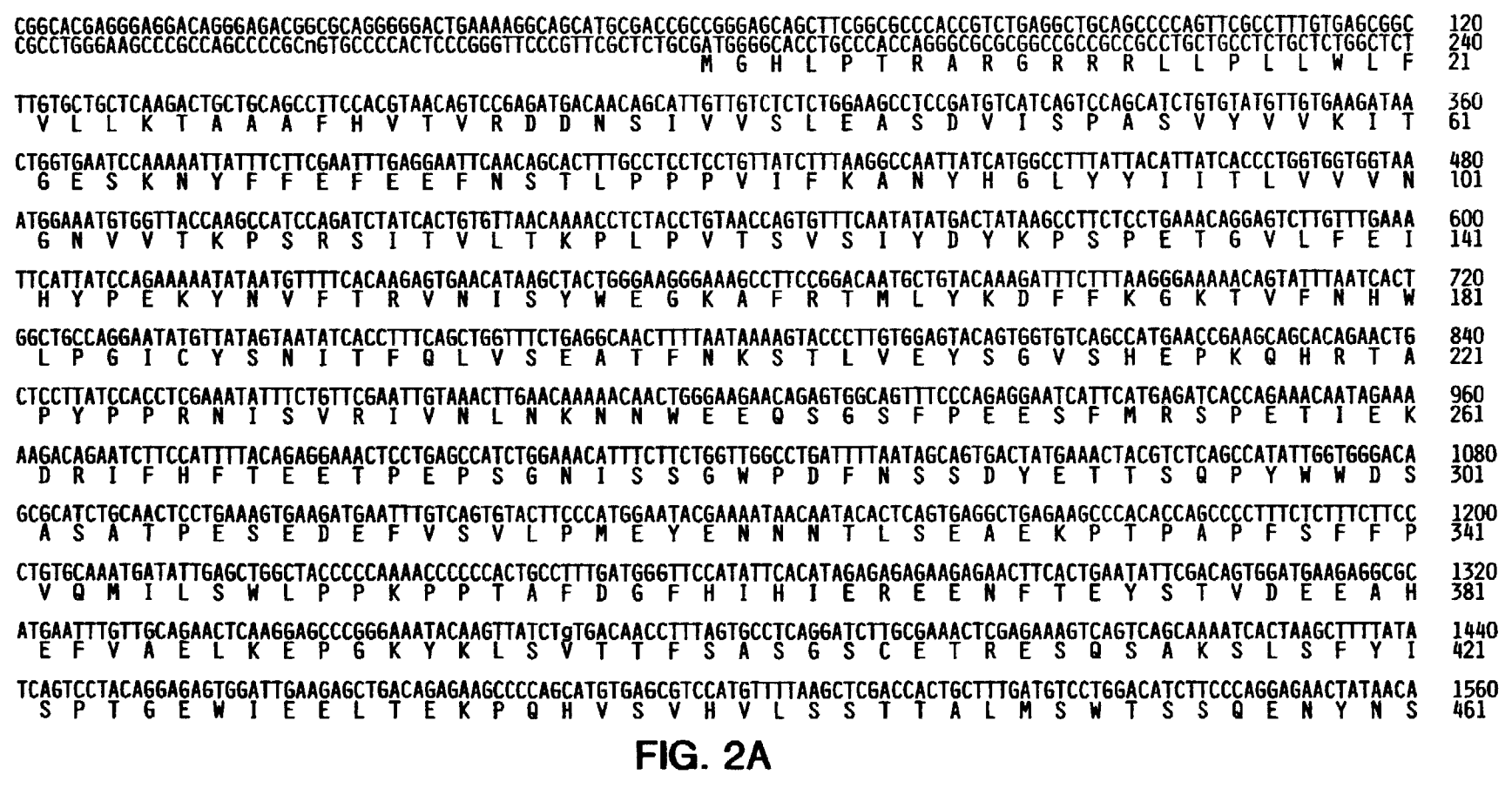
Figure 2B:
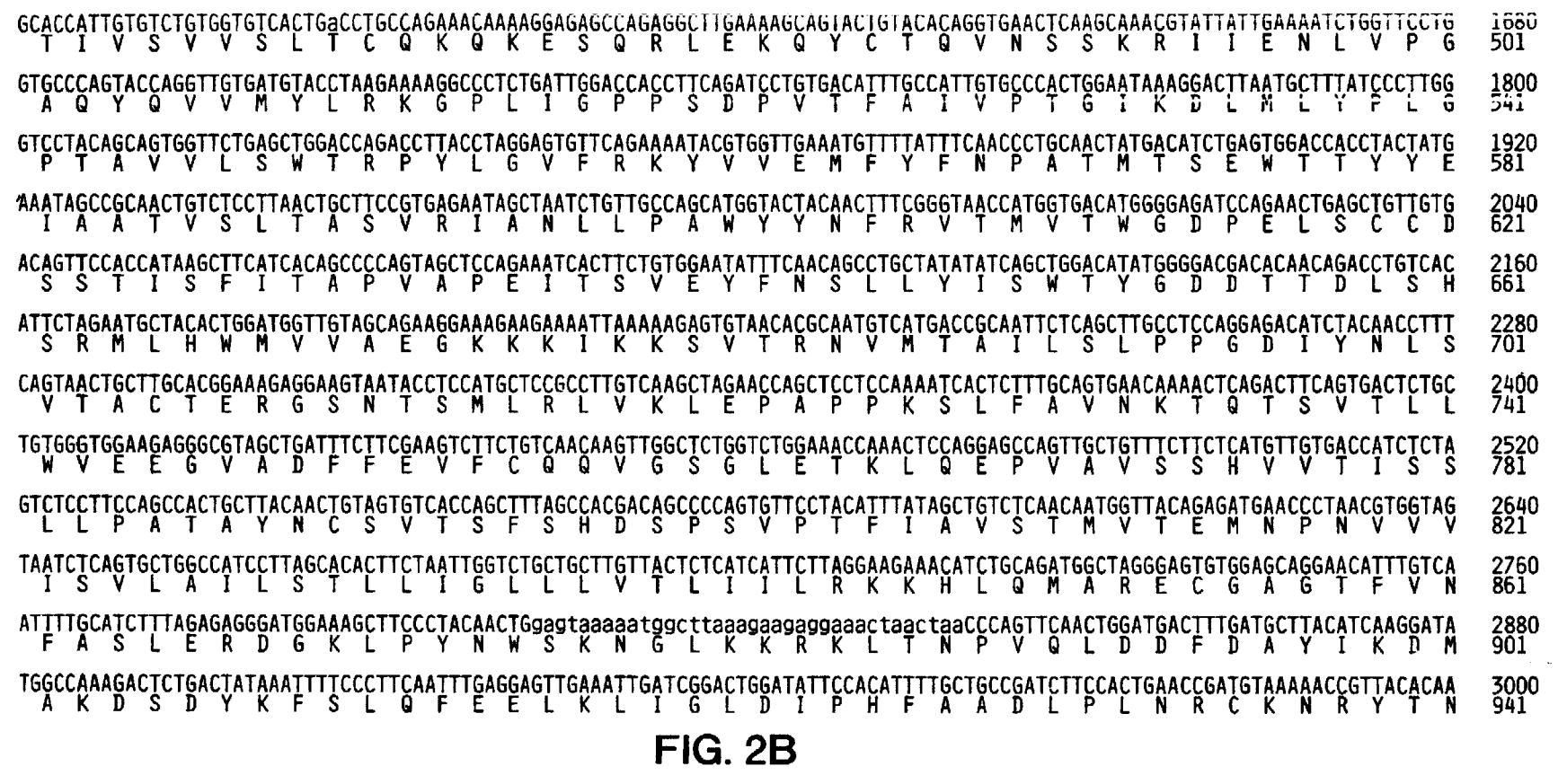
Figure 2C:
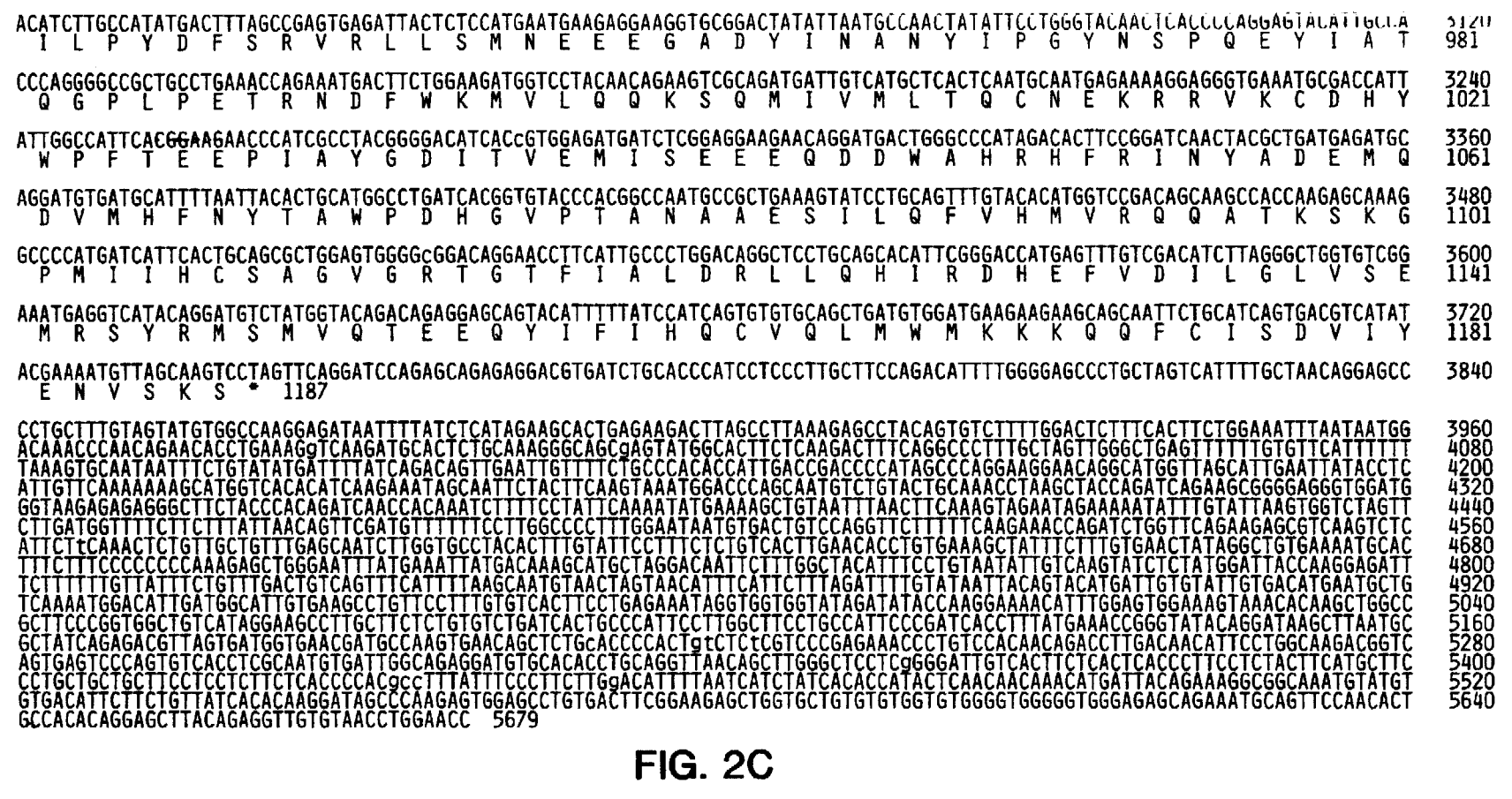

FIG. 2 shows the rabbit GLEPP1 nucleotide sequence (SEQ ID NO: 1) and the derived amino acid sequence (SEQ ID NO: 2). The initiation methionine was identified as the first ATG in the open reading frame and obeys Kozak's consensus. The following sequences are underlined: (*) a 29 residue signal peptide containing 11 consecutive hydrophobic residues; () a transmembrane region comprising 25 hydrophobic residues; (*) a putative 12 residue alternately spliced region; (**) a PTPase domain containing an active site sequence (***, double underline).

The nucleotide sequences derived from all GLEPP1 clones were not identical as follows: (a) nucleotide 1,368 was C in clone 11 (CTG would code for leucine) and G in clones 3, 4, 8, 9, 14, G1, G6 (GTG would code for valine); (b) nucleotide 3,516 was C in clones 5 and 6 (CGG would code for arginine) and A in clones 7, G1 and G6 (AGG would also code for arginine); (c) nucleotide 4,013 was G in clones 5 and 6 and A in clones 7, G1 and G6 (noncoding region); (d) nucleotide 4,566 was T in clones 5 and 6 and C in clones G1, G6 (noncoding region). For the nucleotide sequence shown in this Figure, the most prevalent nucleotide at this position is listed. For nucleotide 4,566, where each example was found in two clones, C is listed.

Figure 3:
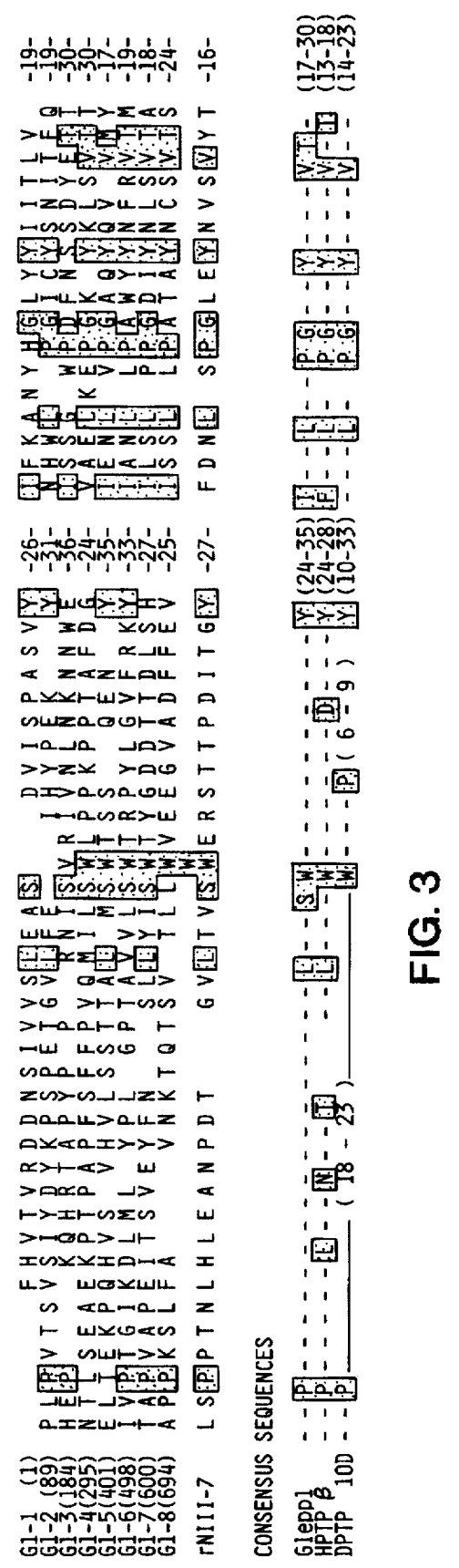

FIG. 3 depicts an analysis of a rabbit GLEPP1 extracellular domain. Eight fibronectin type III (FN III)-like repeats comprise the GLEPP1 extracellular region (789 amino acids). These sequences are shown together with the sequence of an FN III domain of fibronectin (SEQ ID NO:15) (FN III-7; Kornblihtt et al., *EMBO J.* 4: 1755–1759

(1985)). Conserved amino acids (defined as those present in at least four of eight repeats) are shown in bold. For comparison are shown the consensus amino acids of the GLEPP1 FN III-like repeats together with the consensus sequences of FN III-like repeats from two single PTP domain membrane PTPases: human PTPβ which contains 16 FN-III-like domains and Drosophila PTP10D which contains 12 FN-III-like domains.

Figure 4B:
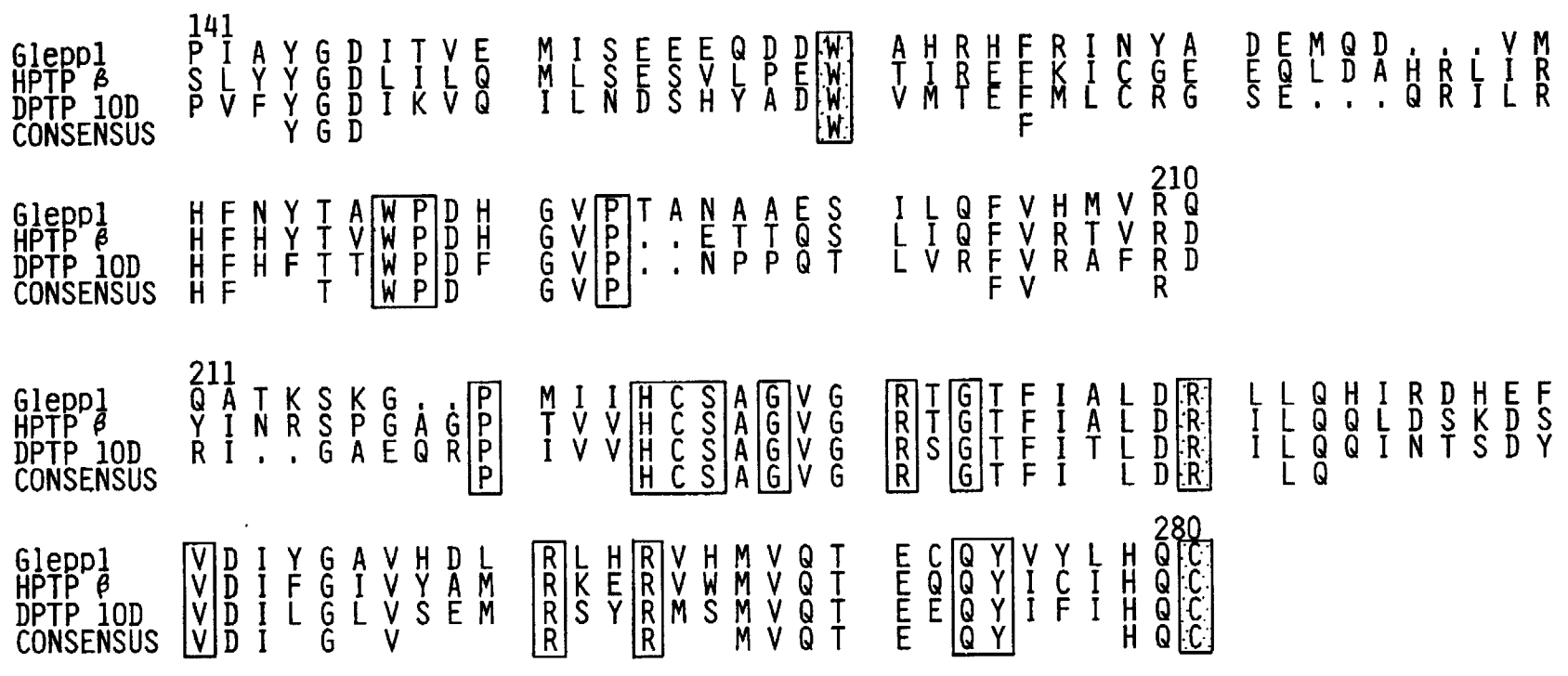

FIG. 4 compares rabbit the GLEPP1 PTPase amino acid sequence with two other type III receptor PTPases, human PTPβ [SEQ ID NO: 16] and Drosophila PTP10D [SEQ ID. NO:17], which are membrane PTPases that each have a single PTPase domain. The sequences were aligned to provide the greatest homology and consensus amino acids are indicated.

The type III receptor PTPase sequences also were compared with each of the two PTPase sequences of six tandem domain membrane PTPases (human CD45, human LAR, human PTPα, human PTPζ, Drosophila PTP and Drosophila PTP99A) and to three members of the intracellular single domain PTPase family (human T cell PTPase, PTP1β and human HePTP) (sequences not shown). The consensus amino acids shown in white boxes indicate amino acids that are common to at least 12 of the 15 non-type III receptor PTPases examined. The amino acids shown in black boxes are either not present or are represented only once in the 15 non-type III receptor PTPase sequences examined.

Figure 5A:
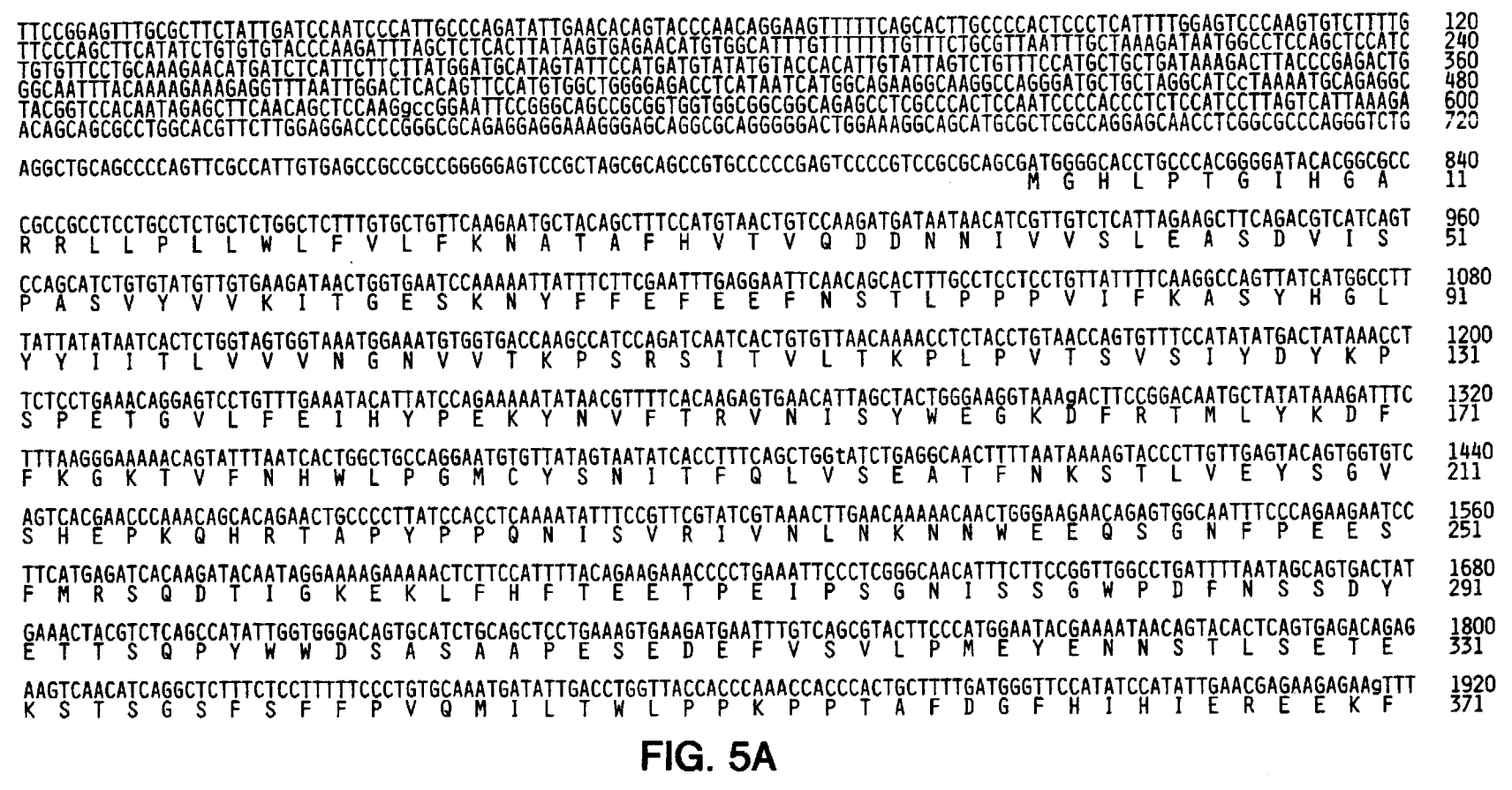
Figure 5B:
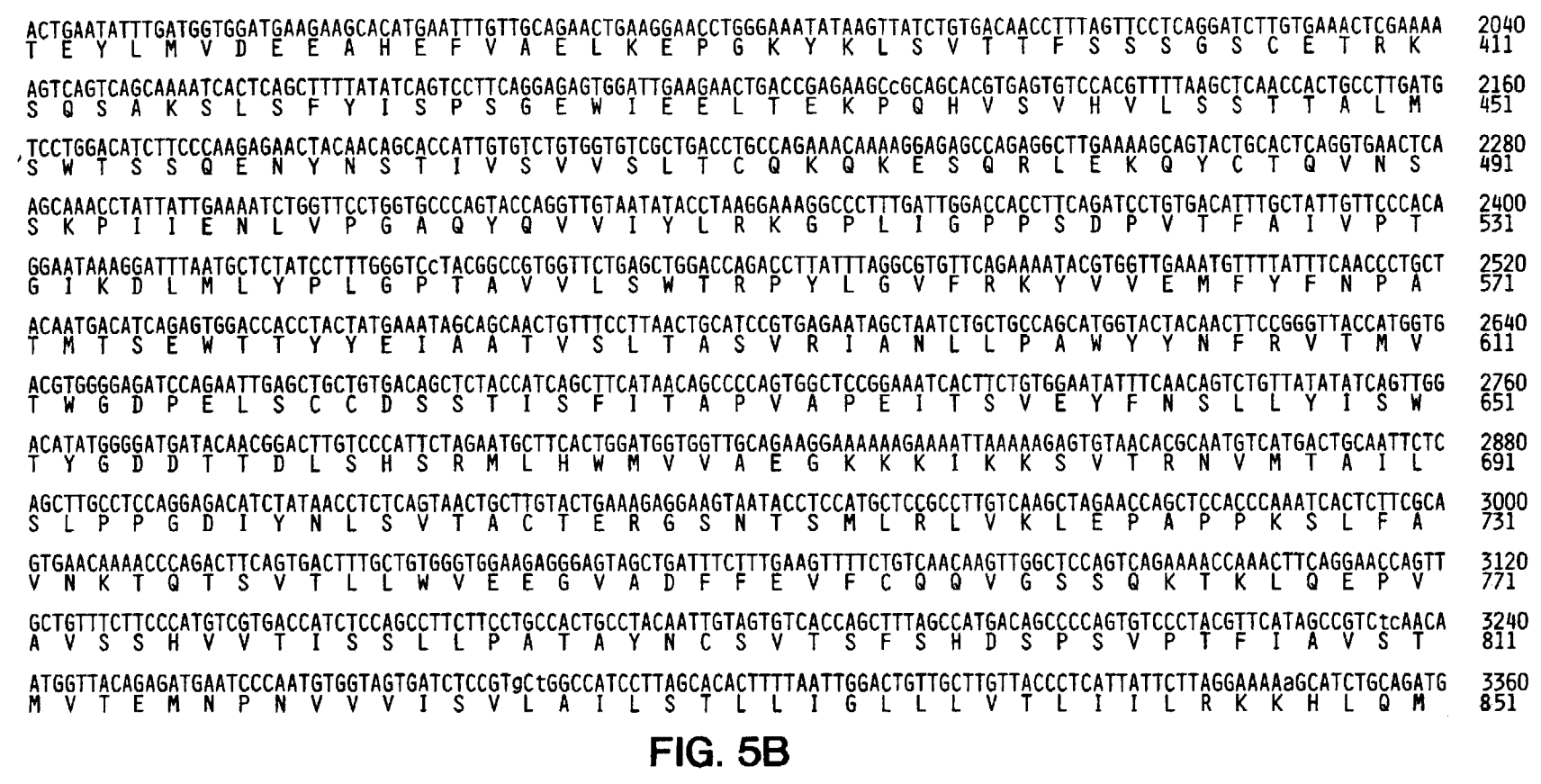
Figure 5C:
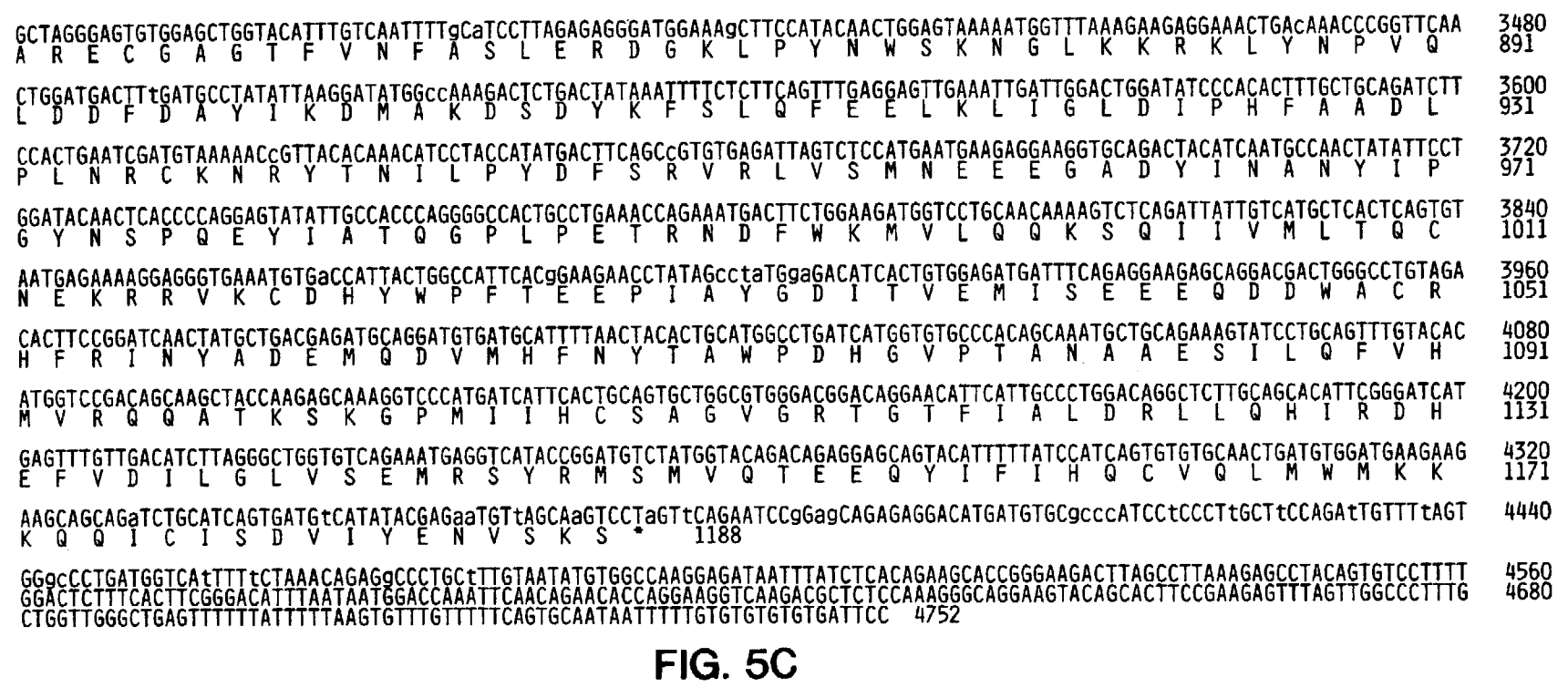

FIG. 5 lists the full length human GLEPP1 cDNA sequence (SEQ ID NO: 3) and the derived GLEPP1 amino acid sequence (SEQ ID NO: 4). The human GLEPP1 cDNA sequence has greater than 90% sequence identity with the rabbit GLEPP1 cDNA sequence. The human GLEPP1 amino acid sequence has greater than 96% sequence identity with the rabbit GLEPP1 amino acid sequence.

Figure 6A:
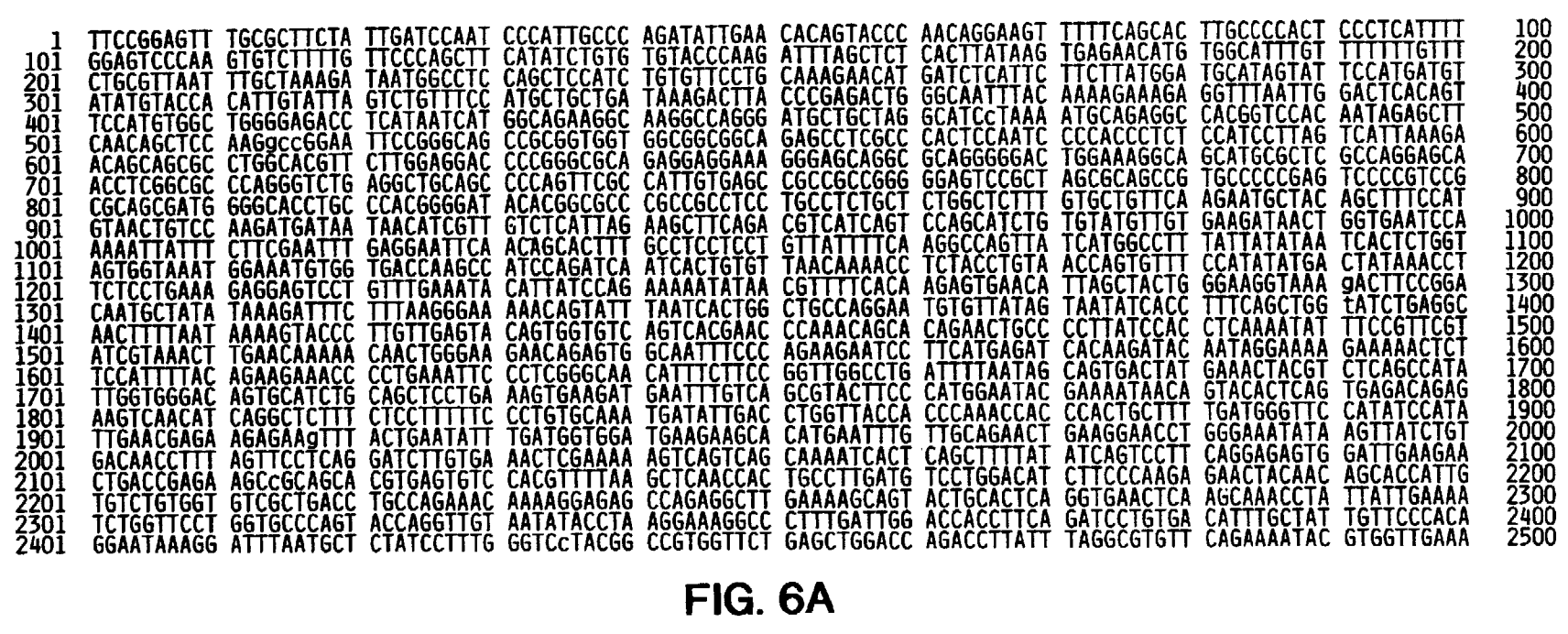
Figure 6B:
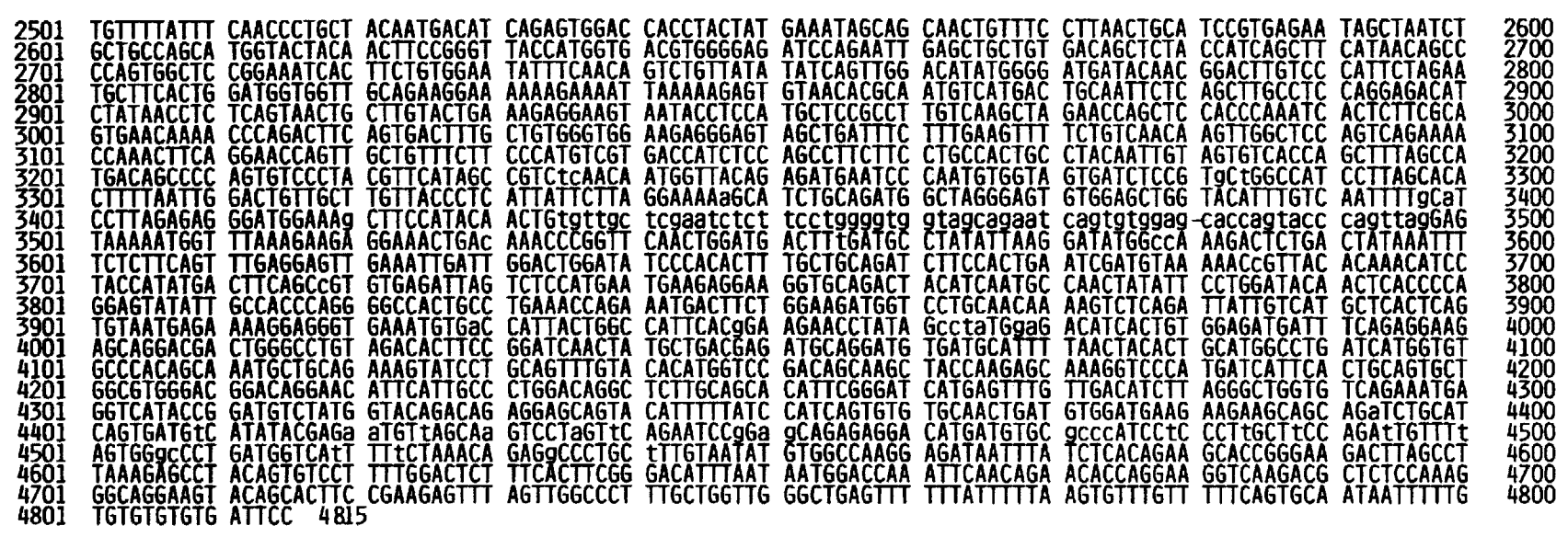

FIG. 6 lists the nucleotide sequence of an alternatively spliced cDNA encoding a human GLEPP1 protein (SEQ ID NO: 5). An additional nucleotide sequence, as compared to the cDNA sequence shown in FIG. 5, is indicated by lower case letters (positions 3435 to 3497).

Figure 7A:
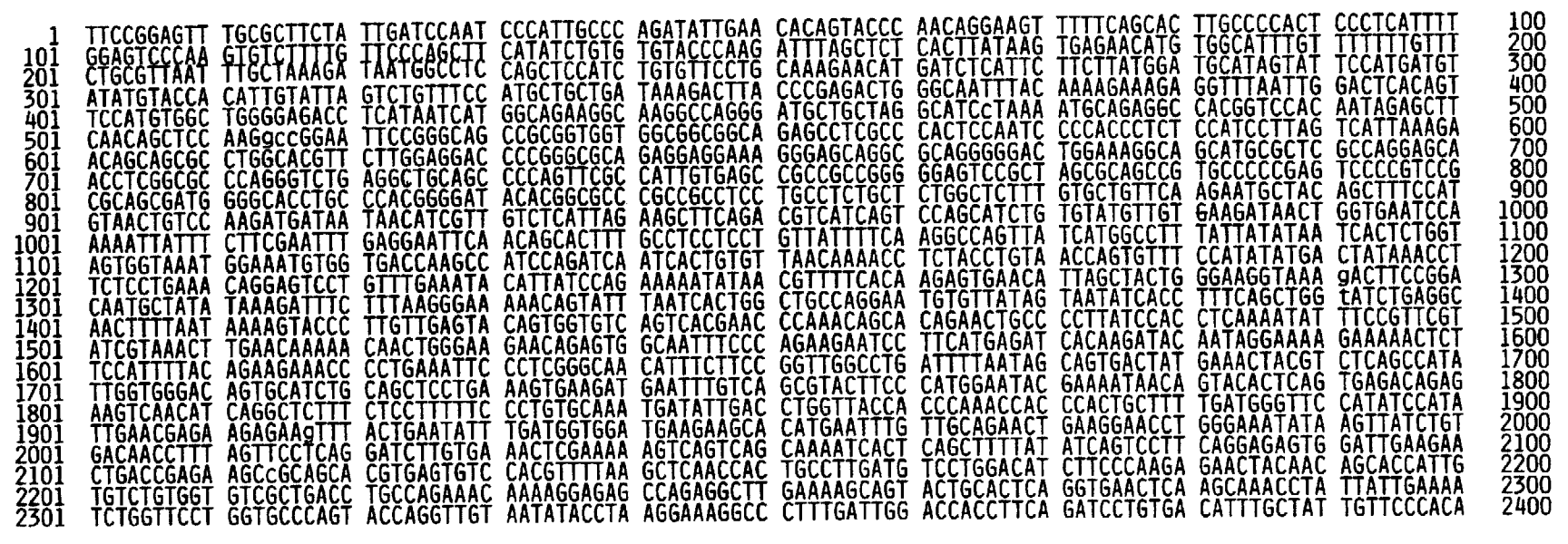

FIG. 7 lists the nucleotide sequence of a cDNA encoding a truncated form of a human GLEPP1 protein (SEQ ID NO: 6). The sequence encoding the truncated human GLEPP1 protein is identical to the nucleic acid sequence shown in FIG. 5 from positions 1 to 3554. The nucleotide sequence encoding the truncated human GLEPP1 protein then varies from the sequence shown in FIG. 5, as indicated by nucleotides shown in lower case. A STOP codon occurs at nucleotides 3604 to 3606 (TGA), resulting in an open reading frame encoding a 932 amino acid human GLEPP1 protein.

DETAILED DESCRIPTION OF THE INVENTION

The present invention provides an isolated protein that is primarily expressed in mammalian podocytes. More specifically, the invention provides isolated polypeptides comprising the amino acid sequence of a mammalian GLEPP1 protein or a PTPase domain of a mammalian GLEPP1 protein.

As used herein, the term "polypeptide" is used in its broadest sense to mean a sequence of amino acids. Thus, the term "polypeptide" is synonymous and interchangeable with the term "protein." In addition, a mammalian GLEPP1 protein can be a "proteoglycan," which also, therefore, is considered to be within the meaning of the term "polypeptide." The term "isolated" means a protein or a nucleic acid sequence that is essentially free of other biochemical molecules such as lipids, proteins or nucleic acids that the polypeptide or nucleic acid normally is associated with in nature. A polypeptide produced using methods of recombinant DNA technology is an example of an isolated polypeptide as is a polypeptide purified using routine biochemical and immunochemical methods. Similarly, a cloned nucleic acid sequence encoding a mammalian GLEPP1 protein or a PTPase domain is an example of an isolated nucleic acid sequence.

A mammalian GLEPP1 protein can be, for example, a rabbit GLEPP1 protein as shown in SEQ ID NO: 2 (FIG. 2), a human GLEPP1 protein as shown SEQ ID NO: 4 (FIG. 5) or a PTPase domain, which is contained within these sequences. Thus, as used herein, the term "mammalian GLEPP1 protein" can refer to a full length podocyte membrane protein such as a rabbit GLEPP1 having about 1187 amino acids (see Example II) or a human GLEPP1 protein having about 1188 amino acids as well as to an alternatively spliced form of a GLEPP1 protein, a truncated GLEPP1 protein (see Example V) or a PTPase domain of a mammalian GLEPP1 protein (Example II and V).

As used herein, the term "PTPase domain" means a portion of a GLEPP1 polypeptide that can be isolated in an active form having protein tyrosine phosphatase activity (see Examples II and III). A PTPase domain can be obtained, for example, by expressing a nucleotide sequence encoding the domain as described in Example III and the phosphatase activity of the domain can be determined using the methods described herein or otherwise known in the art.

A mammalian GLEPP1 protein can be characterized, in part, by having a large extracellular domain with a sequence containing eight fibronectin type III-like repeats, a hydrophobic transmembrane segment and a single intracellular protein tyrosine phosphatase (PTPase) domain (see FIG. 1; see, also, SEQ ID NOS: 2 and 4, showing the amino acid sequences of a rabbit and a human GLEPP1, respectively). In addition, a mammalian GLEPP1 protein can contain a signal sequence or can be in a form in which the signal sequence has been cleaved. A mammalian GLEPP1 protein also can occur in a form that contains an additional functional region such as a tyrosine phosphorylation site (see FIG. 6, SEQ ID NO: 5) or in a form that contains fewer functional regions than a full length mammalian GLEPP1 protein (see, for example, FIG. 7, SEQ ID NO: 6, encoding a truncated human GLEPP1 protein that lacks a PTPase domain). A mammalian GLEPP1 protein that lacks a region that is otherwise present in a full length GLEPP1 protein can be identified, for example, by specific binding of the GLEPP1 protein with an anti-GLEPP1 antibody as described herein.

A mammalian GLEPP1 protein can be a phenotypic variant such as a polypeptide that is translated from an allelic variant of a GLEPP1 gene or a polypeptide that is the result of alternatively spliced GLEPP1 mRNA transcripts. For example, one form of an alternatively spliced rabbit GLEPP1 polypeptide does not contain amino acids 876 to 887 of SEQ ID NO: 2. Examples of human GLEPP1 polypeptides encoded by alternatively spliced nucleic acid sequences also are provided (see FIGS. 5, 6 and 7 SEQ ID NOS: 3, 5 and 6, respectively). Given the prevalence of alternatively spliced GLEPP1 polypeptides obtained by sequencing a limited number of cDNA clones, one in the art would expect that other alternatively spliced GLEPP1 proteins occur in a cell.

A GLEPP1 protein from a mammal other than a human or a rabbit can be recognized by having the characteristic structural domains described herein as well as by sharing amino acid sequence homology with a human and a rabbit GLEPP1 protein. For example, human and rabbit GLEPP1 have about a 96% sequence identity at the amino acid level and a greater than 90% sequence identity at the nucleotide level for the open reading frame. Methods for determining whether a putative GLEPP1 protein is related to a mammalian GLEPP1 protein are described in Example II. In addition, a sequence can be considered a mammalian GLEPP1 sequence if it has the activity of or encodes a polypeptide having the activity of a mammalian GLEPP1 protein. Methods for determining, for example, the PTPase activity of a mammalian GLEPP1 protein or a PTPase domain are described in Example III.

It is well known that various changes can be made to the amino acid and nucleotide sequences disclosed herein without significantly changing the secondary structure or the activity of the resultant mammalian GLEPP 1 protein. For example, nucleotide substitutions can be made in SEQ ID NOS: 1, 3, 5 and 6 without altering the translated amino acid sequence due to the degeneracy of the genetic code. Similarly, conservative amino acid substitutions can be made in SEQ ID NOS: 2 and 4 without altering the secondary structure or activity of the resultant polypeptide. Such modifications can be deliberate and introduced into a nucleotide sequence, for example, by site-directed mutagenesis or can be accidental such as occurs by mutation in a cell containing DNA encoding the polypeptide. In addition, deletions can occur naturally due, for example, to alternative splicing of an mRNA encoding a mammalian GLEPP1 protein. All such modified GLEPP1 amino acid and nucleic acid sequences are encompassed within scope of the invention, provided the encoded polypeptide maintains the general structural and functional characteristics of a mammalian GLEPP1 protein or PTPase domain as set forth herein.

The invention also provides isolated polypeptides comprising the amino acid sequence of the PTPase domain of a mammalian GLEPP1 protein. Such a polypeptide can comprise the intracellular domain of a mammalian GLEPP1 protein and, therefore, can exclude the extracellular and transmembrane region of GLEPP1 protein. Such a polypeptide having PTPase activity is an example of a mammalian GLEPP1 protein that is encompassed within the invention.

An advantage of an isolated PTPase domain of a mammalian GLEPP1 protein is that the PTPase domain can be soluble. Such a polypeptide can be used as soluble protein tyrosine phosphatase in an in vitro biochemical reaction. Examples of soluble polypeptides that comprise a PTPase domain having PTPase activity are polypeptides having the sequence of amino acids 888 to 1163 of SEQ ID NO: 2 or amino acids 889 to 1164 of SEQ ID NO: 4.

The polypeptides of the invention can be synthesized using an automated peptide synthesizer such as an Applied Biosystems Model 430A DNA synthesizer (Applied Biosystems, Foster City, Calif.). The polypeptides of the invention also can be produced by expressing a nucleic acid molecule that encodes a mammalian GLEPP1 protein or a PTPase domain of a mammalian GLEPP1 protein. Methods for expressing nucleic acids encoding the polypeptides of the invention are described below. In addition, active fragments of a GLEPP1 proteins such as a fragment comprising a PTPase domain can be obtained by biochemical methods such as partial enzymatic degradation of an isolated GLEPP1 protein followed by purification of the fragment containing PTPase activity.

An isolated mammalian GLEPP1 protein can be used as an immunogen for producing antibodies. Such antibodies, which can be polyclonal or monoclonal antibodies, are useful, for example, in methods of diagnosing the presence of a glomerular pathology in a subject. In addition, an antibody can be used to abrogate the activity of a GLEPP 1 protein such as the PTPase of the protein by binding, for example, to the active site of the PTPase. Methods for obtaining polyclonal and monoclonal antibodies are provided herein and otherwise known in the art (see, for example, Harlow and Lane, Antibodies: A laboratory manual, Cold Spring Harbor Laboratory, Cold Spring Harbor, New York, (1988) (incorporated herein by reference).

This invention is also directed to isolated nucleic acid sequences that encode a polypeptide comprising the sequence of a mammalian GLEPP1 protein or PTPase domain of a mammalian GLEPP1 protein, wherein the PTPase domain excludes the extracellular and transmembrane regions of a GLEPP1 protein. The invention provides, for example, a nucleic acid sequence encoding a rabbit GLEPP1 protein comprising nucleotides 180 to 3743 of SEQ ID NO: 1 or nucleotides 808 to 4374 of SEQ ID NO: 3. In addition, the invention provides a nucleic acid sequence encoding a PTPase domain of a mammalian GLEPP1 protein comprising, for example, nucleotides 2841 to 3670 of SEQ ID NO: 1 or nucleotides 3472 to 4299 of SEQ ID NO: 3. The invention also provides a nucleic acid sequence encoding a truncated GLEPP1 protein, which does not contain PTPase activity comprising, for example, nucleotides 808 to 3503 of SEQ ID NO: 5.

A nucleic acid sequence encodes a polypeptide if transcription of the nucleic acid molecule and translation of the resultant mRNA produce the polypeptide. Thus, the nucleic acid sequences of the invention include a nucleotide sequence such as a cDNA, which encodes a polypeptide directly, or a nucleotide sequence such as genomic DNA, which can contain, for example, introns that are spliced out following transcription of the gene. In addition, nucleic acid sequences comprising RNA such as an alternatively spliced RNA transcript are within the scope of the invention Such RNA sequences can be obtained from a cell using well known methods of RNA isolation (see Example IV) or can be obtained, for example, by cloning a corresponding DNA sequence in an appropriate vector that can express an RNA sequence. Such vectors are commercially available.

The nucleic acids of this invention also can be produced, for example, by synthetic methods using a commercial nucleic acid synthesizer or by PCR of a nucleic acid encoding a mammalian GLEPP1 protein. A nucleic acid sequence encoding a mammalian GLEPP1 can be identified by probing a cDNA library with a probe derived, for example, from rabbit GLEPP1 (SEQ ID NO: 1) or human GLEPP1 (SEQ ID NOS: 3, 5 and 6) DNA sequence (see Example V). In addition, a nucleic acid encoding a mammalian GLEPP1 can be identified by screening a cDNA expression library with an anti-GLEPP1 antibody (see Example I).

One skilled in the art would know that suitable conditions are required for screening a cDNA library. For example, when a library is screened using an oligonucleotide probe, the stringency of hybridization can be adjusted depending on the length of the probe and the degree of homology desired in an identified nucleic acid. Similarly, the conditions for screening an expression library with an antibody can be adjusted depending, for example, on the binding affinity of the antibody for a GLEPP1 protein. Methods for determining conditions suitable for screening a library are provided in Examples I and V and otherwise known in the art (see, for example, Sambrook et al., Molecular Cloning: A laboratory manual, Cold Spring Harbor Laboratory, Cold Spring Harbor, N.Y., (1989), which is incorporated herein by reference, and Harlow and Lane (1988).

The invention further is directed to expression vectors, which contain appropriate expression control elements that can be operatively linked to a nucleic acid sequence of the invention. Expression vectors are well known in the art and commercially available and include, for example, plasmid vectors and viral vectors. Expression control elements include, for example, appropriate transcription and translation start and stop sites, which can direct the transcription and translation of a nucleic acid sequence in an appropriate host cell. In some cases, it can be advantageous to include a tissue specific control element so as to restrict expression of a nucleic acid sequence to a particular cell type. A vector that expresses a mammalian GLEPP1 protein or a PTPase domain of a mammalian GLEPP1 protein in a particular cell type can be useful, for example, for treating a disease that is associated with improperly expressed GLEPP1. Expression vectors also can express RNA sequences, as discussed above, including, for example, antisense RNA sequences that can be used to abrogate the expression of GLEPP1 protein in a cell.

The invention also is directed to host cells, which can be prokaryotic or eukaryotic cells that can contain an expression vector of the invention and can express a mammalian GLEPP1 protein from the vector. Methods for inserting a DNA sequence into an expression vector, introducing the vector into a host cell and expressing the inserted DNA sequence in the host cell are well known in the art (see, for example, Sambrook et al. (1989).

The invention also is directed to nucleic acid probes that have a nucleotide sequence corresponding to a portion of a mammal GLEPP1 gene. Such probes can consist of synthetically produced oligonucleotides having at least ten nucleotides, wherein the ten nucleotides occur consecutively in a nucleic acid sequence encoding a mammalian GLEPP1 protein or can be, for example, restriction fragments of a nucleic acid sequence encoding a mammalian GLEPP1 protein. The probes of this invention are useful for detecting a nucleic acid sequence encoding a mammalian GLEPP1 protein. Such methods can include, for example, contacting a cDNA or genomic DNA library with the probe under stringent hybridization conditions and identifying molecules in the library that hybridize to the probe. Probes can be produced, for example, by chemical synthesis, by isolating restriction fragments and by amplifying a desired nucleic acid sequence using PCR. Such oligonucleotides also are useful as PCR primers and PCR can be used to identify the presence of a DNA sequence encoding a mammalian GLEPP1 or to amplify such a DNA sequence. Probes can be particularly useful when they are detectably labelled, which allows the amount of specific hybridization, for example, to be determined. Detectable labels are well known in the art and commercially available as are the methods for attaching the label to the probe.

An animal model of glomerular pathology indicated that GLEPP1 protein and GLEPP1 mRNA were markedly decreased as compared to normal levels expressed in glomerular cells. This sign also likely is associated with congenital nephrotic syndrome and minimal change nephrotic syndrome. Similarly, immunohistochemical analysis of kidney biopsies obtained from subjects suspected of having a glomerular pathology indicated, for example, that GLEPP1 protein is greatly reduced or absent in a subject having an inflammatory glomerular disease and indicated that the distribution of GLEPP1 on a cell is altered in a subject having minimal change glomerulonephropathy.

The invention provides methods for detecting the presence of a glomerular pathology in a subject by comparing, for example, the level of GLEPP1 mRNA or GLEPP1 protein expression or the pattern of distribution of GLEPP1 protein in a sample obtained from a subject with the level of GLEPP1 mRNA or protein expression or distribution of GLEPP1 protein in a control sample. As used herein, a "subject" means a mammal such as a human that is suspected of having a glomerular pathology characterized by altered expression of GLEPP1 protein or mRNA. An abnormally low level of GLEPP1 mRNA can indicate the presence of a glomerular pathology. As used herein, the term "sample" means, for example, a cell sample, which be present in a tissue sample obtained, for example, by kidney biopsy. A sample can consist of the whole cells or a tissue, which can be prepared for examination by immunohistochemical methods, or can consist of cells or a tissue that is processed so as to extract, for example, an isolated nucleic acid or protein fraction that can be analyzed. As used herein, the term "abnormally low level" refers to a level of GLEPP1 mRNA, or GLEPP1 protein that is less than the level expected in a normal sample. A normal level of GLEPP1 mRNA or protein expression can be determined by examining control samples, which are obtained from subjects that do not have or are not predisposed to having a glomerular pathology.

Method for identifying abnormally low mRNA levels can be performed by contacting an appropriate oligonucleotide probe with a nucleic acid sample to be analyzed. For example, a sample can be examined by northern blot analysis or RNAse protection analysis of podocyte mRNA using suitable hybridization conditions. Such suitable conditions are well known and include, for example, controlling the stringency of the hybridization reaction and the washing conditions. In addition, PCR analysis can be used to determine whether a sample obtained from a subject suspected of having a glomerular pathology contains an abnormally low level of GLEPP1 mRNA.

Certain genetic diseases affecting glomerular function can be identified by detecting defects in the GLEPP1 gene that result in decreased levels of GLEPP1 mRNA and GLEPP1 protein. Thus, the invention provides a method of detecting a subject that is at risk of having a glomerular pathology comprising identifying a defective GLEPP1 gene in the subject. A GLEPP1 gene can be defective due, for example, to the presence of an insertion, deletion or substitution in the gene. A defective GLEPP1 gene can be identified, for example, by detecting an abnormal pattern of restriction fragment migration following gel electrophoresis or by sequencing a part of gene suspected of being defective. The latter method can be performed by amplifying the suspected defective region of the gene using PCR, then sequencing the amplified product. Methods for restriction fragment mapping, PCR amplification and DNA sequencing are well known in the art.

The invention also provides methods that for preventing or reducing the severity of a glomerular pathology that is associated with an abnormally low level of GLEPP1 protein expression by introducing into a cell an expression vector containing a nucleic acid molecule encoding a mammalian GLEPP1 protein or a PTPase domain thereof. For example, the vector can be introduced into a subject and can be expressed in podocyte in order to provide a normal level of GLEPP1 protein expression in the cell.

Methods for introducing a vector into a mammalian cell and expressing a nucleic acid contained within the vector are well known to the art (see, for example, *Methods in*

*Enzymology*, vol. 185, Academic Press, Inc., San Diego, Calif. (D. V. Goeddel, ed.) (1990) or M. Krieger, *Gene Transfer and Expression: A laboratory manual*, Stockton Press, New York, N.Y., (1990), each of which is incorporated herein by reference). In general, viral-mediated transduction using a retrovirus or adenovirus vector is a preferred means of introducing a nucleic acid into a cell. Such vectors are particularly useful if they contain a control element that allows tissue specific expression of the nucleic acid in a cell such as a podocyte. A nucleic sequence encoding a mammalian GLEPP1 also can be introduced into a cell in a subject using liposome mediated methods.

The invention also provides anti-GLEPP1 antibodies, including polyclonal and monoclonal anti-GLEPP1 antibodies. As used herein, an "anti-GLEPP1 antibody" is an antibody that recognizes an epitope on a mammalian GLEPP1 protein. The antibodies and monoclonal antibodies of this invention are useful for detecting the presence of GLEPP1 protein in a sample or for abrogating the activity of a GLEPP1 protein. Anti-GLEPP1 antibodies can be raised by immunizing an animal with a naturally occurring or synthetic polypeptide of the invention or an antigenic fragment thereof. Methods of immunizing animals, isolating antibodies, and producing polyclonal or monoclonal antibodies are described herein and otherwise well known in the art (see, for example, by Harlow and Lane (1988)).

As discussed above, human and animal studies of glomerular pathology revealed that GLEPP1 protein expression was abnormally low or that GLEPP1 protein was redistributed in a subject having a glomerular pathology. Thus, the antibodies of the invention are useful for detecting the presence of a glomerular pathology in a subject. For example, a podocyte can be contacted with an anti-GLEPP1 antibody and the amount of specific binding of the antibody to the cell can indicate the level of GLEPP1 protein expression. As discussed previously, an abnormally low level of GLEPP1 protein expression on the podocyte can indicate that the subject has a glomerular pathology.

The method can be particularly useful as an in vivo diagnostic method to detect or follow the progress of a glomerular pathology. For example, an anti-GLEPP1 antibody can be labelled using technicium-99 and injected into a subject. The localization of the labelled antibody can be determined using well known imaging methods and the level and distribution of labelled antibody can be diagnostic of a glomerular pathology. In addition, the method can be used to follow the response of a subject to treatment by detecting a change in the amount of GLEPP1 protein expression following treatment.

The method also can be useful for detecting the presence of a glomerular pathology in a subject by examining a biopsy sample obtained from the subject. In the case, an anti-GLEPP1 antibody can be contacted with an appropriately prepared biopsy sample and the amount of antibody binding can be determined. The antibody can be labelled so as to be detectable or can be contacted with, for example, a labelled second antibody that is reactive the anti-GLEPP1 antibody. Detectable labels can include, for example, chemiluminescent agents, fluorescent moieties, radionuclides or enzymes. Alternatively, specific binding of an anti-GLEPP1 antibody to a GLEPP1 protein can be detected using a detectably labelled second antibody that is specific for the anti-GLEPP1 antibody (see Example I).

An altered distribution of GLEPP1 on the podocyte cell surface can be indicative of a glomerular pathology. For example, in normal glomerular tissue, most or all of the GLEPP1 protein is expressed on the podocyte surface that is in contact with the basement membrane. However, in an animal model of glomerular pathology significant amounts of GLEPP1 protein exist on parts of the cell surface not in contact with the basement membrane. Thus, another method of detecting a glomerular pathology involves determining the relative distribution of a mammalian GLEPP1 protein. A higher proportion of GLEPP1 on the podocyte surface not in contact with the basement membrane than in a normal control tissue can indicate the presence of a pathology.

The following Examples are intended to illustrate but not limit the invention.

EXAMPLE I

Immunohistochemical Characterization of GLEPP1

This example describes the preparation of monoclonal antibodies specific for GLEPP1 and the use of these antibodies to characterize GLEPP1 expression.

In order to identify podocyte-specific proteins, monoclonal antibodies (MAbs) were raised in mice immunized with isolated rabbit glomeruli. MAbs P8E7 and 4C3 were obtained from BALB/c mice immunized with isolated rabbit glomeruli (10,000 per immunization) using previously described methods (Goyal et al., *J. Am. Soc. Nephrol.* 1: 1334–1342 (1991), which is incorporated herein by reference). The resulting hybridomas were grown out in 96-well plates and selected and subcloned based on indirect immunofluorescence patterns on rabbit kidney sections.

MAbs were screened using indirect immunofluorescence on frozen sections of rabbit tissues. Two MAbs, P8E7 and 4C3, recognized a glomerular epithelial cell epitope. The epitope was extracellular as shown by binding of the MAbs to unpermeabilized isolated glomeruli. Using immunofluorescent analysis, GLEPP1 was not detectable by either MAb 4C3 or P8E7 in extra-glomerular renal cortex or medulla or in any other rabbit tissue examined, including brain, thyroid, thymus, lung, liver, spleen, skeletal muscle, heart, stomach, large intestine, small intestine, pancreas, salivary gland, testis, eye, inner ear and placenta. Thus, accessible GLEPP1 epitopes for MAb 4C3 and P8E7 are confined to the glomerulus and are present in a single epithelial cell type.

GLEPP1 was identified in glomeruli extracts by "western" blot analysis. Glomeruli were isolated from New Zealand White rabbits (2.0 to 2.5 kg) by iron oxide magnetization as previously described (Downer et al., *J. Clin. Invest.* 82: 998–1006 (1988), which is incorporated herein by reference). For glomerular extraction, $5 \times 10^4$ isolated glomeruli were suspended in 1 μl phosphate buffered saline containing 1% Triton X-100, 1% SDS, 2 mM phenylmethylsulfonyl fluoride, 5 mM N-ethylmaleimide, 2 mM EDTA and 8M urea. The sample was sonicated on ice4 using six 10 sec bursts as described previously by Goyal et al. (1991), which is incorporated herein by reference). Iron oxide and debris were removed by centrifugation and he supernatant was stored at −70 ° C.

Samples of glomerular extracts were analyzed by sodium dodecyl sulfate-polyacrylamide gel electrophoresis (SDS-PAGE) under reducing and non reducing conditions and western blotting (POLYBLOT® Model SBD-1000; American Bionetics, Hayward, Calif.). Following transfer of the proteins from the gel to the membrane and blocking of the membrane, the blots were incubated with primary IgG1 mouse monoclonal antibody (4C3 or P8E7) or a control MAb unreactive with rabbit (BB5). Following a washing step, blots were incubated with $^{125}$I-anti-mouse IgG and then exposed for autoradiography.

MAbs 4C3 and P8E7 both recognized a 235 kDa protein on a western blot of SDS/urea-extracted rabbit glomeruli under nonreducing conditions. Under reducing conditions, a band of about 205 kDa was recognized strongly by 4C3 and faintly by P8E7. In some glomerular extract preparations a variable proportion of the protein appears as a higher molecular weight form (approximately 300 kDa) under both reducing and nonreducing conditions.

Kidney tissue was analyzed by immunoperoxidase microscopy using the microwave method for immunoperoxidase staining. Kidney segments (1 mm) were microwaved in 0.5% glutaraldehyde as described by Login et al., *Lab. Invest.* 57: 585–591 (1987), which is incorporated herein by reference. Two μm tissue sections were prepared on a cryostat for subsequent analysis using the immunoperoxidase method according to Vector Laboratories (Burlingame, Calif.).

For the immunoperoxidase transmission electron microscopic studies, kidneys were perfuse-fixed with 4% paraformaldehyde and 10 μm sections were prepared using a cryostat. The sections were immunostained using the P8E7, 4C3 or the control BB5 MAbs and a peroxidase-labelled second antibody as described above. Sections were fixed with glutaraldehyde (2% in cacodylate buffer, pH 7.4), then imbedded in EPON and thin-sectioned using a diamond knife. Samples Were examined using a Phillips 400 electron microscope. Scanning electron microscopic studies were performed as previously described (Wiggins et al., *Lab. Invest.* 56: 264–272 (1987), which is incorporated herein by reference).

Immunoperoxidase electron microscopy studies showed that the epitope recognized by the MAbs was on the surface of visceral glomerular epithelial cells, predominantly on the urinary space aspect (non-glomerular basement membrane side) of foot processes. Less intense peroxidase deposit was observed on the cell bodies of epithelial cells. The distribution of GLEPP1 on the foot process surface appeared particulate, with each particle being about 30 nm in diameter and separated from its neighbor by about a 10 nm gap. Thus, GLEPP1 appears predominantly, but not exclusively, on podocyte foot processes in normal glomeruli.

EXAMPLE II

Isolation and Characterization of DNA Sequences Encoding GLEPP1 Protein and Characterization of the Derived GLEPP1 Amino Acid Sequence This example describes the isolation and characterization of a cDNA encoding rabbit GLEPP1 and the characterization of the derived GLEPP1 protein.

A rabbit glomerular cDNA library was constructed in λ-Uni-ZAP XR vector and screened with 4C3 MAb. Total RNA was prepared from isolated glomeruli by a modification of the cesium chloride/guanidinium isothiocyanate method of Chirgwin et al., *Biochemistry* 18: 5294–5299 (1979) as described by Merritt et al., *Lab. Invest.* 63: 762–769 (1990), each of which is incorporated herein by reference). Poly-A$^+$ RNA was isolated using oligo (dT) affinity chromatography and was used to construct a random primed directional cDNA expression library in λ-Uni-ZAP XR vector through the custom library service of Stratagene, Inc. (La Jolla, Calif.).

The cDNA library was screened using the 4C3 monoclonal antibody as described by Young et al. (In: *Genetic Engineering*, J. Setlow and A. Hollaender, eds. (New York: Plenum Publishing Corp.) 7: 29–41 (1985), which is incorporated herein by reference). Small cDNA inserts were rescued in pBluescript SK- phagemid using the in vivo excision protocol provided by the manufacturer (Stratagene). Larger cDNA inserts were isolated by restriction enzyme digestion and subcloned into pBluescript SK- using standard methods (Sambrook et al. (1989)). Double stranded DNA sequencing was performed by the dideoxy chain-termination method of Sanger et al. (*Proc. Natl. Acad. Sci. USA* 74: 5463–5467 (1977)) using the SEQUENASE® kit (United States Biochemical Corporation, Cleveland, Ohio) or the Taq TRACK® kit from Promega Corp (Madison, Wis.).

Two μg glomerular poly(A)$^+$ RNA was used to perform the 5' RACE method using a kit from GIBCO/BRL (Grand Island, N.Y.) according to the manufacturer's protocol. The PCR product was ligated into the pAMP vector (GIBCO/BRL) and transformed into DH5α competent cells. Other PCR products were ligated into the pCRII vector (Invitrogen, San Diego Calif.) and transformed into Invα competent cells (Invitrogen). Database searches were performed at the NCBI using the BLAST® network service for the "nonredundant" protein database which includes sequences from PDB, Swiss-Prot, PIR(R) and GenPept updates (Altschul et al., *J. Mol. Biol.* 215: 403–410 (1990)) and the FastA database including GenBank (6/93), EMBL (6/93) for nucleotides and SwissProt (4/93) for amino acid sequences and did not reveal any homologous protein or nucleic acid sequences except those encoding other PTPases as discussed below.

Thirteen positive cDNA clones were isolated and contained overlapping nucleotide sequence (FIG. 1). Additional cDNA clones were obtained by screening the library with the originally obtained GLEPP1 cDNA sequences and by PCR as indicated in FIG. 1. The rabbit GLEPP1 cDNA sequence spans 5,679 bp (SEQ ID NO: 1) and contains an open reading frame of 3,564 bp, which encodes a protein having 1,187 amino acids (SEQ ID NO: 2) (see FIG. 2). An initiator methionine (nucleotides 180 to 182) was identified by the following criteria: (a) the amino acid sequence was consistent with Kozak's consensus (first ATG in the open reading frame, G in the +4 position) (Kozak, M., *J. Cell Biol.* 108: 229–241 (1989)); (b) the initiator methionine was followed by a typical signal peptide, which contains 11 consecutive hydrophobic amino acids (LLPLLWLFVLL; SEQ ID NO: 7) (von Heijne, *Nucleic Acid Res.* 14: 4683–4690 (1986)). A stop codon was found at bp 3,742 to 3,744. Thus, assuming the putative signal peptide is cleaved during post-translational processing, the mature rabbit GLEPP1 protein contains 1,157 amino acids and has a phenylalanine at the N-terminus. A search of available databases using the FastA database (Pearson et al., *Proc. Natl. Acad. Sci. USA* 85: 2444–2448 (1988)) showed no identical nucleotide sequence previously published.

Analysis of the derived amino acid sequence by hydrophobicity plot revealed a single 25 amino acid hydrophobic sequence (819 to 843) compatible with a transmembrane region (see FIGS. 1 and 2). The C-terminal end of the putative transmembrane region contains positively charged amino acids (RKKH; SEQ ID NO: 8), which are typically found at the cytoplasmic side of a transmembrane region (Boyd et al., *Cell* 62: 1031–1033 (1990)). This molecular orientation relative to the cell membrane also is supported by binding studies using the 4C3 MAb, which binds to an epitope contained between amino acids 244 to 314 of the sequence shown in FIG. 1. Since the MAb 4C3 binds to non-permeabilized glomeruli, this epitope resides in the extracellular region of the GLEPP1 molecule. These results indicate that the region N-terminal to the transmembrane region is extracellular.

The 789 amino acids in the extracellular domain were analyzed for fibronectin type III-like repeats (FIG. 3). Eight such repeats were identified in the extracellular domain (see FIG. 1). The size of the repeats (approximately 100 residues) and the conserved amino acids were similar to those observed in the extracellular domains of two other membrane PTPases that contain a single PTPase domain (human PTPβ and Drosophila PTP10D). The N-terminal fibronectin type III repeat was more degenerate than those closer to the transmembrane region in all three PTPase receptors examined (GLEPP1, HPTPβ and DPTP10D). Analysis using the Genetics Computer Group Sequence Software Package (GCG, Madison Wis.) MOTIFS® program indicates that there are 15 potential N-linked glycosylation sites in the extracellular domain of GLEPP1.

The intracellular domain, comprising the C-terminus of GLEPP1 to the transmembrane region, contains a single typical 276 amino acid protein tyrosine phosphatase (PTPase) domain and a PTPase active site amino acid sequence, ((I/V)HCXAGXXR(S/T)G; SEQ ID NO: 9) (Trowbridge, J. Biol. Chem. 266: 23517–23520 (1991); Fischer et al., Science 253: 401–453 (1991)). The PTPase domain begins 45 amino acids C-terminal to the transmembrane region and extends from amino acid positions 888 to 1163 (see FIG. 2). Within the PTPase domain of the full length rabbit GLEPP1 protein are potential regulatory phosphorylation sites for casein kinase II (S 954, S 974, T 988) and protein kinase C (S 1, S 144).

Two of five cDNA clones examined were lacking 36 nucleotides (positions 2,804 to 2,839; SKNGLKKRKLTN; SEQ ID NO: 10) in the intracellular region immediately preceding the PTPase domain. The presence of two clones lacking this sequence indicates that variant GLEPP1 proteins due to alternative splicing exist in podocytes. The spliced-out lysine-rich region contains a potential phosphorylation site (T 886) for cAMP-dependent protein kinase.

The derived amino acid sequence of GLEPP1 PTPase domain was compared with that of two other members of the PTPase family, PTPβ and DPTP10D (a Drosophila CNS-specific PTPase), which are transmembrane receptors having a single type III membrane PTPase receptors as defined by Fischer et al. (1991). In addition, these PTPase sequences, which contain a single PTPase domain, also were compared with six members of a membrane PTPase family having tandem PTPase domains (human CD45, human PTPα, human PTPζ, human LAR, Drosophila PTP and Drosophila PTP99A) and with three members of the intracellular single domain PTP family (human T cell PTP, human PTP1β and human HePTP).

The single domain PTPases showed greater than 90% identity with each other (FIG. 4) but had less than 80% identity with the other PTPase sequences examined (not shown). The consensus amino acid residues present in the single domain type III PTPase receptors were similar to those previously described as being present in most PTPases (Kreuger et al., EMBO J. 9: 3241–3252 (1990), which is incorporated herein by reference). However, the three members of the type III receptor family shared 12 consensus amino acids which either were not present or were encountered only once in the 15 non-type III receptor PTPase sequences examined (both first and second domains of tandem domain PTPases were included in the analysis). In addition, two cysteine residues at positions 123 and 280, according to the numbering system used in FIG. 4, were present in the type III receptor PTPases but not in other PTPase sequences examined. Furthermore, a tryptophan residue was present at position 160 in all three type III receptor PTPases, whereas a tyrosine residue was present in 14 of the other 15 PTPase sequences examined. These results indicate that the type III receptor PTPase family contains specific amino acid residues within the PTPase domain that are characteristic for this type of receptor.

EXAMPLE III

Functional Analysis of GLEPP1

This example demonstrates the functional activity of GLEPP1 and various domains of GLEPP1 encoded by the isolated GLEPP1 cDNA.

To confirm that the PTPase domain has PTPase activity, a fragment of the GLEPP1 protein comprising the nucleotide sequence spanning from immediately 3' of the putative alternate splice site to the end of the coding region (positions 2,841 to 3,743; including the STOP codon), which contains 903 nucleotides encoding 300 amino acids (molecular weight 35 kDa) was cloned into the pGEX vector to form a fusion protein with glutathione S-transferase (Smith et al., Gene 67: 31–40 (1988); Guan et al., Anal. Biochem. 192: 262–267 (1991a), each of which is incorporated herein by reference). As a control, a nucleotide sequence encoding the part of the GLEPP1 extracellular domain (ECD) that is recognized by the 4C3 MAb (nucleotides 525 to 1,622), which contains 1098 nucleotides that encode 366 amino acids (molecular weight 42 kDa) also was cloned into the pGEX vector. The glutathione S-transferase protein alone (approximately 26 kDa) was expressed and used as an additional control.

Fusion proteins for the PTPase and extracellular domain were prepared using the expression vector, pGEX-KT, and a host cell, E. coli TG1. The GLEPP1 PTPase segment was amplified by PCR using the primers TTTGGATCCC CAGT-TCAACT GGATGACTTT (SEQ ID NO: 11) and TTTGAATTCC TAGGACTTGC TAACATTTTC (SEQ ID NO: 12). The extracellular segment was amplified using the primers TTTGGATCCA CAAAACCTCT ACCTGTAACC (SEQ ID NO: 13) and TTTGAATTCT TCAAGCCTCT GGCTCTCCTT (SEQ ID NO: 14).

The expression vector and the PCR products were digested with EcoRI and BamHI, then mixed together and the ligation mixtures were used to transform competent E. coli TG1. Fusion protein expression was performed as described by Smith et al. (1988) and fusion proteins were purified as described by Guan et al. (1991a). Since most of the ECD fusion protein was insoluble, this fraction was also extracted as described by Sambrook et al. (1989) prior to glutathione agarose affinity chromatography.

The expressed fusion proteins were purified by glutathione-sepharose affinity chromatography and examined for phosphatase and tyrosine phosphatase activity. Para-nitrophenyl phosphatase activity was assayed by the method of Tonks et al. (J. Biol. Chem. 263: 6731–6737 (1988), which is incorporated herein by reference), except that the reaction was carried out at 37° C. in 50 mM sodium acetate buffer (pH 5.5). Protein tyrosine phosphatase activity was assayed using the synthetic Raytide peptide (Oncogene Science, Manhasset, N.Y.) and the bovine myelin basic protein (Sigma, St. Louis, Mo.), each of which was labeled at the tyrosine residue using p60 C-SRC-protein tyrosine kinase (Oncogene Science, Manhasset, N.Y.) and [γ-$^{32}$p] ATP according to the Oncogene Science protocol. Labeled Raytide peptide was purified by adsorption to Whatman P81 filter paper and eluted with 500 mM ammonium carbonate and lyophilization as described by Guan et al. (*Nature* 350: 359–362 (1991b), which is incorporated herein by reference). Serine/threonine phosphatase activity was examined by phosphorylating dephosphorylated casein (Sigma) using the catalytic subunit of bovine heart cAMP-dependent protein kinase (Sigma) and [γ-$^{32}$P] ATP as described by Guan et al. (1991b). Phosphorylated casein and myelin basic protein were precipitated with ice cold trichloroacetic acid (TCA), washed three times with 20% TCA and the precipitates were dissolved in distilled water. Protein tyrosine phosphatase and serine/threonine phosphatase activities were assayed exactly as described by Streuli et al. (*Proc. Natl. Acad. Sci. USA.* 86: 8698–8702 (1989), which is incorporated herein by reference).

The affinity-purified PTPase fusion protein, which had the expected molecular weight of about 60 kDa by SDS-PAGE, had p-nitrophenyl phosphatase activity and tyrosine phosphatase activity the two $^{32}$P-tyrosine phosphorylated substrates, myelin basic protein and the Raytide peptide. The pH optimum of the PTPase fusion protein for the p-nitrophenyl phosphate substrate was pH 5.5 and the pH optimum for the tyrosine phosphorylated protein substrates was pH 7.0. The PTPase fusion protein showed no detectable serine/threonine phosphatase activity when tested against $^{32}$P-casein, which had been labeled with γ$^{32}$P-ATP in the presence of the catalytic subunit of cyclic AMP-dependent protein kinase. The purified glutathione S-transferase, alone, and the purified ECD fusion protein did not demonstrate p-nitrophenyl phosphatase or tyrosine phosphatase activities. These results confirm that the PTPase domain acts as a protein tyrosine phosphatase but not as a serine/threonine phosphatase under the conditions tested.

The affinity-purified GLEPP1 ECD fusion protein (encoded by nucleotides 525 to 1,622) was examined by western blot analysis using the 4C3 MAb as a probe. A band was seen corresponding to the expected molecular weight of the ECD fusion protein at about 70 kDa. No band was seen on the same western blot with the purified glutathione S-transferase protein or the purified PTPase fusion protein.

The affinity-purified ECD fusion protein was used to immunize a guinea pig. Polyclonal antiserum produced by the guinea pig was tested by indirect immunofluorescence against rabbit renal cortex. The polyclonal antiserum specifically stained glomerular epithelial cells and showed an immunofluorescence pattern that was identical to the pattern observed for the original GLEPP1 MAbs, 4C3 and P8E7. Thus, the cloned ECD nucleotide sequence comprising nucleotides 525 to 1,622 of SEQ ID NO: 1 encodes a protein having the same distribution as GLEPP1 on the basis of 4C3 and P8E7 MAbs. These results also confirm that the putative open reading frame is correct and in the appropriate orientation.

EXAMPLE IV

GLEPP1 mRNA EXPRESSION

This example demonstrates that GLEPP1 mRNA is expressed primarily in podocytes in the kidney glomerulus but also is expressed in a low level in brain.

Northern blot analysis of RNA from renal cortex was performed as follows. cDNA fragments were labeled with $^{32}$P-dCTP using a random primer DNA labeling kit (Boehringer Mannheim Biochemicals, Indianapolis, Ind.). Forty μg renal cortical RNA per lane were used for northern blots. Controls to determine loading and transfer of RNA were determined by methylene blue staining of blots. Prehybridization, hybridization and washings were carried out as described by Sambrook et al. (1989). Conditions for the stringent final wash of the northern blot were 0.1 x SSC at 65° C.

Northern blot analysis was performed using RNA obtained from glomerulus, renal cortex, liver, brain, lung, heart, spleen, testis, stomach, small intestine and large intestine. GLEPP1 mRNA was detected only in glomeruli, which expressed a high level, and renal cortex, which expressed a lower level, presumably due to the presence of glomeruli in the sample (not shown). The position of migration of the single transcript indicated the GLEPP1 mRNA was approximately 6 kilobases in size. In addition, RNAse protection assays were performed on the RNA samples obtained as described above. Using RNAse protection, a faint GLEPP1 mRNA was detected in an RNA sample isolated from brain (not shown).

These results indicate that GLEPP1 mRNA is primarily expressed in kidney glomeruli, although, to a much lesser extent, GLEPP1 mRNA also is expressed in brain. Since GLEPP1 protein was not detected in brain tissue using histochemical methods, the GLEPP1 epitope in brain cells may be inaccessible to the antibody.

EXAMPLE V

Isolation and Characterization of Nucleic Acid Sequences Encoding Human GLEPP1 Proteins and Characterization of the Derived Amino Acid Sequences This example describes the isolation and characterization of cDNA clones encoding human GLEPP1 proteins and the characterization of the derived amino acid sequences of the human GLEPP1 proteins.

Nucleic acid probes prepared from the cDNA encoding rabbit GLEPP1, as described above, were used to screen a human kidney cDNA library. Positive clones were selected and the cDNA inserts were sequenced as described above. Overlapping sequences were identified and used to determine that the cloned cDNA inserts encoded three different human GLEPP1 proteins (FIGS. 5 to 7).

FIG. 5 shows the nucleic acid sequence (SEQ ID NO: 3) and derived amino acid sequence (SEQ ID NO: 4) of a human GLEPP1 protein. Nucleotide positions 808 to 4374 define an open reading frame (STOP codon, TAG, 4372–4374), which encodes a human GLEPP1 protein that contains 1188 amino acids (SEQ ID NO: 4) and shares about 96% sequence identity with the rabbit GLEPP1 protein (SEQ ID NO: 2). The PTPase domain in this human GLEPP1 protein extends from amino acid positions 888 to 1164 (SEQ ID NO: 4). This human GLEPP1 variant also contains a cyclic AMP-dependent phosphorylation consensus sequence similar to that observed in the rabbit GLEPP1 protein.

FIG. 6 shows the cDNA sequence of an alternatively spliced nucleic acid encoding a human GLEPP1 protein (SEQ ID NO: 5). As a result of the alternative splicing event, the human GLEPP1 protein of SEQ ID NO: 5 contains additional nucleotides at position 3445 to 3497 (indicated in lowercase letters in FIG. 6). The open reading frame extends from nucleotide 808 to 4437 (STOP codon, TAG, 4435–4437) and encodes a 1209 amino acid human GLEPP1 protein. This splice variant does not contain a cyclic AMP-dependent phosphorylation site but, instead, contains a tyrosine phosphorylation consensus sequence.

In addition, a nucleotide sequence encoding a truncated human GLEPP1 splice variant was cloned (FIG. 7; SEQ ID NO: 6.). The nucleic acid sequence encoding the variant truncated human GLEPP1 protein is identical to the nucleic acid sequence shown in FIG. 5 from positions 1 to 3554, then varies as indicated by the nucleotides shown in lower case. The open reading frame terminates at a STOP codon at nucleotides 3604 to 3606 (TGA), resulting in a human GLEPP1 protein having 932 amino acids. This human GLEPP1 variant does not have a PTPase domain.

These results indicate that the nucleic acid sequences encoding human and rabbit GLEPP1 proteins are highly homologous and that mammalian GLEPP1 proteins are highly conserved. In addition, these results indicate that mammalian GLEPP1 proteins exist in several different variant forms in mammalian cells.

Although the invention has been described with reference to the examples, it should be understood that various modifications can be made without departing from the spirit of the invention. Accordingly, the invention is limited only by the following claims.

---

We claim:

1. An isolated nucleic acid sequence encoding a mammalian glomerular epithelial protein 1 (GLEPP1) polypeptide or a PTPase domain of a mammalian GLEPP1 protein, provided said nucleic acid sequence is not isolated from a nucleic acid molecule obtained from rabbit glomerulus.

2. The nucleic acid sequence of claim 1, wherein said GLEPP1 protein is human GLEPP1.

3. The nucleic acid sequence of claim 2 comprising nucleotides 808 to 4374 shown in FIG. 5 (SEQ ID NO: 3).

4. The nucleic acid sequence of claim 2, comprising nucleotides 3472 to 4299 shown in FIG. 5 (SEQ ID NO: 3).

5. The nucleic acid sequence of claim 2, comprising nucleotides 808 to 4437 shown in FIG. 6 (SEQ ID NO: 5).

6. The nucleic acid sequence of claim 2, comprising nucleotides 808 to 3606 shown in FIG. 7 (SEQ ID NO: 6).

7. The nucleic acid sequence of claim 2, encoding amino acids 1 to 1188 as shown in FIG. 5 (SEQ ID NO: 4).

8. The nucleic acid sequence of claim 2, encoding amino acids 888 to 1164 as shown in FIG. 5 (SEQ ID NO: 4).

* * * * *

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 5679 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 180..3740

( x i ) SEQUENCE DESCRIPTION: SEQ ID NO:1:

```
CGGCACGAGG  GAGGACAGGG  AGACGGCGCA  GGGGGACTGA  AAAGGCAGCA  TGCGACCGCC      60

GGGAGCAGCT  TCGGCGCCCA  CCGTCTGAGG  CTGCAGCCCC  AGTTCGCCTT  TGTGAGCGGC     120

CGCCTGGGAA  GCCCGCCAGC  CCCGCNGTGC  CCCACTCCCG  GGTTCCCGTT  CGCTCTGCG     179

ATG  GGG  CAC  CTG  CCC  ACC  AGG  GCG  CGC  GGC  CGC  CGC  CGC  CTG  CTG  CCT     227
Met  Gly  His  Leu  Pro  Thr  Arg  Ala  Arg  Gly  Arg  Arg  Arg  Leu  Leu  Pro
 1              5                   10                  15

CTG  CTC  TGG  CTC  TTT  GTG  CTG  CTC  AAG  ACT  GCT  GCA  GCC  TTC  CAC  GTA     275
Leu  Leu  Trp  Leu  Phe  Val  Leu  Leu  Lys  Thr  Ala  Ala  Ala  Phe  His  Val
             20                  25                  30

ACA  GTC  CGA  GAT  GAC  AAC  AGC  ATT  GTT  GTC  TCT  CTG  GAA  GCC  TCC  GAT     323
Thr  Val  Arg  Asp  Asp  Asn  Ser  Ile  Val  Val  Ser  Leu  Glu  Ala  Ser  Asp
         35                  40                  45

GTC  ATC  AGT  CCA  GCA  TCT  GTG  TAT  GTT  GTG  AAG  ATA  ACT  GGT  GAA  TCC     371
Val  Ile  Ser  Pro  Ala  Ser  Val  Tyr  Val  Val  Lys  Ile  Thr  Gly  Glu  Ser
     50                  55                  60

AAA  AAT  TAT  TTC  TTC  GAA  TTT  GAG  GAA  TTC  AAC  AGC  ACT  TTG  CCT  CCT     419
Lys  Asn  Tyr  Phe  Phe  Glu  Phe  Glu  Glu  Phe  Asn  Ser  Thr  Leu  Pro  Pro
 65                  70                  75                  80

CCT  GTT  ATC  TTT  AAG  GCC  AAT  TAT  CAT  GGC  CTT  TAT  TAC  ATT  ATC  ACC     467
Pro  Val  Ile  Phe  Lys  Ala  Asn  Tyr  His  Gly  Leu  Tyr  Tyr  Ile  Ile  Thr
                 85                  90                  95

CTG  GTG  GTG  GTA  AAT  GGA  AAT  GTG  GTT  ACC  AAG  CCA  TCC  AGA  TCT  ATC     515
Leu  Val  Val  Val  Asn  Gly  Asn  Val  Val  Thr  Lys  Pro  Ser  Arg  Ser  Ile
                100                 105                 110

ACT  GTG  TTA  ACA  AAA  CCT  CTA  CCT  GTA  ACC  AGT  GTT  TCA  ATA  TAT  GAC     563
Thr  Val  Leu  Thr  Lys  Pro  Leu  Pro  Val  Thr  Ser  Val  Ser  Ile  Tyr  Asp
```

-continued

| | 115 | | | | 120 | | | | | 125 | | | | |
|---|---|---|---|---|---|---|---|---|---|---|---|---|---|---|
| TAT | AAG | CCT | TCT | CCT | GAA | ACA | GGA | GTC | TTG | TTT | GAA | ATT | CAT | TAT | CCA | 611 |
| Tyr | Lys | Pro | Ser | Pro | Glu | Thr | Gly | Val | Leu | Phe | Glu | Ile | His | Tyr | Pro | |
| | 130 | | | | 135 | | | | | 140 | | | | | | |

| GAA | AAA | TAT | AAT | GTT | TTC | ACA | AGA | GTG | AAC | ATA | AGC | TAC | TGG | GAA | GGG | 659 |
| Glu | Lys | Tyr | Asn | Val | Phe | Thr | Arg | Val | Asn | Ile | Ser | Tyr | Trp | Glu | Gly | |
| 145 | | | | | 150 | | | | | 155 | | | | | 160 | |

| AAA | GCC | TTC | CGG | ACA | ATG | CTG | TAC | AAA | GAT | TTC | TTT | AAG | GGA | AAA | ACA | 707 |
| Lys | Ala | Phe | Arg | Thr | Met | Leu | Tyr | Lys | Asp | Phe | Phe | Lys | Gly | Lys | Thr | |
| | | | | | 165 | | | | 170 | | | | | 175 | | |

| GTA | TTT | AAT | CAC | TGG | CTG | CCA | GGA | ATA | TGT | TAT | AGT | AAT | ATC | ACC | TTT | 755 |
| Val | Phe | Asn | His | Trp | Leu | Pro | Gly | Ile | Cys | Tyr | Ser | Asn | Ile | Thr | Phe | |
| | | | 180 | | | | | 185 | | | | | 190 | | | |

| CAG | CTG | GTT | TCT | GAG | GCA | ACT | TTT | AAT | AAA | AGT | ACC | CTT | GTG | GAG | TAC | 803 |
| Gln | Leu | Val | Ser | Glu | Ala | Thr | Phe | Asn | Lys | Ser | Thr | Leu | Val | Glu | Tyr | |
| | | 195 | | | | | 200 | | | | | 205 | | | | |

| AGT | GGT | GTC | AGC | CAT | GAA | CCG | AAG | CAG | CAC | AGA | ACT | GCT | CCT | TAT | CCA | 851 |
| Ser | Gly | Val | Ser | His | Glu | Pro | Lys | Gln | His | Arg | Thr | Ala | Pro | Tyr | Pro | |
| | 210 | | | | | 215 | | | | | 220 | | | | | |

| CCT | CGA | AAT | ATT | TCT | GTT | CGA | ATT | GTA | AAC | TTG | AAC | AAA | AAC | AAC | TGG | 899 |
| Pro | Arg | Asn | Ile | Ser | Val | Arg | Ile | Val | Asn | Leu | Asn | Lys | Asn | Asn | Trp | |
| 225 | | | | | 230 | | | | | 235 | | | | | 240 | |

| GAA | GAA | CAG | AGT | GGC | AGT | TTC | CCA | GAG | GAA | TCA | TTC | ATG | AGA | TCA | CCA | 947 |
| Glu | Glu | Gln | Ser | Gly | Ser | Phe | Pro | Glu | Glu | Ser | Phe | Met | Arg | Ser | Pro | |
| | | | | 245 | | | | | 250 | | | | | 255 | | |

| GAA | ACA | ATA | GAA | AAA | GAC | AGA | ATC | TTC | CAT | TTT | ACA | GAG | GAA | ACT | CCT | 995 |
| Glu | Thr | Ile | Glu | Lys | Asp | Arg | Ile | Phe | His | Phe | Thr | Glu | Glu | Thr | Pro | |
| | | | 260 | | | | | 265 | | | | | 270 | | | |

| GAG | CCA | TCT | GGA | AAC | ATT | TCT | TCT | GGT | TGG | CCT | GAT | TTT | AAT | AGC | AGT | 1043 |
| Glu | Pro | Ser | Gly | Asn | Ile | Ser | Ser | Gly | Trp | Pro | Asp | Phe | Asn | Ser | Ser | |
| | | 275 | | | | | 280 | | | | | 285 | | | | |

| GAC | TAT | GAA | ACT | ACG | TCT | CAG | CCA | TAT | TGG | TGG | GAC | AGC | GCA | TCT | GCA | 1091 |
| Asp | Tyr | Glu | Thr | Thr | Ser | Gln | Pro | Tyr | Trp | Trp | Asp | Ser | Ala | Ser | Ala | |
| | 290 | | | | | 295 | | | | | 300 | | | | | |

| ACT | CCT | GAA | AGT | GAA | GAT | GAA | TTT | GTC | AGT | GTA | CTT | CCC | ATG | GAA | TAC | 1139 |
| Thr | Pro | Glu | Ser | Glu | Asp | Glu | Phe | Val | Ser | Val | Leu | Pro | Met | Glu | Tyr | |
| 305 | | | | | 310 | | | | | 315 | | | | | 320 | |

| GAA | AAT | AAC | AAT | ACA | CTC | AGT | GAG | GCT | GAG | AAG | CCC | ACA | CCA | GCC | CCT | 1187 |
| Glu | Asn | Asn | Asn | Thr | Leu | Ser | Glu | Ala | Glu | Lys | Pro | Thr | Pro | Ala | Pro | |
| | | | | 325 | | | | | 330 | | | | | 335 | | |

| TTC | TCT | TTC | TTC | CCT | GTG | CAA | ATG | ATA | TTG | AGC | TGG | CTA | CCC | CCA | AAA | 1235 |
| Phe | Ser | Phe | Phe | Pro | Val | Gln | Met | Ile | Leu | Ser | Trp | Leu | Pro | Pro | Lys | |
| | | | 340 | | | | | 345 | | | | | 350 | | | |

| CCC | CCC | ACT | GCC | TTT | GAT | GGG | TTC | CAT | ATT | CAC | ATA | GAG | AGA | GAA | GAG | 1283 |
| Pro | Pro | Thr | Ala | Phe | Asp | Gly | Phe | His | Ile | His | Ile | Glu | Arg | Glu | Glu | |
| | | 355 | | | | | 360 | | | | | 365 | | | | |

| AAC | TTC | ACT | GAA | TAT | TCG | ACA | GTG | GAT | GAA | GAG | GCG | CAT | GAA | TTT | GTT | 1331 |
| Asn | Phe | Thr | Glu | Tyr | Ser | Thr | Val | Asp | Glu | Glu | Ala | His | Glu | Phe | Val | |
| | 370 | | | | | 375 | | | | | 380 | | | | | |

| GCA | GAA | CTC | AAG | GAG | CCC | GGG | AAA | TAC | AAG | TTA | TCT | GTG | ACA | ACC | TTT | 1379 |
| Ala | Glu | Leu | Lys | Glu | Pro | Gly | Lys | Tyr | Lys | Leu | Ser | Val | Thr | Thr | Phe | |
| 385 | | | | | 390 | | | | | 395 | | | | | 400 | |

| AGT | GCC | TCA | GGA | TCT | TGC | GAA | ACT | CGA | GAA | AGT | CAG | TCA | GCA | AAA | TCA | 1427 |
| Ser | Ala | Ser | Gly | Ser | Cys | Glu | Thr | Arg | Glu | Ser | Gln | Ser | Ala | Lys | Ser | |
| | | | | 405 | | | | | 410 | | | | | 415 | | |

| CTA | AGC | TTT | TAT | ATC | AGT | CCT | ACA | GGA | GAG | TGG | ATT | GAA | GAG | CTG | ACA | 1475 |
| Leu | Ser | Phe | Tyr | Ile | Ser | Pro | Thr | Gly | Glu | Trp | Ile | Glu | Glu | Leu | Thr | |
| | | | 420 | | | | | 425 | | | | | 430 | | | |

| GAG | AAG | CCC | CAG | CAT | GTG | AGC | GTC | CAT | GTT | TTA | AGC | TCG | ACC | ACT | GCT | 1523 |
| Glu | Lys | Pro | Gln | His | Val | Ser | Val | His | Val | Leu | Ser | Ser | Thr | Thr | Ala | |

|     |     |     |     |     |     |     |     |     |     |     |     |     |     |     |     |      |
|---|---|---|---|---|---|---|---|---|---|---|---|---|---|---|---|---|
| | | | | 435 | | | | | 440 | | | | | 445 | | |
| TTG | ATG | TCC | TGG | ACA | TCT | TCC | CAG | GAG | AAC | TAT | AAC | AGC | ACC | ATT | GTG | 1571 |
| Leu | Met | Ser | Trp | Thr | Ser | Ser | Gln | Glu | Asn | Tyr | Asn | Ser | Thr | Ile | Val | |
| | 450 | | | | | 455 | | | | | 460 | | | | | |
| TCT | GTG | GTG | TCA | CTG | ACC | TGC | CAG | AAA | CAA | AAG | GAG | AGC | CAG | AGG | CTT | 1619 |
| Ser | Val | Val | Ser | Leu | Thr | Cys | Gln | Lys | Gln | Lys | Glu | Ser | Gln | Arg | Leu | |
| 465 | | | | | 470 | | | | | 475 | | | | | 480 | |
| GAA | AAG | CAG | TAC | TGT | ACA | CAG | GTG | AAC | TCA | AGC | AAA | CGT | ATT | ATT | GAA | 1667 |
| Glu | Lys | Gln | Tyr | Cys | Thr | Gln | Val | Asn | Ser | Ser | Lys | Arg | Ile | Ile | Glu | |
| | | | | 485 | | | | | 490 | | | | | 495 | | |
| AAT | CTG | GTT | CCT | GGT | GCC | CAG | TAC | CAG | GTT | GTG | ATG | TAC | CTA | AGA | AAA | 1715 |
| Asn | Leu | Val | Pro | Gly | Ala | Gln | Tyr | Gln | Val | Val | Met | Tyr | Leu | Arg | Lys | |
| | | | 500 | | | | | 505 | | | | | 510 | | | |
| GGC | CCT | CTG | ATT | GGA | CCA | CCT | TCA | GAT | CCT | GTG | ACA | TTT | GCC | ATT | GTG | 1763 |
| Gly | Pro | Leu | Ile | Gly | Pro | Pro | Ser | Asp | Pro | Val | Thr | Phe | Ala | Ile | Val | |
| | | 515 | | | | | 520 | | | | | 525 | | | | |
| CCC | ACT | GGA | ATA | AAG | GAC | TTA | ATG | CTT | TAT | CCC | TTG | GGT | CCT | ACA | GCA | 1811 |
| Pro | Thr | Gly | Ile | Lys | Asp | Leu | Met | Leu | Tyr | Pro | Leu | Gly | Pro | Thr | Ala | |
| | 530 | | | | | 535 | | | | | 540 | | | | | |
| GTG | GTT | CTG | AGC | TGG | ACC | AGA | CCT | TAC | CTA | GGA | GTG | TTC | AGA | AAA | TAC | 1859 |
| Val | Val | Leu | Ser | Trp | Thr | Arg | Pro | Tyr | Leu | Gly | Val | Phe | Arg | Lys | Tyr | |
| 545 | | | | | 550 | | | | | 555 | | | | | 560 | |
| GTG | GTT | GAA | ATG | TTT | TAT | TTC | AAC | CCT | GCA | ACT | ATG | ACA | TCT | GAG | TGG | 1907 |
| Val | Val | Glu | Met | Phe | Tyr | Phe | Asn | Pro | Ala | Thr | Met | Thr | Ser | Glu | Trp | |
| | | | | 565 | | | | | 570 | | | | | 575 | | |
| ACC | ACC | TAC | TAT | GAA | ATA | GCC | GCA | ACT | GTC | TCC | TTA | ACT | GCT | TCC | GTG | 1955 |
| Thr | Thr | Tyr | Tyr | Glu | Ile | Ala | Ala | Thr | Val | Ser | Leu | Thr | Ala | Ser | Val | |
| | | | 580 | | | | | 585 | | | | | 590 | | | |
| AGA | ATA | GCT | AAT | CTG | TTG | CCA | GCA | TGG | TAC | TAC | AAC | TTT | CGG | GTA | ACC | 2003 |
| Arg | Ile | Ala | Asn | Leu | Leu | Pro | Ala | Trp | Tyr | Tyr | Asn | Phe | Arg | Val | Thr | |
| | | 595 | | | | | 600 | | | | | 605 | | | | |
| ATG | GTG | ACA | TGG | GGA | GAT | CCA | GAA | CTG | AGC | TGT | TGT | GAC | AGT | TCC | ACC | 2051 |
| Met | Val | Thr | Trp | Gly | Asp | Pro | Glu | Leu | Ser | Cys | Cys | Asp | Ser | Ser | Thr | |
| | 610 | | | | | 615 | | | | | 620 | | | | | |
| ATA | AGC | TTC | ATC | ACA | GCC | CCA | GTA | GCT | CCA | GAA | ATC | ACT | TCT | GTG | GAA | 2099 |
| Ile | Ser | Phe | Ile | Thr | Ala | Pro | Val | Ala | Pro | Glu | Ile | Thr | Ser | Val | Glu | |
| 625 | | | | | 630 | | | | | 635 | | | | | 640 | |
| TAT | TTC | AAC | AGC | CTG | CTA | TAT | ATC | AGC | TGG | ACA | TAT | GGG | GAC | GAC | ACA | 2147 |
| Tyr | Phe | Asn | Ser | Leu | Leu | Tyr | Ile | Ser | Trp | Thr | Tyr | Gly | Asp | Asp | Thr | |
| | | | | 645 | | | | | 650 | | | | | 655 | | |
| ACA | GAC | CTG | TCA | CAT | TCT | AGA | ATG | CTA | CAC | TGG | ATG | GTT | GTA | GCA | GAA | 2195 |
| Thr | Asp | Leu | Ser | His | Ser | Arg | Met | Leu | His | Trp | Met | Val | Val | Ala | Glu | |
| | | | 660 | | | | | 665 | | | | | 670 | | | |
| GGA | AAG | AAG | AAA | ATT | AAA | AAG | AGT | GTA | ACA | CGC | AAT | GTC | ATG | ACC | GCA | 2243 |
| Gly | Lys | Lys | Lys | Ile | Lys | Lys | Ser | Val | Thr | Arg | Asn | Val | Met | Thr | Ala | |
| | | 675 | | | | | 680 | | | | | 685 | | | | |
| ATT | CTC | AGC | TTG | CCT | CCA | GGA | GAC | ATC | TAC | AAC | CTT | TCA | GTA | ACT | GCT | 2291 |
| Ile | Leu | Ser | Leu | Pro | Pro | Gly | Asp | Ile | Tyr | Asn | Leu | Ser | Val | Thr | Ala | |
| | 690 | | | | | 695 | | | | | 700 | | | | | |
| TGC | ACG | GAA | AGA | GGA | AGT | AAT | ACC | TCC | ATG | CTC | CGC | CTT | GTC | AAG | CTA | 2339 |
| Cys | Thr | Glu | Arg | Gly | Ser | Asn | Thr | Ser | Met | Leu | Arg | Leu | Val | Lys | Leu | |
| 705 | | | | | 710 | | | | | 715 | | | | | 720 | |
| GAA | CCA | GCT | CCT | CCA | AAA | TCA | CTC | TTT | GCA | GTG | AAC | AAA | ACT | CAG | ACT | 2387 |
| Glu | Pro | Ala | Pro | Pro | Lys | Ser | Leu | Phe | Ala | Val | Asn | Lys | Thr | Gln | Thr | |
| | | | | 725 | | | | | 730 | | | | | 735 | | |
| TCA | GTG | ACT | CTG | CTG | TGG | GTG | GAA | GAG | GGC | GTA | GCT | GAT | TTC | TTC | GAA | 2435 |
| Ser | Val | Thr | Leu | Leu | Trp | Val | Glu | Glu | Gly | Val | Ala | Asp | Phe | Phe | Glu | |
| | | | 740 | | | | | 745 | | | | | 750 | | | |
| GTC | TTC | TGT | CAA | CAA | GTT | GGC | TCT | GGT | CTG | GAA | ACC | AAA | CTC | CAG | GAG | 2483 |
| Val | Phe | Cys | Gln | Gln | Val | Gly | Ser | Gly | Leu | Glu | Thr | Lys | Leu | Gln | Glu | |

|  |  |  |  |  |  |  |  |  |  |  |  |  |  |  |  |  |
|---|---|---|---|---|---|---|---|---|---|---|---|---|---|---|---|---|
|  | 755 |  |  |  |  | 760 |  |  |  |  | 765 |  |  |  |  |  |
| CCA | GTT | GCT | GTT | TCT | TCT | CAT | GTT | GTG | ACC | ATC | TCT | AGT | CTC | CTT | CCA | 2531 |
| Pro | Val | Ala | Val | Ser | Ser | His | Val | Val | Thr | Ile | Ser | Ser | Leu | Leu | Pro |  |
|  | 770 |  |  |  | 775 |  |  |  |  | 780 |  |  |  |  |  |  |
| GCC | ACT | GCT | TAC | AAC | TGT | AGT | GTC | ACC | AGC | TTT | AGC | CAC | GAC | AGC | CCC | 2579 |
| Ala | Thr | Ala | Tyr | Asn | Cys | Ser | Val | Thr | Ser | Phe | Ser | His | Asp | Ser | Pro |  |
| 785 |  |  |  | 790 |  |  |  |  | 795 |  |  |  |  | 800 |  |  |
| AGT | GTT | CCT | ACA | TTT | ATA | GCT | GTC | TCA | ACA | ATG | GTT | ACA | GAG | ATG | AAC | 2627 |
| Ser | Val | Pro | Thr | Phe | Ile | Ala | Val | Ser | Thr | Met | Val | Thr | Glu | Met | Asn |  |
|  |  |  |  | 805 |  |  |  |  | 810 |  |  |  |  | 815 |  |  |
| CCT | AAC | GTG | GTA | GTA | ATC | TCA | GTG | CTG | GCC | ATC | CTT | AGC | ACA | CTT | CTA | 2675 |
| Pro | Asn | Val | Val | Val | Ile | Ser | Val | Leu | Ala | Ile | Leu | Ser | Thr | Leu | Leu |  |
|  |  |  | 820 |  |  |  |  | 825 |  |  |  |  | 830 |  |  |  |
| ATT | GGT | CTG | CTG | CTT | GTT | ACT | CTC | ATC | ATT | CTT | AGG | AAG | AAA | CAT | CTG | 2723 |
| Ile | Gly | Leu | Leu | Leu | Val | Thr | Leu | Ile | Ile | Leu | Arg | Lys | Lys | His | Leu |  |
|  |  | 835 |  |  |  |  | 840 |  |  |  |  | 845 |  |  |  |  |
| CAG | ATG | GCT | AGG | GAG | TGT | GGA | GCA | GGA | ACA | TTT | GTC | AAT | TTT | GCA | TCT | 2771 |
| Gln | Met | Ala | Arg | Glu | Cys | Gly | Ala | Gly | Thr | Phe | Val | Asn | Phe | Ala | Ser |  |
|  | 850 |  |  |  | 855 |  |  |  |  | 860 |  |  |  |  |  |  |
| TTA | GAG | AGG | GAT | GGA | AAG | CTT | CCC | TAC | AAC | TGG | AGT | AAA | AAT | GGC | TTA | 2819 |
| Leu | Glu | Arg | Asp | Gly | Lys | Leu | Pro | Tyr | Asn | Trp | Ser | Lys | Asn | Gly | Leu |  |
| 865 |  |  |  | 870 |  |  |  |  | 875 |  |  |  |  | 880 |  |  |
| AAG | AAG | AGG | AAA | CTA | ACT | AAC | CCA | GTT | CAA | CTG | GAT | GAC | TTT | GAT | GCT | 2867 |
| Lys | Lys | Arg | Lys | Leu | Thr | Asn | Pro | Val | Gln | Leu | Asp | Asp | Phe | Asp | Ala |  |
|  |  |  |  | 885 |  |  |  |  | 890 |  |  |  |  | 895 |  |  |
| TAC | ATC | AAG | GAT | ATG | GCC | AAA | GAC | TCT | GAC | TAT | AAA | TTT | TCC | CTT | CAA | 2915 |
| Tyr | Ile | Lys | Asp | Met | Ala | Lys | Asp | Ser | Asp | Tyr | Lys | Phe | Ser | Leu | Gln |  |
|  |  |  | 900 |  |  |  |  | 905 |  |  |  |  | 910 |  |  |  |
| TTT | GAG | GAG | TTG | AAA | TTG | ATC | GGA | CTG | GAT | ATT | CCA | CAT | TTT | GCT | GCC | 2963 |
| Phe | Glu | Glu | Leu | Lys | Leu | Ile | Gly | Leu | Asp | Ile | Pro | His | Phe | Ala | Ala |  |
|  |  | 915 |  |  |  |  | 920 |  |  |  |  | 925 |  |  |  |  |
| GAT | CTT | CCA | CTG | AAC | CGA | TGT | AAA | AAC | CGT | TAC | ACA | AAC | ATC | TTG | CCA | 3011 |
| Asp | Leu | Pro | Leu | Asn | Arg | Cys | Lys | Asn | Arg | Tyr | Thr | Asn | Ile | Leu | Pro |  |
|  | 930 |  |  |  | 935 |  |  |  |  | 940 |  |  |  |  |  |  |
| TAT | GAC | TTT | AGC | CGA | GTG | AGA | TTA | CTC | TCC | ATG | AAT | GAA | GAG | GAA | GGT | 3059 |
| Tyr | Asp | Phe | Ser | Arg | Val | Arg | Leu | Leu | Ser | Met | Asn | Glu | Glu | Glu | Gly |  |
| 945 |  |  |  | 950 |  |  |  |  | 955 |  |  |  |  | 960 |  |  |
| GCG | GAC | TAT | ATT | AAT | GCC | AAC | TAT | ATT | CCT | GGG | TAC | AAC | TCA | CCC | CAG | 3107 |
| Ala | Asp | Tyr | Ile | Asn | Ala | Asn | Tyr | Ile | Pro | Gly | Tyr | Asn | Ser | Pro | Gln |  |
|  |  |  |  | 965 |  |  |  |  | 970 |  |  |  |  | 975 |  |  |
| GAG | TAC | ATT | GCC | ACC | CAG | GGG | CCG | CTG | CCT | GAA | ACC | AGA | AAT | GAC | TTC | 3155 |
| Glu | Tyr | Ile | Ala | Thr | Gln | Gly | Pro | Leu | Pro | Glu | Thr | Arg | Asn | Asp | Phe |  |
|  |  |  | 980 |  |  |  |  | 985 |  |  |  |  | 990 |  |  |  |
| TGG | AAG | ATG | GTC | CTA | CAA | CAG | AAG | TCG | CAG | ATG | ATT | GTC | ATG | CTC | ACT | 3203 |
| Trp | Lys | Met | Val | Leu | Gln | Gln | Lys | Ser | Gln | Met | Ile | Val | Met | Leu | Thr |  |
|  |  | 995 |  |  |  |  | 1000 |  |  |  |  | 1005 |  |  |  |  |
| CAA | TGC | AAT | GAG | AAA | AGG | AGG | GTG | AAA | TGC | GAC | CAT | TAT | TGG | CCA | TTC | 3251 |
| Gln | Cys | Asn | Glu | Lys | Arg | Arg | Val | Lys | Cys | Asp | His | Tyr | Trp | Pro | Phe |  |
|  | 1010 |  |  |  | 1015 |  |  |  |  | 1020 |  |  |  |  |  |  |
| ACG | GAA | GAA | CCC | ATC | GCC | TAC | GGG | GAC | ATC | ACC | GTG | GAG | ATG | ATC | TCG | 3299 |
| Thr | Glu | Glu | Pro | Ile | Ala | Tyr | Gly | Asp | Ile | Thr | Val | Glu | Met | Ile | Ser |  |
| 1025 |  |  |  | 1030 |  |  |  |  | 1035 |  |  |  |  | 1040 |  |  |
| GAG | GAA | GAA | CAG | GAT | GAC | TGG | GCC | CAT | AGA | CAC | TTC | CGG | ATC | AAC | TAC | 3347 |
| Glu | Glu | Glu | Gln | Asp | Asp | Trp | Ala | His | Arg | His | Phe | Arg | Ile | Asn | Tyr |  |
|  |  |  |  | 1045 |  |  |  |  | 1050 |  |  |  |  | 1055 |  |  |
| GCT | GAT | GAG | ATG | CAG | GAT | GTG | ATG | CAT | TTT | AAT | TAC | ACT | GCA | TGG | CCT | 3395 |
| Ala | Asp | Glu | Met | Gln | Asp | Val | Met | His | Phe | Asn | Tyr | Thr | Ala | Trp | Pro |  |
|  |  |  | 1060 |  |  |  |  | 1065 |  |  |  |  | 1070 |  |  |  |
| GAT | CAC | GGT | GTA | CCC | ACG | GCC | AAT | GCC | GCT | GAA | AGT | ATC | CTG | CAG | TTT | 3443 |
| Asp | His | Gly | Val | Pro | Thr | Ala | Asn | Ala | Ala | Glu | Ser | Ile | Leu | Gln | Phe |  |

```
          1075                    1080                    1085
GTA CAC ATG GTC CGA CAG CAA GCC ACC AAG AGC AAA GGC CCC ATG ATC          3491
Val His Met Val Arg Gln Gln Ala Thr Lys Ser Lys Gly Pro Met Ile
    1090                1095                1100

ATT CAC TGC AGC GCT GGA GTG GGG CGG ACA GGA ACC TTC ATT GCC CTG          3539
Ile His Cys Ser Ala Gly Val Gly Arg Thr Gly Thr Phe Ile Ala Leu
1105                1110                1115                1120

GAC AGG CTC CTG CAG CAC ATT CGG GAC CAT GAG TTT GTC GAC ATC TTA          3587
Asp Arg Leu Leu Gln His Ile Arg Asp His Glu Phe Val Asp Ile Leu
            1125                1130                1135

GGG CTG GTG TCG GAA ATG AGG TCA TAC AGG ATG TCT ATG GTA CAG ACA          3635
Gly Leu Val Ser Glu Met Arg Ser Tyr Arg Met Ser Met Val Gln Thr
        1140                1145                1150

GAG GAG CAG TAC ATT TTT ATC CAT CAG TGT GTG CAG CTG ATG TGG ATG          3683
Glu Glu Gln Tyr Ile Phe Ile His Gln Cys Val Gln Leu Met Trp Met
            1155                1160                1165

AAG AAG AAG CAG CAA TTC TGC ATC AGT GAC GTC ATA TAC GAA AAT GTT          3731
Lys Lys Lys Gln Gln Phe Cys Ile Ser Asp Val Ile Tyr Glu Asn Val
    1170                1175                1180

AGC AAG TCC TAGTTCAGGA TCCAGAGCAG AGAGGACGTG ATCTGCACCC                  3780
Ser Lys Ser
1185

ATCCTCCCTT GCTTCCAGAC ATTTTGGGGA GCCCTGCTAG TCATTTGCT  AACAGGAGCC        3840
CCTGCTTTGT AGTATGTGGC CAAGGAGATA ATTTTATCTC ATAGAAGCAC TGAGAAGACT        3900
TAGCCTTAAA GAGCCTACAG TGTCTTTTGG ACTCTTTCAC TTCTGGAAAT TTAATAATGG        3960
ACAAACCCAA CAGAACACCT GAAAGGTCAA GATGCACTCT GCAAAGGGCA GCGAGTATGG        4020
CACTTCTCAA GACTTTCAGG CCCTTTGCTA GTTGGGCTGA GTTTTTGTG  TTCATTTTTT        4080
TAAAGTGCAA TAATTTCTGT ATATGATTTT ATCAGACAGT TGAATTGTTT TCTGCCCACA        4140
CCATTGACCG ACCCCATAGC CCAGGAAGGA ACAGGCATGG TTAGCATTGA ATTATACCTC        4200
ATTGTTCAAA AAAAGCATGG TCACACATCA AGAAATAGCA ATTCTACTTC AAGTAAATGG        4260
ACCCAGCAAT GTCTGTACTG CAAACCTAAG CTACCAGATC AGAAGCGGGG AGGGTGGATG        4320
GGTAAGAGAG AGGGCTTCTA CCCACAGATC AACCACAAAT CTTTTCCTAT TCAAAATATG        4380
AAAAGCTGTA ATTTAACTTC AAAGTAGAAT AGAAAAATAT TTGTATTAAG TGGTCTAGTT        4440
CTTGATGGTT TTCTTCTTTA TTAACAGTTC GATGTTTTTT CCTTGGCCCC TTTGGAATAA        4500
TGTGACTGTC CAGGTTCTTT TTCAAGAAAC CAGATCTGGT TCAGAAGAGC GTCAAGTCTC        4560
ATTCTTCAAA CTCTGTTGCT GTTGAGCAA  TCTTGGTGCC TACACTTTGT ATTCCTTTCT        4620
CTGTCACTTG AACACCTGTG AAAGCTATTT CTTTGTGAAC TATAGGCTGT GAAAATGCAC        4680
TTTCTTTCCC CCCCCAAAGA GCTGGGAATT TATGAAATTA TGACAAAGCA TGCTAGGACA        4740
ATTCTTTGGC TACATTTCCT GTAATATTGT CAAGTATCTC TATGGATTAC CAAGGAGATT        4800
TCTTTTTTGT TATTTCTGTT TGACTGTCAG TTTCATTTTA AGCAATGTAA CTAGTAACAT        4860
TTCATTCTTT AGATTTTGTA TAATTACAGT ACATGATTGT GTATTGTGAC ATGAATGCTG        4920
TCAAAATGGA CATTGATGGC ATTGTGAAGC CTGTTCCTTT GTGTCACTTC CTGAGAAATA        4980
GGTGGTGGTA TAGATATACC AAGGAAAACA TTTGGAGTGG AAAGTAAACA CAAGCTGGCC        5040
GCTTCCCGGT GGCTGTCATA GGAAGCCTTG CTTCTCTGTG TCTGATCACT GCCCATTCCT        5100
TGGCTTCCTG CCATTCCCGA TCACCTTTAT GAAACCGGGT ATACAGGATA AGCTTAATGC        5160
GCTATCAGAG ACGTTAGTGA TGGTGAACGA TGCCAAGTGA ACAGCTCTGC ACCCCACTGT        5220
CTCTCGTCCC GAGAAACCCT GTCCACAACA GACCTTGACA ACATTCCTGG CAAGACGGTC        5280
```

-continued

```
AGTGAGTCCC AGTGTCACCT CGCAATGTGA TTGGCAGAGG ATGTGCACAC CTGCAGGTTA    5340
ACAGCTTGGG CTCCTCGGGG ATTGTCACTT CTCACTCACC CTTCCTCTAC TTCATGCTTC    5400
CCTGCTGCTG CTTCCTCCTC TTCTCACCCC ACTCCTTTAT TTCCCTTCTT GGACATTTTA    5460
ATCATCTATC ACACCATACT CAACAACAAA CATGATTACA GAAAGGCGGC AAATGTATGT    5520
GTGACATTCT TCTGTTATCA CACAAGGATA GCCCAAGAGT GGAGCCTGTG ACTTCGGAAG    5580
AGCTGGTGCT GTGTGTGGTG TGGGGTGGGG GTGGGAGAGC AGAAATGCAG TTCCAACACT    5640
GCCACACAGG AGCTTACAGA GGTTGTGTAA CCTGGAACC                           5679
```

( 2 ) INFORMATION FOR SEQ ID NO:2:

( i ) SEQUENCE CHARACTERISTICS:
      ( A ) LENGTH: 1187 amino acids
      ( B ) TYPE: amino acid
      ( D ) TOPOLOGY: linear ( i i ) MOLECULE TYPE: protein ( x i ) SEQUENCE DESCRIPTION: SEQ ID NO:2:

```
Met Gly His Leu Pro Thr Arg Ala Arg Gly Arg Arg Arg Leu Leu Pro
 1               5                  10                  15

Leu Leu Trp Leu Phe Val Leu Leu Lys Thr Ala Ala Ala Phe His Val
            20                  25                  30

Thr Val Arg Asp Asp Asn Ser Ile Val Val Ser Leu Glu Ala Ser Asp
        35                  40                  45

Val Ile Ser Pro Ala Ser Val Tyr Val Val Lys Ile Thr Gly Glu Ser
    50                  55                  60

Lys Asn Tyr Phe Phe Glu Phe Glu Glu Phe Asn Ser Thr Leu Pro Pro
65                  70                  75                  80

Pro Val Ile Phe Lys Ala Asn Tyr His Gly Leu Tyr Tyr Ile Ile Thr
                85                  90                  95

Leu Val Val Val Asn Gly Asn Val Val Thr Lys Pro Ser Arg Ser Ile
                100                 105                 110

Thr Val Leu Thr Lys Pro Leu Pro Val Thr Ser Val Ser Ile Tyr Asp
            115                 120                 125

Tyr Lys Pro Ser Pro Glu Thr Gly Val Leu Phe Glu Ile His Tyr Pro
    130                 135                 140

Glu Lys Tyr Asn Val Phe Thr Arg Val Asn Ile Ser Tyr Trp Glu Gly
145                 150                 155                 160

Lys Ala Phe Arg Thr Met Leu Tyr Lys Asp Phe Phe Lys Gly Lys Thr
                165                 170                 175

Val Phe Asn His Trp Leu Pro Gly Ile Cys Tyr Ser Asn Ile Thr Phe
            180                 185                 190

Gln Leu Val Ser Glu Ala Thr Phe Asn Lys Ser Thr Leu Val Glu Tyr
        195                 200                 205

Ser Gly Val Ser His Glu Pro Lys Gln His Arg Thr Ala Pro Tyr Pro
    210                 215                 220

Pro Arg Asn Ile Ser Val Arg Ile Val Asn Leu Asn Lys Asn Asn Trp
225                 230                 235                 240

Glu Glu Gln Ser Gly Ser Phe Pro Glu Glu Ser Phe Met Arg Ser Pro
                245                 250                 255

Glu Thr Ile Glu Lys Asp Arg Ile Phe His Phe Thr Glu Glu Thr Pro
            260                 265                 270

Glu Pro Ser Gly Asn Ile Ser Ser Gly Trp Pro Asp Phe Asn Ser Ser
    275                 280                 285
```

| | | | | | | | | | | | | | | |
|---|---|---|---|---|---|---|---|---|---|---|---|---|---|---|
| Asp | Tyr 290 | Glu | Thr | Thr | Ser | Gln 295 | Pro | Tyr | Trp | Trp 300 | Asp | Ser | Ala | Ser | Ala |
| Thr 305 | Pro | Glu | Ser | Glu 310 | Asp | Glu | Phe | Val | Ser 315 | Val | Leu | Pro | Met | Glu | Tyr 320 |
| Glu | Asn | Asn | Asn | Thr 325 | Leu | Ser | Glu | Ala | Glu 330 | Lys | Pro | Thr | Pro 335 | Ala | Pro |
| Phe | Ser | Phe | Phe 340 | Pro | Val | Gln | Met | Ile 345 | Leu | Ser | Trp | Leu 350 | Pro | Pro | Lys |
| Pro | Pro | Thr 355 | Ala | Phe | Asp | Gly | Phe 360 | His | Ile | His | Ile 365 | Glu | Arg | Glu | Glu |
| Asn | Phe 370 | Thr | Glu | Tyr | Ser | Thr 375 | Val | Asp | Glu | Glu | Ala 380 | His | Glu | Phe | Val |
| Ala 385 | Glu | Leu | Lys | Glu | Pro 390 | Gly | Lys | Tyr | Lys | Leu 395 | Ser | Val | Thr | Thr | Phe 400 |
| Ser | Ala | Ser | Gly | Ser 405 | Cys | Glu | Thr | Arg | Glu 410 | Ser | Gln | Ser | Ala | Lys 415 | Ser |
| Leu | Ser | Phe | Tyr 420 | Ile | Ser | Pro | Thr | Gly 425 | Glu | Trp | Ile | Glu | Glu 430 | Leu | Thr |
| Glu | Lys | Pro 435 | Gln | His | Val | Ser | Val 440 | His | Val | Leu | Ser | Ser 445 | Thr | Thr | Ala |
| Leu | Met 450 | Ser | Trp | Thr | Ser | Ser 455 | Gln | Glu | Asn | Tyr | Asn 460 | Ser | Thr | Ile | Val |
| Ser 465 | Val | Val | Ser | Leu | Thr 470 | Cys | Gln | Lys | Gln | Lys 475 | Glu | Ser | Gln | Arg | Leu 480 |
| Glu | Lys | Gln | Tyr | Cys 485 | Thr | Gln | Val | Asn | Ser 490 | Ser | Lys | Arg | Ile | Ile 495 | Glu |
| Asn | Leu | Val | Pro 500 | Gly | Ala | Gln | Tyr | Gln 505 | Val | Val | Met | Tyr 510 | Leu | Arg | Lys |
| Gly | Pro | Leu 515 | Ile | Gly | Pro | Pro | Ser 520 | Asp | Pro | Val | Thr | Phe 525 | Ala | Ile | Val |
| Pro | Thr 530 | Gly | Ile | Lys | Asp | Leu 535 | Met | Leu | Tyr | Pro | Leu 540 | Gly | Pro | Thr | Ala |
| Val 545 | Val | Leu | Ser | Trp | Thr 550 | Arg | Pro | Tyr | Leu | Gly 555 | Val | Phe | Arg | Lys | Tyr 560 |
| Val | Val | Glu | Met | Phe 565 | Tyr | Phe | Asn | Pro | Ala 570 | Thr | Met | Thr | Ser | Glu 575 | Trp |
| Thr | Thr | Tyr | Tyr 580 | Glu | Ile | Ala | Ala | Thr 585 | Val | Ser | Leu | Thr | Ala 590 | Ser | Val |
| Arg | Ile | Ala 595 | Asn | Leu | Leu | Pro | Ala 600 | Trp | Tyr | Tyr | Asn | Phe 605 | Arg | Val | Thr |
| Met | Val 610 | Thr | Trp | Gly | Asp | Pro 615 | Glu | Leu | Ser | Cys | Cys 620 | Asp | Ser | Ser | Thr |
| Ile 625 | Ser | Phe | Ile | Thr | Ala 630 | Pro | Val | Ala | Pro | Glu 635 | Ile | Thr | Ser | Val | Glu 640 |
| Tyr | Phe | Asn | Ser | Leu 645 | Leu | Tyr | Ile | Ser | Trp 650 | Thr | Tyr | Gly | Asp | Thr 655 | |
| Thr | Asp | Leu | Ser | His 660 | Ser | Arg | Met | Leu 665 | His | Trp | Met | Val 670 | Ala | Glu | |
| Gly | Lys | Lys 675 | Lys | Ile | Lys | Lys | Ser 680 | Val | Thr | Arg | Asn | Val 685 | Met | Thr | Ala |
| Ile | Leu | Ser 690 | Leu | Pro | Pro | Gly | Asp 695 | Ile | Tyr | Asn | Leu | Ser 700 | Val | Thr | Ala |
| Cys 705 | Thr | Glu | Arg | Gly | Ser 710 | Asn | Thr | Ser | Met | Leu 715 | Arg | Leu | Val | Lys | Leu 720 |

```
Glu Pro Ala Pro Pro Lys Ser Leu Phe Ala Val Asn Lys Thr Gln Thr
                725                 730                 735

Ser Val Thr Leu Leu Trp Val Glu Gly Val Ala Asp Phe Phe Glu
            740                 745                 750

Val Phe Cys Gln Gln Val Gly Ser Gly Leu Glu Thr Lys Leu Gln Glu
        755                 760                 765

Pro Val Ala Val Ser Ser His Val Val Thr Ile Ser Ser Leu Leu Pro
        770                 775                 780

Ala Thr Ala Tyr Asn Cys Ser Val Thr Ser Phe Ser His Asp Ser Pro
785                 790                 795                 800

Ser Val Pro Thr Phe Ile Ala Val Ser Thr Met Val Thr Glu Met Asn
                805                 810                 815

Pro Asn Val Val Val Ile Ser Val Leu Ala Ile Leu Ser Thr Leu Leu
            820                 825                 830

Ile Gly Leu Leu Leu Val Thr Leu Ile Ile Leu Arg Lys Lys His Leu
        835                 840                 845

Gln Met Ala Arg Glu Cys Gly Ala Gly Thr Phe Val Asn Phe Ala Ser
    850                 855                 860

Leu Glu Arg Asp Gly Lys Leu Pro Tyr Asn Trp Ser Lys Asn Gly Leu
865                 870                 875                 880

Lys Lys Arg Lys Leu Thr Asn Pro Val Gln Leu Asp Asp Phe Asp Ala
                885                 890                 895

Tyr Ile Lys Asp Met Ala Lys Asp Ser Asp Tyr Lys Phe Ser Leu Gln
            900                 905                 910

Phe Glu Glu Leu Lys Leu Ile Gly Leu Asp Ile Pro His Phe Ala Ala
        915                 920                 925

Asp Leu Pro Leu Asn Arg Cys Lys Asn Arg Tyr Thr Asn Ile Leu Pro
    930                 935                 940

Tyr Asp Phe Ser Arg Val Arg Leu Leu Ser Met Asn Glu Glu Glu Gly
945                 950                 955                 960

Ala Asp Tyr Ile Asn Ala Asn Tyr Ile Pro Gly Tyr Asn Ser Pro Gln
                965                 970                 975

Glu Tyr Ile Ala Thr Gln Gly Pro Leu Pro Glu Thr Arg Asn Asp Phe
            980                 985                 990

Trp Lys Met Val Leu Gln Gln Lys Ser Gln Met Ile Val Met Leu Thr
        995                 1000                1005

Gln Cys Asn Glu Lys Arg Arg Val Lys Cys Asp His Tyr Trp Pro Phe
    1010                1015                1020

Thr Glu Glu Pro Ile Ala Tyr Gly Asp Ile Thr Val Glu Met Ile Ser
1025                1030                1035                1040

Glu Glu Glu Gln Asp Asp Trp Ala His Arg His Phe Arg Ile Asn Tyr
                1045                1050                1055

Ala Asp Glu Met Gln Asp Val Met His Phe Asn Tyr Thr Ala Trp Pro
            1060                1065                1070

Asp His Gly Val Pro Thr Ala Asn Ala Ala Glu Ser Ile Leu Gln Phe
        1075                1080                1085

Val His Met Val Arg Gln Gln Ala Thr Lys Ser Lys Gly Pro Met Ile
    1090                1095                1100

Ile His Cys Ser Ala Gly Val Gly Arg Thr Gly Thr Phe Ile Ala Leu
1105                1110                1115                1120

Asp Arg Leu Leu Gln His Ile Arg Asp His Glu Phe Val Asp Ile Leu
                1125                1130                1135

Gly Leu Val Ser Glu Met Arg Ser Tyr Arg Met Ser Met Val Gln Thr
```

|       |       |       |       |       |       |       |       |       |       |       |       |       |       |       |      |
|-------|-------|-------|-------|-------|-------|-------|-------|-------|-------|-------|-------|-------|-------|-------|------|
|       |       |       | 1140  |       |       |       |       | 1145  |       |       |       |       | 1150  |       |      |
| Glu   | Glu   | Gln   | Tyr   | Ile   | Phe   | Ile   | His   | Gln   | Cys   | Val   | Gln   | Leu   | Met   | Trp   | Met  |
|       |       |       |       | 1155  |       |       |       |       | 1160  |       |       |       |       | 1165  |      |
| Lys   | Lys   | Lys   | Gln   | Gln   | Phe   | Cys   | Ile   | Ser   | Asp   | Val   | Ile   | Tyr   | Glu   | Asn   | Val  |
|       |       |       | 1170  |       |       |       |       | 1175  |       |       |       | 1180  |       |       |      |
| Ser   | Lys   | Ser   |       |       |       |       |       |       |       |       |       |       |       |       |      |
| 1185  |       |       |       |       |       |       |       |       |       |       |       |       |       |       |      |

( 2 ) INFORMATION FOR SEQ ID NO:3:

( i ) SEQUENCE CHARACTERISTICS:
        ( A ) LENGTH: 4752 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 808..4372

( x i ) SEQUENCE DESCRIPTION: SEQ ID NO:3:

```
TTCCGGAGTT  TGCGCTTCTA  TTGATCCAAT  CCCATTGCCC  AGATATTGAA  CACAGTACCC       60

AACAGGAAGT  TTTTCAGCAC  TTGCCCCACT  CCCTCATTTT  GGAGTCCCA   GTGTCTTTTG      120

TTCCAGCTT   CATATCTGTG  TGTACCCAAG  ATTAGCTCT   CACTTATAAG  TGAGAACATG      180

TGGCATTTGT  TTTTTGTTT   CTGCGTTAAT  TTGCTAAAGA  TAATGGCCTC  CAGCTCCATC      240

TGTGTTCCTG  CAAAGAACAT  GATCTCATTC  TTCTTATGGA  TGCATAGTAT  TCCATGATGT      300

ATATGTACCA  CATTGTATTA  GTCTGTTTCC  ATGCTGCTGA  TAAAGACTTA  CCCGAGACTG      360

GGCAATTTAC  AAAAGAAAGA  GGTTTAATTG  GACTCACAGT  TCCATGTGGC  TGGGGAGACC      420

TCATAATCAT  GGCAGAAGGC  AAGGCCAGGG  ATGCTGCTAG  GCATCCTAAA  ATGCAGAGGC      480

CACGGTCCAC  AATAGAGCTT  CAACAGCTCC  AAGGCCGGAA  TTCCGGGCAG  CCGCGGTGGT      540

GGCGGCGGCA  GAGCCTCGCC  CACTCCAATC  CCACCCTCT   CCATCCTTAG  TCATTAAAGA      600

ACAGCAGCGC  CTGGCACGTT  CTTGGAGGAC  CCCGGGCGCA  GAGGAGGAAA  GGGAGCAGGC      660

GCAGGGGGAC  TGGAAAGGCA  GCATGCGCTC  GCCAGGAGCA  ACCTCGGCGC  CAGGGTCTG      720

AGGCTGCAGC  CCCAGTTCGC  CATTGTGAGC  CGCCGCCGGG  GGAGTCCGCT  AGCGCAGCCG      780

TGCCCCCGAG  TCCCCGTCCG  CGCAGCG ATG GGG CAC CTG CCC ACG GGG ATA            831
                                Met Gly His Leu Pro Thr Gly Ile
                                  1               5
```

|       |       |       |       |       |       |       |       |       |       |       |       |       |       |       |        |
|-------|-------|-------|-------|-------|-------|-------|-------|-------|-------|-------|-------|-------|-------|-------|--------|
| CAC   | GGC   | GCC   | CGC   | CGC   | CTC   | CTG   | CCT   | CTG   | CTC   | TGG   | CTC   | TTT   | GTG   | CTG   | TTC    |
| His   | Gly   | Ala   | Arg   | Arg   | Leu   | Leu   | Pro   | Leu   | Leu   | Trp   | Leu   | Phe   | Val   | Leu   | Phe    |
|       | 10    |       |       |       | 15    |       |       |       |       | 20    |       |       |       |       |        |
| AAG   | AAT   | GCT   | ACA   | GCT   | TTC   | CAT   | GTA   | ACT   | GTC   | CAA   | GAT   | GAT   | AAT   | AAC   | ATC    |
| Lys   | Asn   | Ala   | Thr   | Ala   | Phe   | His   | Val   | Thr   | Val   | Gln   | Asp   | Asp   | Asn   | Asn   | Ile    |
| 25    |       |       |       |       | 30    |       |       |       |       | 35    |       |       |       |       | 40     |
| GTT   | GTC   | TCA   | TTA   | GAA   | GCT   | TCA   | GAC   | GTC   | ATC   | AGT   | CCA   | GCA   | TCT   | GTG   | TAT    |
| Val   | Val   | Ser   | Leu   | Glu   | Ala   | Ser   | Asp   | Val   | Ile   | Ser   | Pro   | Ala   | Ser   | Val   | Tyr    |
|       |       |       |       | 45    |       |       |       |       | 50    |       |       |       |       | 55    |        |
| GTT   | GTG   | AAG   | ATA   | ACT   | GGT   | GAA   | TCC   | AAA   | AAT   | TAT   | TTC   | TTC   | GAA   | TTT   | GAG    |
| Val   | Val   | Lys   | Ile   | Thr   | Gly   | Glu   | Ser   | Lys   | Asn   | Tyr   | Phe   | Phe   | Glu   | Phe   | Glu    |
|       |       |       | 60    |       |       |       |       | 65    |       |       |       |       | 70    |       |        |
| GAA   | TTC   | AAC   | AGC   | ACT   | TTG   | CCT   | CCT   | CCT   | GTT   | ATT   | TTC   | AAG   | GCC   | AGT   | TAT    |
| Glu   | Phe   | Asn   | Ser   | Thr   | Leu   | Pro   | Pro   | Pro   | Val   | Ile   | Phe   | Lys   | Ala   | Ser   | Tyr    |
|       |       | 75    |       |       |       |       | 80    |       |       |       |       | 85    |       |       |        |
| CAT   | GGC   | CTT   | TAT   | TAT   | ATA   | ATC   | ACT   | CTG   | GTA   | GTG   | GTA   | AAT   | GGA   | AAT   | GTG    |
| His   | Gly   | Leu   | Tyr   | Tyr   | Ile   | Ile   | Thr   | Leu   | Val   | Val   | Val   | Asn   | Gly   | Asn   | Val    |
|       | 90    |       |       |       | 95    |       |       |       |       | 100   |       |       |       |       |        |

Offsets: 879, 927, 975, 1023, 1071, 1119

| | | | | | | | | | | | | | | | | |
|---|---|---|---|---|---|---|---|---|---|---|---|---|---|---|---|---|
| GTG | ACC | AAG | CCA | TCC | AGA | TCA | ATC | ACT | GTG | TTA | ACA | AAA | CCT | CTA | CCT | 1167 |
| Val | Thr | Lys | Pro | Ser | Arg | Ser | Ile | Thr | Val | Leu | Thr | Lys | Pro | Leu | Pro | |
| 105 | | | | 110 | | | | | 115 | | | | | | 120 | |
| GTA | ACC | AGT | GTT | TCC | ATA | TAT | GAC | TAT | AAA | CCT | TCT | CCT | GAA | ACA | GGA | 1215 |
| Val | Thr | Ser | Val | Ser | Ile | Tyr | Asp | Tyr | Lys | Pro | Ser | Pro | Glu | Thr | Gly | |
| | | | | 125 | | | | | 130 | | | | | | 135 | |
| GTC | CTG | TTT | GAA | ATA | CAT | TAT | CCA | GAA | AAA | TAT | AAC | GTT | TTC | ACA | AGA | 1263 |
| Val | Leu | Phe | Glu | Ile | His | Tyr | Pro | Glu | Lys | Tyr | Asn | Val | Phe | Thr | Arg | |
| | | | | 140 | | | | | 145 | | | | | 150 | | |
| GTG | AAC | ATT | AGC | TAC | TGG | GAA | GGT | AAA | GAC | TTC | CGG | ACA | ATG | CTA | TAT | 1311 |
| Val | Asn | Ile | Ser | Tyr | Trp | Glu | Gly | Lys | Asp | Phe | Arg | Thr | Met | Leu | Tyr | |
| | | | | 155 | | | | | 160 | | | | | 165 | | |
| AAA | GAT | TTC | TTT | AAG | GGA | AAA | ACA | GTA | TTT | AAT | CAC | TGG | CTG | CCA | GGA | 1359 |
| Lys | Asp | Phe | Phe | Lys | Gly | Lys | Thr | Val | Phe | Asn | His | Trp | Leu | Pro | Gly | |
| | 170 | | | | | 175 | | | | | 180 | | | | | |
| ATG | TGT | TAT | AGT | AAT | ATC | ACC | TTT | CAG | CTG | GTA | TCT | GAG | GCA | ACT | TTT | 1407 |
| Met | Cys | Tyr | Ser | Asn | Ile | Thr | Phe | Gln | Leu | Val | Ser | Glu | Ala | Thr | Phe | |
| 185 | | | | | 190 | | | | | 195 | | | | | 200 | |
| AAT | AAA | AGT | ACC | CTT | GTT | GAG | TAC | AGT | GGT | GTC | AGT | CAC | GAA | CCC | AAA | 1455 |
| Asn | Lys | Ser | Thr | Leu | Val | Glu | Tyr | Ser | Gly | Val | Ser | His | Glu | Pro | Lys | |
| | | | | 205 | | | | | 210 | | | | | 215 | | |
| CAG | CAC | AGA | ACT | GCC | CCT | TAT | CCA | CCT | CAA | AAT | ATT | TCC | GTT | CGT | ATC | 1503 |
| Gln | His | Arg | Thr | Ala | Pro | Tyr | Pro | Pro | Gln | Asn | Ile | Ser | Val | Arg | Ile | |
| | | | 220 | | | | | 225 | | | | | 230 | | | |
| GTA | AAC | TTG | AAC | AAA | AAC | AAC | TGG | GAA | GAA | CAG | AGT | GGC | AAT | TTC | CCA | 1551 |
| Val | Asn | Leu | Asn | Lys | Asn | Asn | Trp | Glu | Glu | Gln | Ser | Gly | Asn | Phe | Pro | |
| | | | 235 | | | | | 240 | | | | | 245 | | | |
| GAA | GAA | TCC | TTC | ATG | AGA | TCA | CAA | GAT | ACA | ATA | GGA | AAA | GAA | AAA | CTC | 1599 |
| Glu | Glu | Ser | Phe | Met | Arg | Ser | Gln | Asp | Thr | Ile | Gly | Lys | Glu | Lys | Leu | |
| | 250 | | | | | 255 | | | | | 260 | | | | | |
| TTC | CAT | TTT | ACA | GAA | GAA | ACC | CCT | GAA | ATT | CCC | TCG | GGC | AAC | ATT | TCT | 1647 |
| Phe | His | Phe | Thr | Glu | Glu | Thr | Pro | Glu | Ile | Pro | Ser | Gly | Asn | Ile | Ser | |
| 265 | | | | | 270 | | | | | 275 | | | | | 280 | |
| TCC | GGT | TGG | CCT | GAT | TTT | AAT | AGC | AGT | GAC | TAT | GAA | ACT | ACG | TCT | CAG | 1695 |
| Ser | Gly | Trp | Pro | Asp | Phe | Asn | Ser | Ser | Asp | Tyr | Glu | Thr | Thr | Ser | Gln | |
| | | | | 285 | | | | | 290 | | | | | 295 | | |
| CCA | TAT | TGG | TGG | GAC | AGT | GCA | TCT | GCA | GCT | CCT | GAA | AGT | GAA | GAT | GAA | 1743 |
| Pro | Tyr | Trp | Trp | Asp | Ser | Ala | Ser | Ala | Ala | Pro | Glu | Ser | Glu | Asp | Glu | |
| | | | 300 | | | | | 305 | | | | | 310 | | | |
| TTT | GTC | AGC | GTA | CTT | CCC | ATG | GAA | TAC | GAA | AAT | AAC | AGT | ACA | CTC | AGT | 1791 |
| Phe | Val | Ser | Val | Leu | Pro | Met | Glu | Tyr | Glu | Asn | Asn | Ser | Thr | Leu | Ser | |
| | | 315 | | | | | 320 | | | | | 325 | | | | |
| GAG | ACA | GAG | AAG | TCA | ACA | TCA | GGC | TCT | TTC | TCC | TTT | TTC | CCT | GTG | CAA | 1839 |
| Glu | Thr | Glu | Lys | Ser | Thr | Ser | Gly | Ser | Phe | Ser | Phe | Phe | Pro | Val | Gln | |
| | 330 | | | | | 335 | | | | | 340 | | | | | |
| ATG | ATA | TTG | ACC | TGG | TTA | CCA | CCC | AAA | CCA | CCC | ACT | GCT | TTT | GAT | GGG | 1887 |
| Met | Ile | Leu | Thr | Trp | Leu | Pro | Pro | Lys | Pro | Pro | Thr | Ala | Phe | Asp | Gly | |
| 345 | | | | | 350 | | | | | 355 | | | | | 360 | |
| TTC | CAT | ATC | CAT | ATT | GAA | CGA | GAA | GAG | AAG | TTT | ACT | GAA | TAT | TTG | ATG | 1935 |
| Phe | His | Ile | His | Ile | Glu | Arg | Glu | Glu | Lys | Phe | Thr | Glu | Tyr | Leu | Met | |
| | | | | 365 | | | | | 370 | | | | | 375 | | |
| GTG | GAT | GAA | GAA | GCA | CAT | GAA | TTT | GTT | GCA | GAA | CTG | AAG | GAA | CCT | GGG | 1983 |
| Val | Asp | Glu | Glu | Ala | His | Glu | Phe | Val | Ala | Glu | Leu | Lys | Glu | Pro | Gly | |
| | | | 380 | | | | | 385 | | | | | 390 | | | |
| AAA | TAT | AAG | TTA | TCT | GTG | ACA | ACC | TTT | AGT | TCC | TCA | GGA | TCT | TGT | GAA | 2031 |
| Lys | Tyr | Lys | Leu | Ser | Val | Thr | Thr | Phe | Ser | Ser | Ser | Gly | Ser | Cys | Glu | |
| | | 395 | | | | | 400 | | | | | 405 | | | | |
| ACT | CGA | AAA | AGT | CAG | TCA | GCA | AAA | TCA | CTC | AGC | TTT | TAT | ATC | AGT | CCT | 2079 |
| Thr | Arg | Lys | Ser | Gln | Ser | Ala | Lys | Ser | Leu | Ser | Phe | Tyr | Ile | Ser | Pro | |
| | 410 | | | | | 415 | | | | | 420 | | | | | |

| | | | | | | | | | | | | | | | | |
|---|---|---|---|---|---|---|---|---|---|---|---|---|---|---|---|---|
| TCA | GGA | GAG | TGG | ATT | GAA | GAA | CTG | ACC | GAG | AAG | CCG | CAG | CAC | GTG | AGT | 2127 |
| Ser | Gly | Glu | Trp | Ile | Glu | Glu | Leu | Thr | Glu | Lys | Pro | Gln | His | Val | Ser | |
| 425 | | | | 430 | | | | | 435 | | | | | | 440 | |
| GTC | CAC | GTT | TTA | AGC | TCA | ACC | ACT | GCC | TTG | ATG | TCC | TGG | ACA | TCT | TCC | 2175 |
| Val | His | Val | Leu | Ser | Ser | Thr | Thr | Ala | Leu | Met | Ser | Trp | Thr | Ser | Ser | |
| | | | | 445 | | | | | 450 | | | | | 455 | | |
| CAA | GAG | AAC | TAC | AAC | AGC | ACC | ATT | GTG | TCT | GTG | GTG | TCG | CTG | ACC | TGC | 2223 |
| Gln | Glu | Asn | Tyr | Asn | Ser | Thr | Ile | Val | Ser | Val | Val | Ser | Leu | Thr | Cys | |
| | | | | 460 | | | | | 465 | | | | | 470 | | |
| CAG | AAA | CAA | AAG | GAG | AGC | CAG | AGG | CTT | GAA | AAG | CAG | TAC | TGC | ACT | CAG | 2271 |
| Gln | Lys | Gln | Lys | Glu | Ser | Gln | Arg | Leu | Glu | Lys | Gln | Tyr | Cys | Thr | Gln | |
| | | | 475 | | | | | 480 | | | | | 485 | | | |
| GTG | AAC | TCA | AGC | AAA | CCT | ATT | ATT | GAA | AAT | CTG | GTT | CCT | GGT | GCC | CAG | 2319 |
| Val | Asn | Ser | Ser | Lys | Pro | Ile | Ile | Glu | Asn | Leu | Val | Pro | Gly | Ala | Gln | |
| | | 490 | | | | | 495 | | | | | 500 | | | | |
| TAC | CAG | GTT | GTA | ATA | TAC | CTA | AGG | AAA | GGC | CCT | TTG | ATT | GGA | CCA | CCT | 2367 |
| Tyr | Gln | Val | Val | Ile | Tyr | Leu | Arg | Lys | Gly | Pro | Leu | Ile | Gly | Pro | Pro | |
| 505 | | | | | 510 | | | | | 515 | | | | | 520 | |
| TCA | GAT | CCT | GTG | ACA | TTT | GCT | ATT | GTT | CCC | ACA | GGA | ATA | AAG | GAT | TTA | 2415 |
| Ser | Asp | Pro | Val | Thr | Phe | Ala | Ile | Val | Pro | Thr | Gly | Ile | Lys | Asp | Leu | |
| | | | | 525 | | | | | 530 | | | | | 535 | | |
| ATG | CTC | TAT | CCT | TTG | GGT | CCT | ACG | GCC | GTG | GTT | CTG | AGC | TGG | ACC | AGA | 2463 |
| Met | Leu | Tyr | Pro | Leu | Gly | Pro | Thr | Ala | Val | Val | Leu | Ser | Trp | Thr | Arg | |
| | | | | 540 | | | | | 545 | | | | | 550 | | |
| CCT | TAT | TTA | GGC | GTG | TTC | AGA | AAA | TAC | GTG | GTT | GAA | ATG | TTT | TAT | TTC | 2511 |
| Pro | Tyr | Leu | Gly | Val | Phe | Arg | Lys | Tyr | Val | Val | Glu | Met | Phe | Tyr | Phe | |
| | | 555 | | | | | 560 | | | | | 565 | | | | |
| AAC | CCT | GCT | ACA | ATG | ACA | TCA | GAG | TGG | ACC | ACC | TAC | TAT | GAA | ATA | GCA | 2559 |
| Asn | Pro | Ala | Thr | Met | Thr | Ser | Glu | Trp | Thr | Thr | Tyr | Tyr | Glu | Ile | Ala | |
| | 570 | | | | | 575 | | | | | 580 | | | | | |
| GCA | ACT | GTT | TCC | TTA | ACT | GCA | TCC | GTG | AGA | ATA | GCT | AAT | CTG | CTG | CCA | 2607 |
| Ala | Thr | Val | Ser | Leu | Thr | Ala | Ser | Val | Arg | Ile | Ala | Asn | Leu | Leu | Pro | |
| 585 | | | | | 590 | | | | | 595 | | | | | 600 | |
| GCA | TGG | TAC | TAC | AAC | TTC | CGG | GTT | ACC | ATG | GTG | ACG | TGG | GGA | GAT | CCA | 2655 |
| Ala | Trp | Tyr | Tyr | Asn | Phe | Arg | Val | Thr | Met | Val | Thr | Trp | Gly | Asp | Pro | |
| | | | | 605 | | | | | 610 | | | | | 615 | | |
| GAA | TTG | AGC | TGC | TGT | GAC | AGC | TCT | ACC | ATC | AGC | TTC | ATA | ACA | GCC | CCA | 2703 |
| Glu | Leu | Ser | Cys | Cys | Asp | Ser | Ser | Thr | Ile | Ser | Phe | Ile | Thr | Ala | Pro | |
| | | | 620 | | | | | 625 | | | | | 630 | | | |
| GTG | GCT | CCG | GAA | ATC | ACT | TCT | GTG | GAA | TAT | TTC | AAC | AGT | CTG | TTA | TAT | 2751 |
| Val | Ala | Pro | Glu | Ile | Thr | Ser | Val | Glu | Tyr | Phe | Asn | Ser | Leu | Leu | Tyr | |
| | | | 635 | | | | | 640 | | | | | 645 | | | |
| ATC | AGT | TGG | ACA | TAT | GGG | GAT | GAT | ACA | ACG | GAC | TTG | TCC | CAT | TCT | AGA | 2799 |
| Ile | Ser | Trp | Thr | Tyr | Gly | Asp | Asp | Thr | Thr | Asp | Leu | Ser | His | Ser | Arg | |
| | | 650 | | | | | 655 | | | | | 660 | | | | |
| ATG | CTT | CAC | TGG | ATG | GTG | GTT | GCA | GAA | GGA | AAA | AAG | AAA | ATT | AAA | AAG | 2847 |
| Met | Leu | His | Trp | Met | Val | Val | Ala | Glu | Gly | Lys | Lys | Lys | Ile | Lys | Lys | |
| 665 | | | | | 670 | | | | | 675 | | | | | 680 | |
| AGT | GTA | ACA | CGC | AAT | GTC | ATG | ACT | GCA | ATT | CTC | AGC | TTG | CCT | CCA | GGA | 2895 |
| Ser | Val | Thr | Arg | Asn | Val | Met | Thr | Ala | Ile | Leu | Ser | Leu | Pro | Pro | Gly | |
| | | | | 685 | | | | | 690 | | | | | 695 | | |
| GAC | ATC | TAT | AAC | CTC | TCA | GTA | ACT | GCT | TGT | ACT | GAA | AGA | GGA | AGT | AAT | 2943 |
| Asp | Ile | Tyr | Asn | Leu | Ser | Val | Thr | Ala | Cys | Thr | Glu | Arg | Gly | Ser | Asn | |
| | | | | 700 | | | | | 705 | | | | | 710 | | |
| ACC | TCC | ATG | CTC | CGC | CTT | GTC | AAG | CTA | GAA | CCA | GCT | CCA | CCC | AAA | TCA | 2991 |
| Thr | Ser | Met | Leu | Arg | Leu | Val | Lys | Leu | Glu | Pro | Ala | Pro | Pro | Lys | Ser | |
| | | | 715 | | | | | 720 | | | | | 725 | | | |
| CTC | TTC | GCA | GTG | AAC | AAA | ACC | CAG | ACT | TCA | GTG | ACT | TTG | CTG | TGG | GTG | 3039 |
| Leu | Phe | Ala | Val | Asn | Lys | Thr | Gln | Thr | Ser | Val | Thr | Leu | Leu | Trp | Val | |
| | | | 730 | | | | | 735 | | | | | 740 | | | |

| | | | | | | | | | | | | | | | | |
|---|---|---|---|---|---|---|---|---|---|---|---|---|---|---|---|---|
| GAA | GAG | GGA | GTA | GCT | GAT | TTC | TTT | GAA | GTT | TTC | TGT | CAA | CAA | GTT | GGC | 3087 |
| Glu | Glu | Gly | Val | Ala | Asp | Phe | Phe | Glu | Val | Phe | Cys | Gln | Gln | Val | Gly | |
| 745 | | | | 750 | | | | | 755 | | | | | | 760 | |
| TCC | AGT | CAG | AAA | ACC | AAA | CTT | CAG | GAA | CCA | GTT | GCT | GTT | TCT | TCC | CAT | 3135 |
| Ser | Ser | Gln | Lys | Thr | Lys | Leu | Gln | Glu | Pro | Val | Ala | Val | Ser | Ser | His | |
| | | | | 765 | | | | | 770 | | | | | 775 | | |
| GTC | GTG | ACC | ATC | TCC | AGC | CTT | CTT | CCT | GCC | ACT | GCC | TAC | AAT | TGT | AGT | 3183 |
| Val | Val | Thr | Ile | Ser | Ser | Leu | Leu | Pro | Ala | Thr | Ala | Tyr | Asn | Cys | Ser | |
| | | | 780 | | | | | 785 | | | | | 790 | | | |
| GTC | ACC | AGC | TTT | AGC | CAT | GAC | AGC | CCC | AGT | GTC | CCT | ACG | TTC | ATA | GCC | 3231 |
| Val | Thr | Ser | Phe | Ser | His | Asp | Ser | Pro | Ser | Val | Pro | Thr | Phe | Ile | Ala | |
| | | 795 | | | | | 800 | | | | | 805 | | | | |
| GTC | TCA | ACA | ATG | GTT | ACA | GAG | ATG | AAT | CCC | AAT | GTG | GTA | GTG | ATC | TCC | 3279 |
| Val | Ser | Thr | Met | Val | Thr | Glu | Met | Asn | Pro | Asn | Val | Val | Val | Ile | Ser | |
| | 810 | | | | | 815 | | | | | 820 | | | | | |
| GTG | CTG | GCC | ATC | CTT | AGC | ACA | CTT | TTA | ATT | GGA | CTG | TTG | CTT | GTT | ACC | 3327 |
| Val | Leu | Ala | Ile | Leu | Ser | Thr | Leu | Leu | Ile | Gly | Leu | Leu | Leu | Val | Thr | |
| 825 | | | | | 830 | | | | | 835 | | | | | 840 | |
| CTC | ATT | ATT | CTT | AGG | AAA | AAG | CAT | CTG | CAG | ATG | GCT | AGG | GAG | TGT | GGA | 3375 |
| Leu | Ile | Ile | Leu | Arg | Lys | Lys | His | Leu | Gln | Met | Ala | Arg | Glu | Cys | Gly | |
| | | | | 845 | | | | | 850 | | | | | 855 | | |
| GCT | GGT | ACA | TTT | GTC | AAT | TTT | GCA | TCC | TTA | GAG | AGG | GAT | GGA | AAG | CTT | 3423 |
| Ala | Gly | Thr | Phe | Val | Asn | Phe | Ala | Ser | Leu | Glu | Arg | Asp | Gly | Lys | Leu | |
| | | | 860 | | | | | 865 | | | | | 870 | | | |
| CCA | TAC | AAC | TGG | AGT | AAA | AAT | GGT | TTA | AAG | AAG | AGG | AAA | CTG | ACA | AAC | 3471 |
| Pro | Tyr | Asn | Trp | Ser | Lys | Asn | Gly | Leu | Lys | Lys | Arg | Lys | Leu | Thr | Asn | |
| | | 875 | | | | | 880 | | | | | 885 | | | | |
| CCG | GTT | CAA | CTG | GAT | GAC | TTT | GAT | GCC | TAT | ATT | AAG | GAT | ATG | GCC | AAA | 3519 |
| Pro | Val | Gln | Leu | Asp | Asp | Phe | Asp | Ala | Tyr | Ile | Lys | Asp | Met | Ala | Lys | |
| | 890 | | | | | 895 | | | | | 900 | | | | | |
| GAC | TCT | GAC | TAT | AAA | TTT | TCT | CTT | CAG | TTT | GAG | GAG | TTG | AAA | TTG | ATT | 3567 |
| Asp | Ser | Asp | Tyr | Lys | Phe | Ser | Leu | Gln | Phe | Glu | Glu | Leu | Lys | Leu | Ile | |
| 905 | | | | | 910 | | | | | 915 | | | | | 920 | |
| GGA | CTG | GAT | ATC | CCA | CAC | TTT | GCT | GCA | GAT | CTT | CCA | CTG | AAT | CGA | TGT | 3615 |
| Gly | Leu | Asp | Ile | Pro | His | Phe | Ala | Ala | Asp | Leu | Pro | Leu | Asn | Arg | Cys | |
| | | | | 925 | | | | | 930 | | | | | 935 | | |
| AAA | AAC | CGT | TAC | ACA | AAC | ATC | CTA | CCA | TAT | GAC | TTC | AGC | CGT | GTG | AGA | 3663 |
| Lys | Asn | Arg | Tyr | Thr | Asn | Ile | Leu | Pro | Tyr | Asp | Phe | Ser | Arg | Val | Arg | |
| | | | 940 | | | | | 945 | | | | | 950 | | | |
| TTA | GTC | TCC | ATG | AAT | GAA | GAG | GAA | GGT | GCA | GAC | TAC | ATC | AAT | GCC | AAC | 3711 |
| Leu | Val | Ser | Met | Asn | Glu | Glu | Glu | Gly | Ala | Asp | Tyr | Ile | Asn | Ala | Asn | |
| | | 955 | | | | | 960 | | | | | 965 | | | | |
| TAT | ATT | CCT | GGA | TAC | AAC | TCA | CCC | CAG | GAG | TAT | ATT | GCC | ACC | CAG | GGG | 3759 |
| Tyr | Ile | Pro | Gly | Tyr | Asn | Ser | Pro | Gln | Glu | Tyr | Ile | Ala | Thr | Gln | Gly | |
| | 970 | | | | | 975 | | | | | 980 | | | | | |
| CCA | CTG | CCT | GAA | ACC | AGA | AAT | GAC | TTC | TGG | AAG | ATG | GTC | CTG | CAA | CAA | 3807 |
| Pro | Leu | Pro | Glu | Thr | Arg | Asn | Asp | Phe | Trp | Lys | Met | Val | Leu | Gln | Gln | |
| 985 | | | | | 990 | | | | | 995 | | | | | 1000 | |
| AAG | TCT | CAG | ATT | ATT | GTC | ATG | CTC | ACT | CAG | TGT | AAT | GAG | AAA | AGG | AGG | 3855 |
| Lys | Ser | Gln | Ile | Ile | Val | Met | Leu | Thr | Gln | Cys | Asn | Glu | Lys | Arg | Arg | |
| | | | | 1005 | | | | | 1010 | | | | | 1015 | | |
| GTG | AAA | TGT | GAC | CAT | TAC | TGG | CCA | TTC | ACG | GAA | GAA | CCT | ATA | GCC | TAT | 3903 |
| Val | Lys | Cys | Asp | His | Tyr | Trp | Pro | Phe | Thr | Glu | Glu | Pro | Ile | Ala | Tyr | |
| | | | 1020 | | | | | 1025 | | | | | 1030 | | | |
| GGA | GAC | ATC | ACT | GTG | GAG | ATG | ATT | TCA | GAG | GAA | GAG | CAG | GAC | GAC | TGG | 3951 |
| Gly | Asp | Ile | Thr | Val | Glu | Met | Ile | Ser | Glu | Glu | Glu | Gln | Asp | Asp | Trp | |
| | | | 1035 | | | | | 1040 | | | | | 1045 | | | |
| GCC | TGT | AGA | CAC | TTC | CGG | ATC | AAC | TAT | GCT | GAC | GAG | ATG | CAG | GAT | GTG | 3999 |
| Ala | Cys | Arg | His | Phe | Arg | Ile | Asn | Tyr | Ala | Asp | Glu | Met | Gln | Asp | Val | |
| | | | 1050 | | | | | 1055 | | | | | 1060 | | | |

-continued

```
ATG CAT TTT AAC TAC ACT GCA TGG CCT GAT CAT GGT GTG CCC ACA GCA         4047
Met His Phe Asn Tyr Thr Ala Trp Pro Asp His Gly Val Pro Thr Ala
1065                1070                1075                1080

AAT GCT GCA GAA AGT ATC CTG CAG TTT GTA CAC ATG GTC CGA CAG CAA         4095
Asn Ala Ala Glu Ser Ile Leu Gln Phe Val His Met Val Arg Gln Gln
                1085                1090                1095

GCT ACC AAG AGC AAA GGT CCC ATG ATC ATT CAC TGC AGT GCT GGC GTG         4143
Ala Thr Lys Ser Lys Gly Pro Met Ile Ile His Cys Ser Ala Gly Val
            1100                1105                1110

GGA CGG ACA GGA ACA TTC ATT GCC CTG GAC AGG CTC TTG CAG CAC ATT         4191
Gly Arg Thr Gly Thr Phe Ile Ala Leu Asp Arg Leu Leu Gln His Ile
        1115                1120                1125

CGG GAT CAT GAG TTT GTT GAC ATC TTA GGG CTG GTG TCA GAA ATG AGG         4239
Arg Asp His Glu Phe Val Asp Ile Leu Gly Leu Val Ser Glu Met Arg
    1130                1135                1140

TCA TAC CGG ATG TCT ATG GTA CAG ACA GAG GAG CAG TAC ATT TTT ATC         4287
Ser Tyr Arg Met Ser Met Val Gln Thr Glu Glu Gln Tyr Ile Phe Ile
1145                1150                1155                1160

CAT CAG TGT GTG CAA CTG ATG TGG ATG AAG AAG AAG CAG CAG ATC TGC         4335
His Gln Cys Val Gln Leu Met Trp Met Lys Lys Lys Gln Gln Ile Cys
                1165                1170                1175

ATC AGT GAT GTC ATA TAC GAG AAT GTT AGC AAG TCC T AGTTCAGAAT           4382
Ile Ser Asp Val Ile Tyr Glu Asn Val Ser Lys Ser
            1180                1185

CCGGAGCAGA GAGGACATGA TGTGCGCCCA TCCTCCCTTG CTTCCAGATT GTTTTAGTGG       4442

GCCCTGATGG TCATTTTTCT AAACAGAGGC CCTGCTTTGT AATATGTGGC CAAGGAGATA       4502

ATTTATCTCA CAGAAGCACC GGGAAGACTT AGCCTTAAAG AGCCTACAGT GTCCTTTGG        4562

ACTCTTTCAC TTCGGGACAT TAATAATGG ACCAAATTCA ACAGAACACC AGGAAGGTCA        4622

AGACGCTCTC CAAAGGGCAG GAAGTACAGC ACTTCCGAAG AGTTTAGTTG GCCCTTTGCT       4682

GGTTGGGCTG AGTTTTTTAT TTTTAAGTGT TTGTTTTTCA GTGCAATAAT TTTTGTGTGT       4742

GTGTGATTCC                                                              4752
```

(2) INFORMATION FOR SEQ ID NO:4:

(i) SEQUENCE CHARACTERISTICS:
        (A) LENGTH: 1188 amino acids
        (B) TYPE: amino acid
        (D) TOPOLOGY: linear (ii) MOLECULE TYPE: protein (xi) SEQUENCE DESCRIPTION: SEQ ID NO:4:

```
Met Gly His Leu Pro Thr Gly Ile His Gly Ala Arg Arg Leu Leu Pro
 1               5                  10                  15

Leu Leu Trp Leu Phe Val Leu Phe Lys Asn Ala Thr Ala Phe His Val
                20                  25                  30

Thr Val Gln Asp Asp Asn Asn Ile Val Val Ser Leu Glu Ala Ser Asp
            35                  40                  45

Val Ile Ser Pro Ala Ser Val Tyr Val Val Lys Ile Thr Gly Glu Ser
        50                  55                  60

Lys Asn Tyr Phe Phe Glu Phe Glu Glu Phe Asn Ser Thr Leu Pro Pro
65                  70                  75                  80

Pro Val Ile Phe Lys Ala Ser Tyr His Gly Leu Tyr Tyr Ile Ile Thr
                85                  90                  95

Leu Val Val Val Asn Gly Asn Val Val Thr Lys Pro Ser Arg Ser Ile
                100                 105                 110

Thr Val Leu Thr Lys Pro Leu Pro Val Thr Ser Val Ser Ile Tyr Asp
```

|   |   | 115 |   |   |   | 120 |   |   |   | 125 |   |   |
|---|---|---|---|---|---|---|---|---|---|---|---|---|
| Tyr | Lys | Pro | Ser | Pro | Glu | Thr | Gly | Val | Leu | Phe | Glu | Ile | His | Tyr | Pro |
|   | 130 |   |   |   |   | 135 |   |   |   | 140 |   |   |
| Glu | Lys | Tyr | Asn | Val | Phe | Thr | Arg | Val | Asn | Ile | Ser | Tyr | Trp | Glu | Gly |
| 145 |   |   |   |   | 150 |   |   |   | 155 |   |   |   |   |   | 160 |
| Lys | Asp | Phe | Arg | Thr | Met | Leu | Tyr | Lys | Asp | Phe | Phe | Lys | Gly | Lys | Thr |
|   |   |   | 165 |   |   |   |   | 170 |   |   |   |   |   | 175 |   |
| Val | Phe | Asn | His | Trp | Leu | Pro | Gly | Met | Cys | Tyr | Ser | Asn | Ile | Thr | Phe |
|   |   |   | 180 |   |   |   |   | 185 |   |   |   |   | 190 |   |   |
| Gln | Leu | Val | Ser | Glu | Ala | Thr | Phe | Asn | Lys | Ser | Thr | Leu | Val | Glu | Tyr |
|   |   | 195 |   |   |   |   | 200 |   |   |   |   | 205 |   |   |   |
| Ser | Gly | Val | Ser | His | Glu | Pro | Lys | Gln | His | Arg | Thr | Ala | Pro | Tyr | Pro |
|   | 210 |   |   |   |   | 215 |   |   |   |   | 220 |   |   |   |   |
| Pro | Gln | Asn | Ile | Ser | Val | Arg | Ile | Val | Asn | Leu | Asn | Lys | Asn | Asn | Trp |
| 225 |   |   |   |   | 230 |   |   |   |   | 235 |   |   |   |   | 240 |
| Glu | Glu | Gln | Ser | Gly | Asn | Phe | Pro | Glu | Glu | Ser | Phe | Met | Arg | Ser | Gln |
|   |   |   |   | 245 |   |   |   |   | 250 |   |   |   |   | 255 |   |
| Asp | Thr | Ile | Gly | Lys | Glu | Lys | Leu | Phe | His | Phe | Thr | Glu | Glu | Thr | Pro |
|   |   |   | 260 |   |   |   |   | 265 |   |   |   |   | 270 |   |   |
| Glu | Ile | Pro | Ser | Gly | Asn | Ile | Ser | Ser | Gly | Trp | Pro | Asp | Phe | Asn | Ser |
|   |   | 275 |   |   |   |   | 280 |   |   |   |   | 285 |   |   |   |
| Ser | Asp | Tyr | Glu | Thr | Thr | Ser | Gln | Pro | Tyr | Trp | Trp | Asp | Ser | Ala | Ser |
|   | 290 |   |   |   |   | 295 |   |   |   |   | 300 |   |   |   |   |
| Ala | Ala | Pro | Glu | Ser | Glu | Asp | Glu | Phe | Val | Ser | Val | Leu | Pro | Met | Glu |
| 305 |   |   |   |   | 310 |   |   |   |   | 315 |   |   |   |   | 320 |
| Tyr | Glu | Asn | Asn | Ser | Thr | Leu | Ser | Glu | Thr | Glu | Lys | Ser | Thr | Ser | Gly |
|   |   |   |   | 325 |   |   |   |   | 330 |   |   |   |   | 335 |   |
| Ser | Phe | Ser | Phe | Phe | Pro | Val | Gln | Met | Ile | Leu | Thr | Trp | Leu | Pro | Pro |
|   |   |   | 340 |   |   |   |   | 345 |   |   |   |   | 350 |   |   |
| Lys | Pro | Pro | Thr | Ala | Phe | Asp | Gly | Phe | His | Ile | His | Ile | Glu | Arg | Glu |
|   |   | 355 |   |   |   |   | 360 |   |   |   |   | 365 |   |   |   |
| Glu | Lys | Phe | Thr | Glu | Tyr | Leu | Met | Val | Asp | Glu | Glu | Ala | His | Glu | Phe |
|   | 370 |   |   |   |   | 375 |   |   |   |   | 380 |   |   |   |   |
| Val | Ala | Glu | Leu | Lys | Glu | Pro | Gly | Lys | Tyr | Lys | Leu | Ser | Val | Thr | Thr |
| 385 |   |   |   |   | 390 |   |   |   |   | 395 |   |   |   |   | 400 |
| Phe | Ser | Ser | Ser | Gly | Ser | Cys | Glu | Thr | Arg | Lys | Ser | Gln | Ser | Ala | Lys |
|   |   |   |   | 405 |   |   |   |   | 410 |   |   |   |   | 415 |   |
| Ser | Leu | Ser | Phe | Tyr | Ile | Ser | Pro | Ser | Gly | Glu | Trp | Ile | Glu | Glu | Leu |
|   |   |   | 420 |   |   |   |   | 425 |   |   |   |   | 430 |   |   |
| Thr | Glu | Lys | Pro | Gln | His | Val | Ser | Val | His | Val | Leu | Ser | Ser | Thr | Thr |
|   |   | 435 |   |   |   |   | 440 |   |   |   |   | 445 |   |   |   |
| Ala | Leu | Met | Ser | Trp | Thr | Ser | Ser | Gln | Glu | Asn | Tyr | Asn | Ser | Thr | Ile |
|   | 450 |   |   |   |   | 455 |   |   |   |   | 460 |   |   |   |   |
| Val | Ser | Val | Val | Ser | Leu | Thr | Cys | Gln | Lys | Gln | Lys | Glu | Ser | Gln | Arg |
| 465 |   |   |   |   | 470 |   |   |   |   | 475 |   |   |   |   | 480 |
| Leu | Glu | Lys | Gln | Tyr | Cys | Thr | Gln | Val | Asn | Ser | Ser | Lys | Pro | Ile | Ile |
|   |   |   |   | 485 |   |   |   |   | 490 |   |   |   |   | 495 |   |
| Glu | Asn | Leu | Val | Pro | Gly | Ala | Gln | Tyr | Gln | Val | Val | Ile | Tyr | Leu | Arg |
|   |   |   | 500 |   |   |   |   | 505 |   |   |   |   | 510 |   |   |
| Lys | Gly | Pro | Leu | Ile | Gly | Pro | Pro | Ser | Asp | Pro | Val | Thr | Phe | Ala | Ile |
|   |   |   | 515 |   |   |   |   | 520 |   |   |   |   | 525 |   |   |
| Val | Pro | Thr | Gly | Ile | Lys | Asp | Leu | Met | Leu | Tyr | Pro | Leu | Gly | Pro | Thr |
|   | 530 |   |   |   |   | 535 |   |   |   |   | 540 |   |   |   |   |

```
Ala  Val  Val  Leu  Ser  Trp  Thr  Arg  Pro  Tyr  Leu  Gly  Val  Phe  Arg  Lys
545                 550                 555                 560

Tyr  Val  Val  Glu  Met  Phe  Tyr  Phe  Asn  Pro  Ala  Thr  Met  Thr  Ser  Glu
                    565                 570                 575

Trp  Thr  Thr  Tyr  Tyr  Glu  Ile  Ala  Ala  Thr  Val  Ser  Leu  Thr  Ala  Ser
               580                 585                      590

Val  Arg  Ile  Ala  Asn  Leu  Leu  Pro  Ala  Trp  Tyr  Tyr  Asn  Phe  Arg  Val
          595                 600                      605

Thr  Met  Val  Thr  Trp  Gly  Asp  Pro  Glu  Leu  Ser  Cys  Cys  Asp  Ser  Ser
     610                      615                 620

Thr  Ile  Ser  Phe  Ile  Thr  Ala  Pro  Val  Ala  Pro  Glu  Ile  Thr  Ser  Val
625                 630                      635                           640

Glu  Tyr  Phe  Asn  Ser  Leu  Leu  Tyr  Ile  Ser  Trp  Thr  Tyr  Gly  Asp  Asp
                    645                      650                      655

Thr  Thr  Asp  Leu  Ser  His  Ser  Arg  Met  Leu  His  Trp  Met  Val  Val  Ala
               660                 665                      670

Glu  Gly  Lys  Lys  Lys  Ile  Lys  Lys  Ser  Val  Thr  Arg  Asn  Val  Met  Thr
               675                 680                 685

Ala  Ile  Leu  Ser  Leu  Pro  Pro  Gly  Asp  Ile  Tyr  Asn  Leu  Ser  Val  Thr
690                      695                      700

Ala  Cys  Thr  Glu  Arg  Gly  Ser  Asn  Thr  Ser  Met  Leu  Arg  Leu  Val  Lys
705                 710                      715                           720

Leu  Glu  Pro  Ala  Pro  Pro  Lys  Ser  Leu  Phe  Ala  Val  Asn  Lys  Thr  Gln
                    725                 730                      735

Thr  Ser  Val  Thr  Leu  Leu  Trp  Val  Glu  Glu  Gly  Val  Ala  Asp  Phe  Phe
               740                 745                      750

Glu  Val  Phe  Cys  Gln  Gln  Val  Gly  Ser  Ser  Gln  Lys  Thr  Lys  Leu  Gln
               755                 760                 765

Glu  Pro  Val  Ala  Val  Ser  Ser  His  Val  Val  Thr  Ile  Ser  Ser  Leu  Leu
770                      775                      780

Pro  Ala  Thr  Ala  Tyr  Asn  Cys  Ser  Val  Thr  Ser  Phe  Ser  His  Asp  Ser
785                 790                      795                           800

Pro  Ser  Val  Pro  Thr  Phe  Ile  Ala  Val  Ser  Thr  Met  Val  Thr  Glu  Met
               805                      810                      815

Asn  Pro  Asn  Val  Val  Ile  Ser  Val  Leu  Ala  Ile  Leu  Ser  Thr  Leu
               820                 825                      830

Leu  Ile  Gly  Leu  Leu  Leu  Val  Thr  Leu  Ile  Ile  Leu  Arg  Lys  Lys  His
          835                      840                 845

Leu  Gln  Met  Ala  Arg  Glu  Cys  Gly  Ala  Gly  Thr  Phe  Val  Asn  Phe  Ala
     850                      855                 860

Ser  Leu  Glu  Arg  Asp  Gly  Lys  Leu  Pro  Tyr  Asn  Trp  Ser  Lys  Asn  Gly
865                      870                 875                           880

Leu  Lys  Lys  Arg  Lys  Leu  Thr  Asn  Pro  Val  Gln  Leu  Asp  Asp  Phe  Asp
               885                      890                      895

Ala  Tyr  Ile  Lys  Asp  Met  Ala  Lys  Asp  Ser  Asp  Tyr  Lys  Phe  Ser  Leu
               900                 905                 910

Gln  Phe  Glu  Glu  Leu  Lys  Leu  Ile  Gly  Leu  Asp  Ile  Pro  His  Phe  Ala
     915                      920                 925

Ala  Asp  Leu  Pro  Leu  Asn  Arg  Cys  Lys  Asn  Arg  Tyr  Thr  Asn  Ile  Leu
     930                      935                 940

Pro  Tyr  Asp  Phe  Ser  Arg  Val  Arg  Leu  Val  Ser  Met  Asn  Glu  Glu  Glu
945                      950                      955                      960

Gly  Ala  Asp  Tyr  Ile  Asn  Ala  Asn  Tyr  Ile  Pro  Gly  Tyr  Asn  Ser  Pro
               965                      970                      975
```

```
Gln Glu Tyr Ile Ala Thr Gln Gly Pro Leu Pro Glu Thr Arg Asn Asp
            980                 985                 990
Phe Trp Lys Met Val Leu Gln Gln Lys Ser Gln Ile Ile Val Met Leu
        995                1000                1005
Thr Gln Cys Asn Glu Lys Arg Arg Val Lys Cys Asp His Tyr Trp Pro
    1010                1015                1020
Phe Thr Glu Glu Pro Ile Ala Tyr Gly Asp Ile Thr Val Glu Met Ile
1025                1030                1035                1040
Ser Glu Glu Glu Gln Asp Asp Trp Ala Cys Arg His Phe Arg Ile Asn
                1045                1050                1055
Tyr Ala Asp Glu Met Gln Asp Val Met His Phe Asn Tyr Thr Ala Trp
            1060                1065                1070
Pro Asp His Gly Val Pro Thr Ala Asn Ala Ala Glu Ser Ile Leu Gln
        1075                1080                1085
Phe Val His Met Val Arg Gln Gln Ala Thr Lys Ser Lys Gly Pro Met
    1090                1095                1100
Ile Ile His Cys Ser Ala Gly Val Gly Arg Thr Gly Thr Phe Ile Ala
1105                1110                1115                1120
Leu Asp Arg Leu Leu Gln His Ile Arg Asp His Glu Phe Val Asp Ile
                1125                1130                1135
Leu Gly Leu Val Ser Glu Met Arg Ser Tyr Arg Met Ser Met Val Gln
            1140                1145                1150
Thr Glu Glu Gln Tyr Ile Phe Ile His Gln Cys Val Gln Leu Met Trp
        1155                1160                1165
Met Lys Lys Lys Gln Gln Ile Cys Ile Ser Asp Val Ile Tyr Glu Asn
    1170                1175                1180
Val Ser Lys Ser
1185
```

( 2 ) INFORMATION FOR SEQ ID NO:5:

( i ) SEQUENCE CHARACTERISTICS:
        ( A ) LENGTH: 4815 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:5:

```
TTCCGGAGTT TGCGCTTCTA TTGATCCAAT CCCATTGCCC AGATATTGAA CACAGTACCC      60
AACAGGAAGT TTTTCAGCAC TTGCCCCACT CCCTCATTTT GGAGTCCCAA GTGTCTTTTG     120
TTCCCAGCTT CATATCTGTG TGTACCCAAG ATTTAGCTCT CACTTATAAG TGAGAACATG     180
TGGCATTTGT TTTTTGTTT  CTGCGTTAAT TTGCTAAAGA TAATGGCCTC CAGCTCCATC     240
TGTGTTCCTG CAAAGAACAT GATCTCATTC TTCTTATGGA TGCATAGTAT TCCATGATGT     300
ATATGTACCA CATTGTATTA GTCTGTTTCC ATGCTGCTGA TAAAGACTTA CCCGAGACTG     360
GGCAATTTAC AAAAGAAAGA GGTTTAATTG GACTCACAGT TCCATGTGGC TGGGGAGACC     420
TCATAATCAT GGCAGAAGGC AAGGCCAGGG ATGCTGCTAG GCATCCTAAA ATGCAGAGGC     480
CACGGTCCAC AATAGAGCTT CAACAGCTCC AAGGCCGGAA TTCCGGGCAG CCGCGGTGGT     540
GGCGGCGGCA GAGCCTCGCC CACTCCAATC CCCACCCTCT CCATCCTTAG TCATTAAAGA     600
ACAGCAGCGC CTGGCACGTT CTTGGAGGAC CCCGGGCGCA GAGGAGGAAA GGGAGCAGGC     660
GCAGGGGGAC TGGAAAGGCA GCATGCGCTC GCCAGGAGCA ACCTCGGCGC CAGGGTCTG     720
AGGCTGCAGC CCCAGTTCGC CATTGTGAGC CGCCGCCGGG GGAGTCCGCT AGCGCAGCCG     780
```

```
TGCCCCCGAG  TCCCCGTCCG  CGCAGCGATG  GGGCACCTGC  CCACGGGGAT  ACACGGCGCC   840
CGCCGCCTCC  TGCCTCTGCT  CTGGCTCTTT  GTGCTGTTCA  AGAATGCTAC  AGCTTTCCAT   900
GTAACTGTCC  AAGATGATAA  TAACATCGTT  GTCTCATTAG  AAGCTTCAGA  CGTCATCAGT   960
CCAGCATCTG  TGTATGTTGT  GAAGATAACT  GGTGAATCCA  AAAATTATTT  CTTCGAATTT   1020
GAGGAATTCA  ACAGCACTTT  GCCTCCTCCT  GTTATTTTCA  AGGCCAGTTA  TCATGGCCTT   1080
TATTATATAA  TCACTCTGGT  AGTGGTAAAT  GGAAATGTGG  TGACCAAGCC  ATCCAGATCA   1140
ATCACTGTGT  TAACAAAACC  TCTACCTGTA  ACCAGTGTTT  CCATATATGA  CTATAAACCT   1200
TCTCCTGAAA  CAGGAGTCCT  GTTTGAAATA  CATTATCCAG  AAAAATATAA  CGTTTTCACA   1260
AGAGTGAACA  TTAGCTACTG  GGAAGGTAAA  GACTTCCGGA  CAATGCTATA  TAAAGATTTC   1320
TTTAAGGGAA  AAACAGTATT  TAATCACTGG  CTGCCAGGAA  TGTGTTATAG  TAATATCACC   1380
TTTCAGCTGG  TATCTGAGGC  AACTTTTAAT  AAAAGTACCC  TTGTTGAGTA  CAGTGGTGTC   1440
AGTCACGAAC  CCAAACAGCA  CAGAACTGCC  CCTTATCCAC  CTCAAAATAT  TTCCGTTCGT   1500
ATCGTAAACT  TGAACAAAAA  CAACTGGGAA  GAACAGAGTG  GCAATTTCCC  AGAAGAATCC   1560
TTCATGAGAT  CACAAGATAC  AATAGGAAAA  GAAAAACTCT  TCCATTTTAC  AGAAGAAACC   1620
CCTGAAATTC  CCTCGGGCAA  CATTTCTTCC  GGTTGGCCTG  ATTTAATAG  CAGTGACTAT   1680
GAAACTACGT  CTCAGCCATA  TTGGTGGGAC  AGTGCATCTG  CAGCTCCTGA  AAGTGAAGAT   1740
GAATTTGTCA  GCGTACTTCC  CATGGAATAC  GAAAATAACA  GTACACTCAG  TGAGACAGAG   1800
AAGTCAACAT  CAGGCTCTTT  CTCCTTTTTC  CCTGTGCAAA  TGATATTGAC  CTGGTTACCA   1860
CCCAAACCAC  CCACTGCTTT  TGATGGGTTC  CATATCCATA  TTGAACGAGA  AGAGAAGTTT   1920
ACTGAATATT  TGATGGTGGA  TGAAGAAGCA  CATGAATTTG  TTGCAGAACT  GAAGGAACCT   1980
GGGAAATATA  AGTTATCTGT  GACAACCTTT  AGTTCCTCAG  GATCTTGTGA  AACTCGAAAA   2040
AGTCAGTCAG  CAAAATCACT  CAGCTTTTAT  ATCAGTCCTT  CAGGAGAGTG  GATTGAAGAA   2100
CTGACCGAGA  AGCCGCAGCA  CGTGAGTGTC  CACGTTTTAA  GCTCAACCAC  TGCCTTGATG   2160
TCCTGGACAT  CTTCCCAAGA  GAACTACAAC  AGCACCATTG  TGTCTGTGGT  GTCGCTGACC   2220
TGCCAGAAAC  AAAAGGAGAG  CCAGAGGCTT  GAAAAGCAGT  ACTGCACTCA  GGTGAACTCA   2280
AGCAAACCTA  TTATTGAAAA  TCTGGTTCCT  GGTGCCCAGT  ACCAGGTTGT  AATATACCTA   2340
AGGAAAGGCC  CTTTGATTGG  ACCACCTTCA  GATCCTGTGA  CATTGCTAT  TGTTCCCACA   2400
GGAATAAAGG  ATTTAATGCT  CTATCCTTTG  GGTCCTACGG  CCGTGGTTCT  GAGCTGGACC   2460
AGACCTTATT  TAGGCGTGTT  CAGAAAATAC  GTGGTTGAAA  TGTTTATTT  CAACCCTGCT   2520
ACAATGACAT  CAGAGTGGAC  CACCTACTAT  GAAATAGCAG  CAACTGTTTC  CTTAACTGCA   2580
TCCGTGAGAA  TAGCTAATCT  GCTGCCAGCA  TGGTACTACA  ACTTCCGGGT  TACCATGGTG   2640
ACGTGGGGAG  ATCCAGAATT  GAGCTGCTGT  GACAGCTCTA  CCATCAGCTT  CATAACAGCC   2700
CCAGTGGCTC  CGGAAATCAC  TTCTGTGGAA  TATTTCAACA  GTCTGTTATA  TATCAGTTGG   2760
ACATATGGGG  ATGATACAAC  GGACTTGTCC  CATTCTAGAA  TGCTTCACTG  GATGGTGGTT   2820
GCAGAAGGAA  AAAAGAAAAT  TAAAAAGAGT  GTAACACGCA  ATGTCATGAC  TGCAATTCTC   2880
AGCTTGCCTC  CAGGAGACAT  CTATAACCTC  TCAGTAACTG  CTTGTACTGA  AAGAGGAAGT   2940
AATACCTCCA  TGCTCCGCCT  TGTCAAGCTA  GAACCAGCTC  CACCCAAATC  ACTCTTCGCA   3000
GTGAACAAAA  CCCAGACTTC  AGTGACTTTG  CTGTGGGTGG  AAGAGGGAGT  AGCTGATTTC   3060
TTTGAAGTTT  TCTGTCAACA  AGTTGGCTCC  AGTCAGAAAA  CCAAACTTCA  GGAACCAGTT   3120
GCTGTTTCTT  CCCATGTCGT  GACCATCTCC  AGCCTTCTTC  CTGCCACTGC  CTACAATTGT   3180
```

-continued

```
AGTGTCACCA GCTTTAGCCA TGACAGCCCC AGTGTCCCTA CGTTCATAGC CGTCTCAACA    3240
ATGGTTACAG AGATGAATCC CAATGTGGTA GTGATCTCCG TGCTGGCCAT CCTTAGCACA    3300
CTTTTAATTG GACTGTTGCT TGTTACCCTC ATTATTCTTA GGAAAAAGCA TCTGCAGATG    3360
GCTAGGGAGT GTGGAGCTGG TACATTTGTC AATTTTGCAT CCTTAGAGAG GGATGGAAAG    3420
CTTCCATACA ACTGTGTTGC TCGAATCTCT TCCTGGGGTG GTAGCAGAAT CAGTGTGGAG    3480
CACCAGTACC CAGTTAGGAG TAAAAATGGT TTAAAGAAGA GGAAACTGAC AAACCCGGTT    3540
CAACTGGATG ACTTTGATGC CTATATTAAG GATATGGCCA AAGACTCTGA CTATAAATTT    3600
TCTCTTCAGT TTGAGGAGTT GAAATTGATT GGACTGGATA TCCCACACTT TGCTGCAGAT    3660
CTTCCACTGA ATCGATGTAA AAACCGTTAC ACAAACATCC TACCATATGA CTTCAGCCGT    3720
GTGAGATTAG TCTCCATGAA TGAAGAGGAA GGTGCAGACT ACATCAATGC CAACTATATT    3780
CCTGGATACA ACTCACCCCA GGAGTATATT GCCACCCAGG GGCCACTGCC TGAAACCAGA    3840
AATGACTTCT GGAAGATGGT CCTGCAACAA AAGTCTCAGA TTATTGTCAT GCTCACTCAG    3900
TGTAATGAGA AAGGAGGGT GAAATGTGAC CATTACTGGC CATTCACGGA AGAACCTATA     3960
GCCTATGGAG ACATCACTGT GGAGATGATT TCAGAGGAAG AGCAGGACGA CTGGGCCTGT    4020
AGACACTTCC GGATCAACTA TGCTGACGAG ATGCAGGATG TGATGCATTT TAACTACACT    4080
GCATGGCCTG ATCATGGTGT GCCCACAGCA AATGCTGCAG AAAGTATCCT GCAGTTTGTA    4140
CACATGGTCC GACAGCAAGC TACCAAGAGC AAAGGTCCCA TGATCATTCA CTGCAGTGCT    4200
GGCGTGGGAC GGACAGGAAC ATTCATTGCC CTGGACAGGC TCTTGCAGCA CATTCGGGAT    4260
CATGAGTTTG TTGACATCTT AGGGCTGGTG TCAGAAATGA GGTCATACCG GATGTCTATG    4320
GTACAGACAG AGGAGCAGTA CATTTTTATC CATCAGTGTG TGCAACTGAT GTGGATGAAG    4380
AAGAAGCAGC AGATCTGCAT CAGTGATGTC ATATACGAGA ATGTTAGCAA GTCCTAGTTC    4440
AGAATCCGGA GCAGAGAGGA CATGATGTGC GCCCATCCTC CCTTGCTTCC AGATTGTTTT    4500
AGTGGGCCCT GATGGTCATT TTTCTAAACA GAGGCCCTGC TTTGTAATAT GTGGCCAAGG    4560
AGATAATTTA TCTCACAGAA GCACCGGGAA GACTTAGCCT TAAAGAGCCT ACAGTGTCCT    4620
TTTGGACTCT TTCACTTCGG GACATTTAAT AATGGACCAA ATTCAACAGA ACACCAGGAA    4680
GGTCAAGACG CTCTCCAAAG GGCAGGAAGT ACAGCACTTC CGAAGAGTTT AGTTGGCCCT    4740
TTGCTGGTTG GGCTGAGTTT TTTATTTTTA AGTGTTTGTT TTTCAGTGCA ATAATTTTTG    4800
TGTGTGTGTG ATTCC                                                    4815
```

( 2 ) INFORMATION FOR SEQ ID NO:6:

( i ) SEQUENCE CHARACTERISTICS:
        ( A ) LENGTH: 4799 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:6:

```
TTCCGGAGTT TGCGCTTCTA TTGATCCAAT CCCATTGCCC AGATATTGAA CACAGTACCC     60
AACAGGAAGT TTTCAGCAC TTGCCCCACT CCCTCATTTT GGAGTCCCAA GTGTCTTTTG    120
TTCCCAGCTT CATATCTGTG TGTACCCAAG ATTTAGCTCT CACTTATAAG TGAGAACATG    180
TGGCATTTGT TTTTTTGTTT CTGCGTTAAT TTGCTAAAGA TAATGGCCTC CAGCTCCATC    240
TGTGTTCCTG CAAAGAACAT GATCTCATTC TTCTTATGGA TGCATAGTAT CCATGATGT    300
ATATGTACCA CATTGTATTA GTCTGTTTCC ATGCTGCTGA TAAAGACTTA CCCGAGACTG    360
GGCAATTTAC AAAAGAAAGA GGTTTAATTG GACTCACAGT TCCATGTGGC TGGGGAGACC    420
```

```
TCATAATCAT  GGCAGAAGGC  AAGGCCAGGG  ATGCTGCTAG  GCATCCTAAA  ATGCAGAGGC   480
CACGGTCCAC  AATAGAGCTT  CAACAGCTCC  AAGGCCGGAA  TTCCGGGCAG  CCGCGGTGGT   540
GGCGGCGGCA  GAGCCTCGCC  CACTCCAATC  CCCACCCTCT  CCATCCTTAG  TCATTAAAGA   600
ACAGCAGCGC  CTGGCACGTT  CTTGGAGGAC  CCCGGGCGCA  GAGGAGGAAA  GGGAGCAGGC   660
GCAGGGGGAC  TGGAAAGGCA  GCATGCGCTC  GCCAGGAGCA  ACCTCGGCGC  CAGGGTCTG    720
AGGCTGCAGC  CCCAGTTCGC  CATTGTGAGC  CGCCGCCGGG  GGAGTCCGCT  AGCGCAGCCG   780
TGCCCCCGAG  TCCCCGTCCG  CGCAGCGATG  GGGCACCTGC  CCACGGGGAT  ACACGGCGCC   840
CGCCGCCTCC  TGCCTCTGCT  CTGGCTCTTT  GTGCTGTTCA  GAATGCTAC   AGCTTTCCAT   900
GTAACTGTCC  AAGATGATAA  TAACATCGTT  GTCTCATTAG  AAGCTTCAGA  CGTCATCAGT   960
CCAGCATCTG  TGTATGTTGT  GAAGATAACT  GGTGAATCCA  AAATTATTT   CTTCGAATTT  1020
GAGGAATTCA  ACAGCACTTT  GCCTCCTCCT  GTTATTTTCA  AGGCAGTTA   TCATGGCCTT  1080
TATTATATAA  TCACTCTGGT  AGTGGTAAAT  GGAAATGTGG  TGACCAAGCC  ATCCAGATCA  1140
ATCACTGTGT  TAACAAAACC  TCTACCTGTA  ACCAGTGTTT  CCATATATGA  CTATAAACCT  1200
TCTCCTGAAA  CAGGAGTCCT  GTTTGAAATA  CATTATCCAG  AAAAATATAA  CGTTTTCACA  1260
AGAGTGAACA  TTAGCTACTG  GGAAGGTAAA  GACTTCCGGA  CAATGCTATA  TAAAGATTTC  1320
TTTAAGGGAA  AAACAGTATT  TAATCACTGG  CTGCCAGGAA  TGTGTTATAG  TAATATCACC  1380
TTTCAGCTGG  TATCTGAGGC  AACTTTTAAT  AAAAGTACCC  TTGTTGAGTA  CAGTGGTGTC  1440
AGTCACGAAC  CCAAACAGCA  CAGAACTGCC  CCTTATCCAC  CTCAAAATAT  TTCCGTTCGT  1500
ATCGTAAACT  TGAACAAAAA  CAACTGGGAA  GAACAGAGTG  GCAATTTCCC  AGAAGAATCC  1560
TTCATGAGAT  CACAAGATAC  AATAGGAAAA  GAAAAACTCT  TCCATTTTAC  AGAAGAAACC  1620
CCTGAAATTC  CCTCGGGCAA  CATTTCTTCC  GGTTGGCCTG  ATTTAATAG   CAGTGACTAT  1680
GAAACTACGT  CTCAGCCATA  TTGGTGGGAC  AGTGCATCTG  CAGCTCCTGA  AAGTGAAGAT  1740
GAATTTGTCA  GCGTACTTCC  CATGGAATAC  GAAAATAACA  GTACACTCAG  TGAGACAGAG  1800
AAGTCAACAT  CAGGCTCTTT  CTCCTTTTTC  CCTGTGCAAA  TGATATTGAC  CTGGTTACCA  1860
CCCAAACCAC  CCACTGCTTT  TGATGGGTTC  CATATCCATA  TTGAACGAGA  AGAGAAGTTT  1920
ACTGAATATT  TGATGGTGGA  TGAAGAAGCA  CATGAATTTG  TTGCAGAACT  GAAGGAACCT  1980
GGGAAATATA  AGTTATCTGT  GACAACCTTT  AGTTCCTCAG  GATCTTGTGA  AACTCGAAAA  2040
AGTCAGTCAG  CAAAATCACT  CAGCTTTTAT  ATCAGTCCTT  CAGGAGAGTG  GATTGAAGAA  2100
CTGACCGAGA  AGCCGCAGCA  CGTGAGTGTC  CACGTTTTAA  GCTCAACCAC  TGCCTTGATG  2160
TCCTGGACAT  CTTCCCAAGA  GAACTACAAC  AGCACCATTG  TGTCTGTGGT  GTCGCTGACC  2220
TGCCAGAAAC  AAAAGGAGAG  CCAGAGGCTT  GAAAAGCAGT  ACTGCACTCA  GGTGAACTCA  2280
AGCAAACCTA  TTATTGAAAA  TCTGGTTCCT  GGTGCCCAGT  ACCAGGTTGT  AATATACCTA  2340
AGGAAAGGCC  CTTTGATTGG  ACCACCTTCA  GATCCTGTGA  CATTTGCTAT  TGTTCCCACA  2400
GGAATAAAGG  ATTTAATGCT  CTATCCTTTG  GGTCCTACGG  CCGTGGTTCT  GAGCTGGACC  2460
AGACCTTATT  TAGGCGTGTT  CAGAAAATAC  GTGGTTGAAA  TGTTTTATTT  CAACCCTGCT  2520
ACAATGACAT  CAGAGTGGAC  CACCTACTAT  GAAATAGCAG  CAACTGTTTC  CTTAACTGCA  2580
TCCGTGAGAA  TAGCTAATCT  GCTGCCAGCA  TGGTACTACA  ACTTCCGGGT  TACCATGGTG  2640
ACGTGGGGAG  ATCCAGAATT  GAGCTGCTGT  GACAGCTCTA  CCATCAGCTT  CATAACAGCC  2700
CCAGTGGCTC  CGGAAATCAC  TTCTGTGGAA  TATTTCAACA  GTCTGTTATA  TATCAGTTGG  2760
ACATATGGGG  ATGATACAAC  GGACTTGTCC  CATTCTAGAA  TGCTTCACTG  GATGGTGGTT  2820
```

-continued

```
GCAGAAGGAA AAAAGAAAAT TAAAAGAGT GTAACACGCA ATGTCATGAC TGCAATTCTC      2880
AGCTTGCCTC CAGGAGACAT CTATAACCTC TCAGTAACTG CTTGTACTGA AAGAGGAAGT      2940
AATACCTCCA TGCTCCGCCT TGTCAAGCTA GAACCAGCTC CACCCAAATC ACTCTTCGCA      3000
GTGAACAAAA CCCAGACTTC AGTGACTTTG CTGTGGGTGG AAGAGGGAGT AGCTGATTTC      3060
TTTGAAGTTT TCTGTCAACA AGTTGGCTCC AGTCAGAAAA CCAAACTTCA GGAACCAGTT      3120
GCTGTTTCTT CCCATGTCGT GACCATCTCC AGCCTTCTTC CTGCCACTGC CTACAATTGT      3180
AGTGTCACCA GCTTTAGCCA TGACAGCCCC AGTGTCCCTA CGTTCATAGC CGTCTCAACA      3240
ATGGTACAG AGATGAATCC CAATGTGGTA GTGATCTCCG TGCTGGCCAT CCTTAGCACA      3300
CTTTTAATTG GACTGTTGCT TGTTACCCTC ATTATTCTTA GGAAAAAGCA TCTGCAGATG      3360
GCTAGGGAGT GTGGAGCTGG TACATTGTC AATTTTGCAT CCTTAGAGAG GGATGGAAAG      3420
CTTCCATACA ACTGGAGTAA AAATGGTTTA AAGAAGAGGA AACTGACAAA CCCGGTTCAA      3480
CTGGATGACT TTGATGCCTA TATTAAGGAT ATGGCCAAAG ACTCTGACTA TAAATTTTCT      3540
CTTCAGTTTG AGGACACATA TTTCTTTGGA TCTAAAACCA TATGTCAGAA GAGATGGAAG      3600
AGTTGAAATT GATTGGACTG GATATCCCAC ACTTGCTGC AGATCTTCCA CTGAATCGAT      3660
GTAAAACCG TTACACAAAC ATCCTACCAT ATGACTTCAG CCGTGTGAGA TTAGTCTCCA      3720
TGAATGAAGA GGAAGGTGCA GACTACATCA ATGCCAACTA TATTCCTGGA TACAACTCAC      3780
CCCAGGAGTA TATTGCCACC CAGGGGCCAC TGCCTGAAAC CAGAAATGAC TTCTGGAAGA      3840
TGGTCCTGCA ACAAAAGTCT CAGATTATTG TCATGCTCAC TCAGTGTAAT GAGAAAGGA      3900
GGGTGAAATG TGACCATTAC TGGCCATTCA CGGAAGAACC TATAGCCTAT GGAGACATCA      3960
CTGTGGAGAT GATTTCAGAG GAAGAGCAGG ACGACTGGGC CTGTAGACAC TTCCGGATCA      4020
ACTATGCTGA CGAGATGCAG GATGTGATGC ATTTTAACTA CACTGCATGG CCTGATCATG      4080
GTGTGCCCAC AGCAAATGCT GCAGAAAGTA TCCTGCAGTT TGTACACATG GTCCGACAGC      4140
AAGCTACCAA GAGCAAAGGT CCCATGATCA TTCACTGCAG TGCTGGCGTG GGACGGACAG      4200
GAACATTCAT TGCCCTGGAC AGGCTCTTGC AGCACATTCG GGATCATGAG TTTGTTGACA      4260
TCTTAGGGCT GGTGTCAGAA ATGAGGTCAT ACCGGATGTC TATGGTACAG ACAGAGGAGC      4320
AGTACATTTT TATCCATCAG TGTGTGCAAC TGATGTGGAT GAAGAAGAAG CAGCAGATCT      4380
GCATCAGTGA TGTCATATAC GAGAATGTTA GCAAGTCCTA GTTCAGAATC CGGAGCAGAG      4440
AGGACATGAT GTGCGCCCAT CCTCCCTTGC TTCCAGATTG TTTAGTGGG CCCTGATGGT      4500
CATTTTTCTA AACAGAGGCC CTGCTTTGTA ATATGTGGCC AAGGAGATAA TTTATCTCAC      4560
AGAAGCACCG GGAAGACTTA GCCTTAAAGA GCCTACAGTG TCCTTTTGGA CTCTTTCACT      4620
TCGGGACATT TAATAATGGA CCAAATTCAA CAGAACACCA GGAAGGTCAA GACGCTCTCC      4680
AAAGGGCAGG AAGTACAGCA CTTCCGAAGA GTTTAGTTGG CCCTTTGCTG GTTGGGCTGA      4740
GTTTTTTATT TTAAGTGTT TGTTTTCAG TGCAATAATT TTTGTGTGTG TGTGATTCC       4799
```

( 2 ) INFORMATION FOR SEQ ID NO:7:

( i ) SEQUENCE CHARACTERISTICS:
        ( A ) LENGTH: 11 amino acids
        ( B ) TYPE: amino acid
        ( D ) TOPOLOGY: linear ( x i ) SEQUENCE DESCRIPTION: SEQ ID NO:7:

```
Leu  Leu  Pro  Leu  Leu  Trp  Leu  Phe  Val  Leu  Leu
 1              5                        10
```

( 2 ) INFORMATION FOR SEQ ID NO:8:

( i ) SEQUENCE CHARACTERISTICS:
        ( A ) LENGTH: 4 amino acids
        ( B ) TYPE: amino acid
        ( D ) TOPOLOGY: linear ( x i ) SEQUENCE DESCRIPTION: SEQ ID NO:8:

```
Arg Lys Lys His
 1
```

( 2 ) INFORMATION FOR SEQ ID NO:9:

( i ) SEQUENCE CHARACTERISTICS:
        ( A ) LENGTH: 11 amino acids
        ( B ) TYPE: amino acid
        ( D ) TOPOLOGY: linear ( i x ) FEATURE:
        ( A ) NAME/KEY: Active-site
        ( B ) LOCATION: 1
        ( D ) OTHER INFORMATION: /label=Xaa
            / note="Xaa =I/V"

( i x ) FEATURE:
        ( A ) NAME/KEY: Active-site
        ( B ) LOCATION: 10
        ( D ) OTHER INFORMATION: /label=Xaa
            / note="Xaa =S/T"

( x i ) SEQUENCE DESCRIPTION: SEQ ID NO:9:

```
Xaa His Cys Xaa Ala Gly Xaa Xaa Arg Xaa Gly
 1               5                   10
```

( 2 ) INFORMATION FOR SEQ ID NO:10:

( i ) SEQUENCE CHARACTERISTICS:
        ( A ) LENGTH: 12 amino acids
        ( B ) TYPE: amino acid
        ( D ) TOPOLOGY: linear ( x i ) SEQUENCE DESCRIPTION: SEQ ID NO:10:

```
Ser Lys Asn Gly Leu Lys Lys Arg Lys Leu Thr Asn
 1               5                   10
```

( 2 ) INFORMATION FOR SEQ ID NO:11:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

```
TTTGGATCCC CAGTTCAACT GGATGACTTT                          30
```

( 2 ) INFORMATION FOR SEQ ID NO:12:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

```
TTTGAATTCC TAGGACTTGC TAACATTTTC                          30
```

( 2 ) INFORMATION FOR SEQ ID NO:13:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:13:

TTTGGATCCA CAAAACCTCT ACCTGTAACC    30

( 2 ) INFORMATION FOR SEQ ID NO:14:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:14:

TTTGAATTCT TCAAGCCTCT GGCTCTCCTT    30

( 2 ) INFORMATION FOR SEQ ID NO:15:

( i ) SEQUENCE CHARACTERISTICS:
    ( A ) LENGTH: 49 amino acids
    ( B ) TYPE: amino acid
    ( D ) TOPOLOGY: linear ( x i ) SEQUENCE DESCRIPTION: SEQ ID NO:15:

| Leu | Ser | Pro | Pro | Thr | Asn | Leu | His | Leu | Glu | Ala | Asn | Pro | Asp | Thr | Gly |
| 1 | | | | 5 | | | | | 10 | | | | | 15 | |

| Val | Leu | Thr | Val | Ser | Trp | Glu | Arg | Ser | Thr | Thr | Pro | Asp | Ile | Thr | Gly |
| | | | 20 | | | | | 25 | | | | | 30 | | |

| Tyr | Phe | Asp | Asn | Leu | Ser | Pro | Gly | Leu | Glu | Tyr | Asn | Val | Ser | Val | Tyr |
| | | 35 | | | | | 40 | | | | | 45 | | | |

Thr ( 2 ) INFORMATION FOR SEQ ID NO:16:

( i ) SEQUENCE CHARACTERISTICS:
    ( A ) LENGTH: 278 amino acids
    ( B ) TYPE: amino acid
    ( D ) TOPOLOGY: linear ( x i ) SEQUENCE DESCRIPTION: SEQ ID NO:16:

| Pro | Ile | Lys | Ile | Asn | Gln | Phe | Glu | Gly | His | Phe | Met | Lys | Leu | Gln | Ala |
| 1 | | | | 5 | | | | | 10 | | | | | 15 | |

| Asp | Ser | Asn | Tyr | Leu | Leu | Ser | Lys | Glu | Tyr | Glu | Glu | Leu | Lys | Asp | Val |
| | | | 20 | | | | | 25 | | | | | 30 | | |

| Gly | Arg | Asn | Gln | Ser | Cys | Asp | Ile | Ala | Leu | Leu | Pro | Glu | Asn | Arg | Gly |
| | | 35 | | | | | 40 | | | | | 45 | | | |

| Lys | Asn | Arg | Tyr | Asn | Asn | Ile | Leu | Pro | Tyr | Asp | Ala | Thr | Arg | Val | Lys |
| | 50 | | | | | 55 | | | | | 60 | | | | |

| Leu | Ser | Asn | Val | Asp | Asp | Pro | Cys | Ser | Asp | Tyr | Ile | Asn | Ala | Ser | Ser |
| 65 | | | | | 70 | | | | | 75 | | | | | 80 |

| Tyr | Ile | Pro | Gly | Asn | Asn | Phe | Arg | Arg | Glu | Tyr | Ile | Val | Thr | Gln | Gly |
| | | | | 85 | | | | | 90 | | | | | 95 | |

| Pro | Leu | Pro | Gly | Thr | Lys | Asp | Asp | Phe | Trp | Lys | Met | Val | Trp | Glu | Gln |
| | | | 100 | | | | | 105 | | | | | 110 | | |

| Asn | Val | His | Asn | Ile | Val | Met | Val | Thr | Gln | Cys | Val | Glu | Lys | Gly | Arg |
| | | 115 | | | | | 120 | | | | | 125 | | | |

| Val | Lys | Cys | Asp | His | Tyr | Trp | Pro | Ala | Asp | Gln | Asp | Ser | Leu | Tyr | Tyr |
| | 130 | | | | | 135 | | | | | 140 | | | | |

```
Gly  Asp  Leu  Ile  Leu  Gln  Met  Leu  Ser  Glu  Ser  Val  Leu  Pro  Glu  Trp
145                      150                      155                      160

Thr  Ile  Arg  Glu  Phe  Lys  Ile  Cys  Gly  Glu  Gln  Leu  Asp  Ala  His
                    165                      170                      175

Arg  Leu  Ile  Arg  His  Phe  His  Tyr  Thr  Val  Trp  Pro  Asp  His  Gly  Val
               180                      185                      190

Pro  Glu  Thr  Thr  Gln  Ser  Leu  Ile  Gln  Phe  Val  Arg  Thr  Val  Arg  Asp
          195                      200                      205

Tyr  Ile  Asn  Arg  Ser  Pro  Gly  Ala  Gly  Pro  Thr  Val  Val  His  Cys  Ser
     210                      215                      220

Ala  Gly  Val  Gly  Arg  Thr  Gly  Thr  Phe  Ile  Ala  Leu  Asp  Arg  Ile  Leu
225                      230                      235                      240

Gln  Gln  Leu  Asp  Ser  Lys  Asp  Ser  Val  Asp  Ile  Phe  Gly  Ile  Val  Tyr
                    245                      250                      255

Ala  Met  Arg  Lys  Glu  Arg  Val  Trp  Met  Val  Gln  Thr  Glu  Gln  Gln  Tyr
               260                      265                      270

Ile  Cys  Ile  His  Gln  Cys
                    275
```

( 2 ) INFORMATION FOR SEQ ID NO:17:

( i ) SEQUENCE CHARACTERISTICS:
        ( A ) LENGTH: 273 amino acids
        ( B ) TYPE: amino acid
        ( D ) TOPOLOGY: linear ( x i ) SEQUENCE DESCRIPTION: SEQ ID NO:17:

```
Pro  Ile  Leu  Ile  Lys  Asn  Phe  Ala  Glu  His  Tyr  Arg  Leu  Met  Ser  Ala
1                   5                        10                       15

Asp  Ser  Asp  Phe  Arg  Phe  Ser  Glu  Glu  Phe  Glu  Glu  Leu  Lys  His  Val
                    20                       25                       30

Gly  Arg  Asp  Gln  Pro  Cys  Thr  Phe  Ala  Asp  Leu  Pro  Cys  Asn  Arg  Pro
               35                       40                       45

Lys  Asn  Arg  Phe  Thr  Asn  Ile  Leu  Pro  Tyr  Asp  His  Ser  Arg  Phe  Lys
     50                       55                       60

Leu  Gln  Pro  Val  Asp  Asp  Glu  Gly  Ser  Asp  Tyr  Ile  Asn  Ala  Asn
65                       70                       75                       80

Tyr  Val  Pro  Gly  His  Asn  Ser  Pro  Arg  Glu  Phe  Ile  Val  Thr  Gln  Gly
                    85                       90                       95

Pro  Leu  His  Ser  Thr  Arg  Asp  Asp  Phe  Trp  Arg  Met  Cys  Trp  Glu  Ser
               100                      105                      110

Asn  Ser  Arg  Ala  Ile  Val  Met  Leu  Thr  Arg  Cys  Phe  Glu  Lys  Gly  Arg
          115                      120                      125

Glu  Lys  Cys  Asp  Gln  Tyr  Trp  Pro  Asn  Asp  Thr  Val  Pro  Val  Phe  Tyr
     130                      135                      140

Gly  Asp  Ile  Lys  Val  Gln  Ile  Leu  Asn  Asp  Ser  His  Tyr  Ala  Asp  Trp
145                      150                      155                      160

Val  Met  Thr  Glu  Phe  Met  Leu  Cys  Arg  Gly  Ser  Glu  Gln  Arg  Ile  Leu
                    165                      170                      175

Arg  His  Phe  His  Phe  Thr  Thr  Trp  Pro  Asp  Phe  Gly  Val  Pro  Asn  Pro
               180                      185                      190

Pro  Gln  Thr  Leu  Val  Arg  Phe  Val  Arg  Ala  Phe  Arg  Asp  Arg  Ile  Gly
          195                      200                      205

Ala  Glu  Gln  Arg  Pro  Ile  Val  Val  His  Cys  Ser  Ala  Gly  Val  Gly  Arg
     210                      215                      220
```

| | | | | | | | | | | | | | | |
|---|---|---|---|---|---|---|---|---|---|---|---|---|---|---|
| Ser 225 | Gly | Thr | Phe | Ile | Thr 230 | Leu | Asp | Arg | Ile | Leu 235 | Gln | Gln | Ile | Asn | Thr 240 |
| Ser | Asp | Tyr | Val | Asp 245 | Ile | Leu | Gly | Leu | Val 250 | Ser | Glu | Met | Arg | Ser 255 | Tyr |
| Arg | Met | Ser | Met 260 | Val | Gln | Thr | Glu | Glu 265 | Gln | Tyr | Ile | Phe | Ile 270 | His | Gln |
| Cys | | | | | | | | | | | | | | | |